(12) United States Patent
Shih et al.

(10) Patent No.: US 10,076,247 B2
(45) Date of Patent: Sep. 18, 2018

(54) SYSTEM AND METHOD FOR EVALUATING TISSUE

(71) Applicants: Wan Y. Shih, Bryn Mawr, PA (US);
Wei-Heng Shih, Bryn Mawr, PA (US);
Hakki Yegingil, Philadelphia, PA (US);
Ari D. Brooks, Cherry Hill, NJ (US)

(72) Inventors: Wan Y. Shih, Bryn Mawr, PA (US);
Wei-Heng Shih, Bryn Mawr, PA (US);
Hakki Yegingil, Philadelphia, PA (US);
Ari D. Brooks, Cherry Hill, NJ (US)

(*) Notice: Subject to any disclaimer, the term of this patent is extended or adjusted under 35 U.S.C. 154(b) by 3 days.

(21) Appl. No.: 14/465,520

(22) Filed: Aug. 21, 2014

(65) Prior Publication Data

US 2015/0025418 A1   Jan. 22, 2015

Related U.S. Application Data

(62) Division of application No. 14/031,307, filed on Sep. 19, 2013, now Pat. No. 8,845,555, which is a division
(Continued)

(51) Int. Cl.
*A61B 5/103* (2006.01)
*A61B 5/00* (2006.01)
(Continued)

(52) U.S. Cl.
CPC .......... *A61B 5/0053* (2013.01); *A61B 5/4244* (2013.01); *A61B 5/4312* (2013.01);
(Continued)

(58) Field of Classification Search
CPC ... A61B 5/0053; A61B 5/4312; A61B 5/4381; A61B 5/441; A61B 5/4244
See application file for complete search history.

(56) References Cited

U.S. PATENT DOCUMENTS 3,205,464 A * 9/1965 Schwartz ................. G01L 1/18
338/2
4,093,883 A * 6/1978 Yamamoto ............. H01H 57/00
200/181
(Continued)

FOREIGN PATENT DOCUMENTS

CN       1877277 A    12/2006
CN       2924545 Y     7/2007
(Continued)

OTHER PUBLICATIONS

Wellman, P. S. et al., "Tactile Imaging: A Method for Documenting Breast Lumps".
(Continued)

*Primary Examiner* — Sean Dougherty
(74) *Attorney, Agent, or Firm* — Mendelsohn Dunleavy, P.C.

(57) ABSTRACT

A sensor system for measuring an elastic modulus and a shear modulus and a method for evaluating a tissue. The invention pertains to a method for determining the presence of and/or characterizing abnormal growths, using a piezoelectric finger sensor (PEFS) system. The PEFS system may be particularly useful for screening for tumors and various forms of cancer. Additionally, the PEFS system may be useful for various dermatological applications.

18 Claims, 30 Drawing Sheets

Related U.S. Application Data of application No. 12/992,923, filed as application No. PCT/US2009/044250 on May 15, 2009, now Pat. No. 8,562,546.

(60) Provisional application No. 61/054,100, filed on May 16, 2008.

(51) Int. Cl.
G01N 29/06 (2006.01)
A61B 8/08 (2006.01)
A61B 8/00 (2006.01)

(52) U.S. Cl.
CPC ............ *A61B 5/4381* (2013.01); *A61B 5/441* (2013.01); *A61B 8/085* (2013.01); *A61B 8/403* (2013.01); *A61B 8/485* (2013.01); *G01N 29/0672* (2013.01); *A61B 5/442* (2013.01); *G01N 2291/02475* (2013.01); *G01N 2291/02827* (2013.01)

(56) References Cited

U.S. PATENT DOCUMENTS

| | | | | |
|---|---|---|---|---|
| 4,302,694 A * | 11/1981 | Fujishima | ................ | G10G 7/02 29/25.35 |
| 4,349,762 A * | 9/1982 | Kitamura | ............ | H01L 41/0926 310/331 |
| 4,363,993 A * | 12/1982 | Nishigaki | ............... | G11B 5/592 310/332 |
| 4,528,502 A * | 7/1985 | Rocha | .................... | G01R 15/20 324/109 |
| 4,649,312 A * | 3/1987 | Robin | ....................... | G01L 1/16 310/319 |
| 4,802,371 A * | 2/1989 | Calderara | ................ | G01L 1/16 310/338 |
| 5,054,323 A * | 10/1991 | Hubbard, Jr. | ............. | G01L 1/16 310/338 |
| 5,313,535 A * | 5/1994 | Williams | .............. | G02F 1/0134 385/14 |
| 5,334,835 A * | 8/1994 | Nakayama | ............ | G01Q 60/16 250/307 |
| 5,338,999 A * | 8/1994 | Ramakrishnan | .... | H01L 41/1876 310/311 |
| 5,382,864 A * | 1/1995 | Morikawa | ............ | H01L 41/094 310/332 |
| 5,445,008 A * | 8/1995 | Wachter | ............... | G01N 29/036 422/88 |
| 5,475,318 A * | 12/1995 | Marcus | ................. | G01R 1/06711 219/543 |
| 5,503,010 A * | 4/1996 | Yamanaka | ............ | B82Y 35/00 73/105 |
| 5,553,486 A * | 9/1996 | Bonin | .................... | B82Y 35/00 361/283.1 |
| 5,628,728 A | 5/1997 | Ramakrishnan et al. | | |
| 5,689,063 A * | 11/1997 | Fujiu | ....................... | B82Y 35/00 73/105 |
| 5,719,324 A * | 2/1998 | Thundat | ............... | G01N 29/022 422/88 |
| 5,780,727 A * | 7/1998 | Gimzewski | ............ | B82Y 35/00 257/415 |
| 5,807,758 A * | 9/1998 | Lee | ....................... | B82Y 35/00 422/82.01 |
| 5,833,634 A | 11/1998 | Laird et al. | | |
| 5,866,807 A * | 2/1999 | Elings | ................... | B82Y 35/00 73/105 |
| 5,874,126 A * | 2/1999 | Kahn | .................... | C04B 35/622 252/62.9 PZ |
| 5,948,993 A * | 9/1999 | Ting | ....................... | G01H 11/08 73/777 |
| 5,966,787 A * | 10/1999 | Nakayama | ............ | B82Y 35/00 29/25.35 |
| 5,996,412 A * | 12/1999 | Hansen | ................ | G01P 15/0915 73/514.34 |
| 6,075,585 A * | 6/2000 | Minne | .................... | B82Y 10/00 250/234 |
| 6,278,379 B1 * | 8/2001 | Allen | .................. | B60C 23/0408 324/655 |
| 6,280,396 B1 * | 8/2001 | Clark | .................... | A61B 5/0537 600/547 |
| 6,289,717 B1 * | 9/2001 | Thundat | ........... | G01N 33/54373 422/68.1 |
| 6,336,366 B1 * | 1/2002 | Thundat | ................. | B82Y 35/00 310/331 |
| 6,422,069 B1 * | 7/2002 | Shimizu | ................. | B82Y 35/00 73/105 |
| 6,458,327 B1 * | 10/2002 | Vossmeyer | ............. | B82Y 10/00 422/68.1 |
| 6,465,368 B2 | 10/2002 | Inoue et al. | | |
| 6,468,231 B2 | 10/2002 | Sarvazyan et al. | | |
| 6,500,119 B1 | 12/2002 | West et al. | | |
| 6,511,427 B1 | 1/2003 | Sliwa, Jr. et al. | | |
| 6,589,727 B1 | 7/2003 | Klenerman et al. | | |
| 6,620,115 B2 | 9/2003 | Sarvazyan et al. | | |
| 6,621,080 B2 | 9/2003 | Yamamoto | | |
| 6,734,425 B2 | 5/2004 | Hantschel et al. | | |
| 6,781,285 B1 | 8/2004 | Lazarus et al. | | |
| 6,903,491 B2 | 6/2005 | Irie et al. | | |
| 6,992,421 B2 | 1/2006 | Ikeda et al. | | |
| 7,055,378 B2 * | 6/2006 | Su | ......................... | B82Y 35/00 73/105 |
| 7,088,378 B1 | 6/2006 | Su et al. | | |
| 7,083,270 B2 | 8/2006 | Toni et al. | | |
| 7,084,554 B2 | 8/2006 | Xu et al. | | |
| 7,104,134 B2 | 9/2006 | Amano et al. | | |
| 7,195,909 B2 | 3/2007 | Klenerman et al. | | |
| 7,252,004 B2 | 8/2007 | Fink et al. | | |
| 7,263,874 B2 | 9/2007 | Fitch et al. | | |
| 7,458,265 B2 * | 12/2008 | Shih | ........................ | G01N 5/02 73/579 |
| 7,488,292 B2 | 2/2009 | Adachi | | |
| 7,497,133 B2 | 3/2009 | Shih et al. | | |
| 7,744,713 B2 | 6/2010 | Blessing | | |
| 7,744,773 B2 * | 6/2010 | Shih | ....................... | C04B 35/495 252/62.9 R |
| 7,779,707 B2 | 8/2010 | Shih et al. | | |
| 7,942,056 B2 * | 5/2011 | Mutharasan | .......... | G01H 11/08 73/579 |
| 7,992,431 B2 * | 8/2011 | Shih | ....................... | B82Y 35/00 73/105 |
| 8,033,185 B2 | 10/2011 | Shih et al. | | |
| 8,241,569 B2 | 8/2012 | Shih et al. | | |
| 9,743,991 B2 * | 8/2017 | Ludwin | ................. | A61B 90/03 |
| 2001/0037074 A1 | 11/2001 | Sarvazyan et al. | | |
| 2002/0094528 A1 | 7/2002 | Salafsky | | |
| 2002/0095087 A1 * | 7/2002 | Mourad | ................ | A61B 5/0048 600/442 |
| 2002/0117659 A1 | 8/2002 | Lieber et al. | | |
| 2002/0155303 A1 | 10/2002 | Wielstra et al. | | |
| 2003/0032293 A1 | 2/2003 | Kim et al. | | |
| 2003/0068655 A1 | 4/2003 | Bottomley et al. | | |
| 2003/0194697 A1 | 10/2003 | Klenerman et al. | | |
| 2003/0224551 A1 | 12/2003 | Kim et al. | | |
| 2003/0235681 A1 | 12/2003 | Sebastian et al. | | |
| 2004/0022677 A1 | 2/2004 | Wohlstadter et al. | | |
| 2004/0265664 A1 | 12/2004 | Badding et al. | | |
| 2005/0112621 A1 | 5/2005 | Kim et al. | | |
| 2005/0114045 A1 | 5/2005 | Giurgiutiu et al. | | |
| 2005/0199047 A1 | 9/2005 | Adams et al. | | |
| 2005/0252295 A1 | 11/2005 | Fink et al. | | |
| 2005/0277852 A1 | 12/2005 | Shih et al. | | |
| 2005/0287680 A1 | 12/2005 | Venkatasubbarao et al. | | |
| 2006/0053870 A1 | 3/2006 | Berndt | | |
| 2006/0079773 A1 * | 4/2006 | Mourad | ................. | A61B 5/031 600/438 |
| 2006/0217893 A1 | 9/2006 | Li et al. | | |
| 2006/0223691 A1 | 10/2006 | Shih et al. | | |
| 2006/0228657 A1 | 10/2006 | Masters et al. | | |
| 2006/0257286 A1 | 11/2006 | Adams | | |
| 2007/0089515 A1 | 4/2007 | Shih et al. | | |

(56) References Cited

U.S. PATENT DOCUMENTS

| | | | |
|---|---|---|---|
| 2007/0169553 | A1 | 4/2007 | Mutharasan |
| 2007/0141721 | A1 | 6/2007 | Vafai et al. |
| 2007/0218534 | A1 | 9/2007 | Klenerman et al. |
| 2008/0034840 | A1 | 2/2008 | Mutharasan |
| 2008/0035180 | A1 | 2/2008 | Mutharasan |
| 2009/0007645 | A1 | 1/2009 | Shih et al. |
| 2009/0053709 | A1 | 2/2009 | Mutharasan |
| 2009/0078023 | A1 | 3/2009 | Mutharasan |
| 2009/0145246 | A1 | 6/2009 | Shih et al. |
| 2009/0203000 | A1 | 8/2009 | Mutharasan |
| 2010/0068697 | A1 | 3/2010 | Shih et al. |
| 2010/0170342 | A1 | 7/2010 | Sinkus et al. |
| 2010/0224818 | A1 | 9/2010 | Shih et al. |
| 2010/0239463 | A1 | 9/2010 | Shih et al. |
| 2010/0281962 | A1 | 11/2010 | Shih et al. |
| 2011/0172565 | A1 | 7/2011 | Shih et al. |
| 2011/0265227 | A1 | 10/2011 | Shih et al. |
| 2012/0053489 | A1 | 3/2012 | Shih et al. |
| 2012/0065506 | A1* | 3/2012 | Smith ............... A61B 8/08 600/438 |
| 2012/0065507 | A1* | 3/2012 | Brunke ............... A61B 8/12 600/442 |

FOREIGN PATENT DOCUMENTS

| | | |
|---|---|---|
| CN | 101064197 A | 10/2007 |
| EP | 0631319 A1 | 12/1994 |
| EP | 1536227 A2 | 6/2005 |
| JP | 3093849 B2 | 4/2000 |
| JP | 2003-298131 A | 10/2003 |
| JP | 2004-265899 A | 9/2004 |
| JP | 2007-67125 A | 3/2007 |
| WO | 98/50773 A2 | 11/1998 |
| WO | 2004/061991 A1 | 7/2004 |
| WO | 2005/043126 A2 | 5/2005 |
| WO | 2006/031072 A1 | 3/2006 |
| WO | 2007/087328 A2 | 8/2007 |
| WO | WO 2007/109228 A1 | 9/2007 |
| WO | 2007/133619 A1 | 11/2007 |
| WO | 2008/020903 A2 | 2/2008 |
| WO | 2008/021187 A2 | 2/2008 |
| WO | 2008/021189 A2 | 2/2008 |
| WO | 2008/101199 A1 | 8/2008 |
| WO | 2009/014830 A1 | 1/2009 |
| WO | 2009/035732 A2 | 3/2009 |
| WO | 2009/035732 A3 | 3/2009 |
| WO | 2009/046251 A2 | 4/2009 |

OTHER PUBLICATIONS

Weng, L. et al., "Effect of acetylacetone on the preparation of PZT materials in sol/gel processing", Mater. Sci. Engin., B96: 307-312 (2002).
Wilson, L S et al., "Elastography—the movement begins", Phys. Med. Biol., 45: 1409-1421 (2000).
Wilson, L., et al., "Pezoelectric-excited millimeter-sized cantilever (PEMC) sensor provides viscosity and density measurements," Submitted to Review of Scientific Instruments, 1-26.
Yi, J. W. et al., "Effect of length, width, and mode on the mass detection sensitivity of piezoelectric unimorph cantilevers", J. Appl. Phys., 91(3): 1680-1686 (2002).
Yi, J. W. et al., "In situ cell detection using piezoelectric lead zirconate titanate-stainless steel cantilevers", J. Appl. Phys., 93(1): 619-625 (2003).
Zhao, Q. et al., "Array adsorbent-coated lead zirconate titanate (PZT)/stainless steel cantilevers for dimethyl methylphosphonate (DMMP) detection", Sensors and Actuators, B117(1): 74-79 (2006). Abstract Only.
Zhou, J. et al., "Zeolite-modified microcantilever gas sensor for indoor air quality control," Sensors and Actuators B, Oct. 1, 2003, 94(3), 337-342.

Zhu, D.M. et al., "Thermal conductivity and electromechanical property of single-crystal lead magnesium niobate titanate", Appl. Phys. Lett., 75(24): 3868-3870 (1999).
Data of Commercially Available Product, EDO Corporation: 1-8 (1999).
Data of Commercially Available Product, APC International, Ltd.: 1-2 (2005).
Campbell, G.A., et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).
Campbell, G.A., et al., "Method of measuring Bacillus anthracis spores in the Presence of copious amounts of Bacillus thurigiensis and Bacillus cereus," Anal. Chem. 79, 1145-1152 (2007).
Campbell, G.A., et al., "PEMC sensor's mass change sensitivity is 20 pg/Hz under liquid immersion," Biosensors and Bioelectronics, 22, 35-41 (2006).
Campbell, G.A., et al., "Detection of Bacillus anthracis spores and a model protein usings PEMC sensors in a flow cell at 1 mL/min," Biosensors and Bioelectronics, 22, 78-85 (2006).
Campbell, G.A., et al., "Detection of airborne Bacillus anthracis spores by an integrated system of an air sampler and a cantilever immunosensor," Sensors and Actuators B 127, 376-382 (2007).
Maraldo, et al., "Method for Label-Free Detection of Femtogram Quantities of Biologics in Flowing Liquid Samples," Anal. Chem. 79, 2762-2770 (2007).
Maraldo, et al., "Detection and confirmation of *Staphylococcal enterotoxin* B in apple juice and milk using piezoelectric-excited millimeter-sized cantilever sensors at 2.5 fg/mL," Anal Chem. 79, 7636-7643 (2007).
Maraldo, et al., "Method for Quantification of a Prostate Cancer Biomarker in Urine without Sample Preparation," Anal. Chem. 79, 7683-7690 (2007).
Maraldo, et al., "10-Minute assay for detecting *Escherichia coli* O157:H7 in ground beef samples using piezoelectric-excited millimeter-size cantilever sensors." Journal of Food Protection, vol. 70, No. 7, 1670-1677 (2007).
Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2655 (2007).
Rijal, et al., "PEMC-based method of measuring DNA hybridization at femtomolar concentration directly in human serum and in the presence of copious noncomplementary strands," Anal. Chem., 79, 7392-7400 (2007).
Rijal, et al., "Method for measuring the Self-Assembly of Alkanethiols on Gold at Femtomolar Concentrations," Langmuir, 23, 6856-6863 (2007).
Wilson, et al., "Viscosity and density values from excitation level response of piezoelectric-excited cantilever sensors," Sensors and Actuators A 138, 44-51 (2007).
Gu, et al., "Single-Calcination Synthesis of Pyrochlore-Free 0.9Pb (Mg1/3Nb2/3)03-0.1PbTiO3 and Pb(Mg1/3Nb2/3) O3 Ceramics using a Coating Method," J. Am. Ceram. Soc., 86 [2] 217-21 (2003).
Thaysen, et al., "Cantilever-Based Bio-Chemical Sensor Integrated in a Microliquid Handling System," 401-404 (2001).
Li, et al., Micromachined Biomimetic Sensor Using a Modular Artificial Hair Cells, pp. 1-3.
Thaysen, "Label free Detection, BioMEMs Materials and Fabrication Methods," Track 2, 3:00pm, pp. 1-3, Sep. 7, 2002.
Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39 (2005).
Campbell, G.A., et al., "Detection and quantification of proteins using self-excited PZT-glass millimeter-sized cantilever," Biosensors and Bioelectronics, 26-36 (Jan. 22, 2005).
Campbell, G.A., "Piezoelectric-excited millimeter-sized cantilever (PEMC) sensors detect Bacillus anthracis at 300 spores/mL," Biosensors and Bioelectronics, 37-45 (Sep. 19, 2005).

(56) References Cited

OTHER PUBLICATIONS

Campbell, G.A., et al., "kinetics of bacillus anthracis spore binding to antibody functionalized PEMC sensors in presence of bacillus thuringiensis and bacillus cereus," J. Publications, Am. Chem. Soc. 25 pages (Feb. 1, 2006).
Campbell, G.A., et al., "*Escherichia coli* O157:H7 detection limit of millimeter-sized PZT cantilever sensors in 700 cells/mL," Analytical Sci., 11-13 (Feb. 17, 2005).
Campbell, G.A., et al., "Detection of pathogen *Escherichia coli* O157:H7 using self-excited PZT-glass microcantilevers," Biosensors and Boelectronics, 14-25 (Aug. 25, 2004).
Campbell, G.A., "Detection of *Staphylococcus enterotoxin* B at pictogram levels using piezoelectric-excited millimeter-sized cantilever sensors," Submitted on line to J. of Analytical Chem., 1-24 (Mar. 29, 2006).
Campbell, G.A., et al., "Detect *Escherichia coli* O157:H7 in ground beef samples using piezoelectric excited millimeter-sized cantilever (PEMC) sensors," Submitted on-line to Biosensors and Bioelectronics, 2-34 (Mar. 5, 2006).
Campbell, G.A., et al., "A method for measuring *Escherichia coli* O157:H7 at 1 cell/mL in 1 liter sample using antibody functional piezoelectric-excited millimeter sized cantilever sensor," Paper submitted on-line to J. of Analytical Chemistry. 1-23 (2007).
Carr, D.W., et al., "Fabrication of nanoelectromechanical systems in single crystal silicon using silicon on insulator substrates and electron beam lithography," J. Vac. Sci. Technology, B, 5(6), 2760-2763 (Jun. 9, 1999).
Li, et al., Micromachined Biomimetic Sensor Using a Modular Artificial Hair Cells, pp. 1-3 (2007).
Luo, H. et al., "Synthesis of PMN and 65PMN-35PT Ceramics and Films by a New Suspension Method", Perovskite, Piezoelectric, and Dielectric Ceramics: 251-260 (2003).
Maraldo, D. et al., "Resonant-mode millimeter sized cantilever biosensor for continuous detection of proteins and pathogens in flowing liquids," Dept. of Chem. and Biological Eng., 1-21 (May 15, 2006).
Mazza, E. et al., Biomechanics, http://www.zfm.ethz.ch/e/res/bio/, 1-10 (Sep. 28, 2004).
Wang, Y. et al., "Tactile Mapping of Palpable Abnormalities for Breast Cancer Diagnosis" (1999).
Wellman, P. S. et al., "Tactile Imaging: A Method for Documenting Breast Lumps" (1999).
Wilson, L., et al., "Pezoelectric-excited millimeter-sized cantilever (PEMC) sensor provides viscosity and density measurements," Submitted to Review of Scientific Instruments, 1-26 (May 30, 2005).
Wellman, P. S. et al., "Breast Tissue Stiffness in Compression is Correlated to Histological Diagnosis", http://biorobotics.harvard.edu/pubs/mechprops: 1-15 (1999).
Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).
Ammari, H. et al., "T-Scan Electrical Impedance Imaging System for Anomaly Detection", Siam J. Appl. Math., 65(1): 252-266 (2004).
Baselt, D. R. et al., "Biosensor based on force microscope technology", J. Vac. Sci. Technol. B, 14(2): 789-793 (1996).
Birnie, III, D. P. et al., "Coating uniformity and device applicability of spin coated sol-gel PXT films", Microelectronic Engineering, 29: 189-192 (1995).
Bondoux, C. et al., "MgO insulating films prepared by sol-gel route for SiC substrate", J. Europe. Ceramic Soc., 25: 2795-2798 (2005).
Brito, R. et al., "Adsorption of 3-mercaptopropyltrimethoxysilane and 3-aminopropyltrimethoxysilane at platinum electrodes", J. Electroanalytical Chem., 520: 47-52 (2002).
Campbell, G.A., et al., "Detection and quantification of proteins using self-excited PZT-glass millimeter-sized cantilever,"Biosensors and Bioelectronics, 26-36 (Jan. 22, 2005).
Campbell, G.A., "Detection of *Staphylococcus enterotoxin* B at pictogram levels using piezoelectric-excited millimeter-sized cantilever sensors," Submitted on line to J. of Analytical Chem., 1-24.
Capobianco, J. A., et al., "Methyltrimethoxysilane—insulated piezoelectric microcantilevers for direct, all-electrical biodetection in buffered aqueous solutions", Rev. Sci. Instrum., 77: 125105-1-125105-6 (2006).
Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).
Carlier, S. G., et al., "Elastography", J. Cardiovasc Risk, 9(5): 237-245 (2002).
Che, G. et al., "Molecular recognition based on (3-mercaptopropyl) trimethoxysilane modified gold electrodes", J. Electroanalytical Chem., 417: 155-161 (1996).
Chen, G. Y. et al., "Adsorption-induced surface stress and its effects on resonance frequency of microcantilevers", J. Appl. Phys., 77(8): 3618-3622 (1995).
Chen, X. et al., "Electrochemical and Spectroscopic Characterization of Surface Sol-Gel Processes", Langmuir, 20 (20): 8762-8767 (2004).
Cho, S. H. et al., "Micro-scale metallization on flexible polyimide substrate by Cu electroplating using SU-8 photoresist mask", Thin Solid Films, 475: 68-71 (2005).
Duval, F.F.C. et al., "Stable TiO2/Pt electrode structure for lead containing ferroelectric thick films on silicon MEMS structures", Thin Solid Films, 444: 235-240 (2003).
Feili, D. et al., "Encapsulation of organic field effect transistors for flexible biomedical microimplants", Sensors and Actuators, A120: 101-109 (2005).
Ferrini, R. et al., "Screening Mammography for Breast Cancer: American College of Preventive Medicine Practice Policy Statement", www.acpm.org/breast, pp. 1-4 (2005).
Fritz, J. et al., "Translating Biomolecular Recognition into Nanomechanics", Science, 288: 316-318 (2000).
Fung, Y. S. et al., "Self-Assembled Monolayers as the Coating in a Quartz Piezoelectric Crystal Immunosensor to Detect *Salmonella* in Aqueous Solution", Anal. Chem., 73: 5302-5309 (2001).
Gao, L. et al., "Imaging of the elastic properties of tissue: A review", Ultrasound in Med. & Biol., 22(8): 959-977 (1996). Abstract Only.
Greenleaf, J. F. et al., "Selected Methods for Imaging Elastic Properties of Biological Tissues", Annu. Rev. Biomed. Eng., 5: 57-78 (2003).
Gu, H. et al., "Single-Calcination Synthesis of Pyrochlore-Free 0.9Pb(Mg1/3Nb2/3)O3-0.1PbTiO3 and Pb(Mg1/3Nb2/3)O3 Ceramics Using a Coating Method", J. Am. Ceram. Soc., 86(2): 217-221 (2003).
Haccart, T. et al., "Evaluation of niobium effects on the longitudinal piezoelectric coeffecients of Pb(Zr,Ti)O3 thin films", Appl. Phys. Lett., 76(22): 3292-3294 (2000).
Han, W. et al., "A magnetically driven oscillating probe microscope for operations in liquids", Appl. Phys. Lett., 69(26): 4111-4113 (1996).
Hiboux, S. et al., "Mixed titania-lead oxide seed layers for PZT growth on Pt(111): a study on nucleation, texture and properties", J. Europe. Ceram. Soc., 24: 1593-1596 (2004).
Hwang, I.H. et al., "Self-actuating biosensor using a piezoelectric cantilever and its optimization", Journal of Physics: Conference Series 34, pp. 362-367, 2006.
Hwang, K.S. et al., "In-situ quantitative analysis of a prostate-specific antigen (PSA) using a nanomechanical PZT cantilever", Lab Chip, 4: 547-552 (2004).
Ilic, B. et al., "Mechanical resonant immunospecific biological detector", Appl. Phys. Lett., 77(3): 450-452 (2000).
Itoh, T. et al., "Self-excited force-sensing microcantilevers with piezoelectric thin films for dynamic scanning force microscopy", Sensor and Actuators, A54:477-481 (1996).
Jung, S.K. et al., "Polymeric Mercaptosilane-Modified Platinum Electrodes for Elimination of Interferants in Glucose Biosensors", Anal. Chem., 68: 591-596 (1996).
Kanda, T. et al., "A flat type touch probe sensor using PZT thin film vibrator", Sensors and Actuators, 83: 67-75 (2000).

(56) References Cited

OTHER PUBLICATIONS

Katiyar, P. et al. "Electrical properties of amorphous aluminum oxide thin films", Acta Materialia, 53: 2617-2622 (2005).
Keller, A. et al., "Reliability of Computed Tomography Measurements of Paraspinal Muscle Cross-Sectional Area and Density in Patients With Chronic Low Back Pain", Spine, 28(13): 1455-1460 (2003).
Kelly, J. et al., "Effect of Composition on the Electromechanical Properties of (1-x)Pb(Mg1/3Nb2/3)O3—xPbTiO3 Ceramics" J. Am. Ceram. Soc., 80(4): 957-964 (1997).
Khabari, A. et al., "Partially ionized beam deposition of parylene" J. Non-Crystalline Solids, 351: 3536-3541 (2005).
Kim, S.H. et al., "Influence of Al2O3 diffusion barrier and PbTiO3 seed layer on microstructurel and ferroelectric charachteristics of PZT thin films by sol-gel spin coating method," Thin Solid Films, 305: 321-326 (1997).
Kim, S.J. et al., "Fabrication and Characterization of Pb(Zr,Ti)O3 Microcantilever for Resonance Sensors," Jpn. J. Appl. Phys., 42(3): 1475-1478 (2003).
Klissurska, R.D. et al. "Microstructure of PZT sol-gel films on Pt substrates with different adhesion layers," Microelectronic Engineering, 29: 297-300 (1995).
Kruse, S.A. et al., "Tissue characterization using magnetic resonance elastography: preliminary results," Phys. Med. Biol., 45: 1579-1590 (2000).
Kumar, V. et al., "A Simple System for the Preparation of Submicrometer Lead Titanate Powders by the Sol-Gel Method," J. Am. Ceram. Soc., 79(10): 2775-2778 (1996).
Kwok, CLK. et al., "Low temperature perovskite formation of lead zirconate titanate thin films by a seeding process," J. Mater. Res., 8(2): 339-344 (1993).
Chinese Office Action; dated Nov. 27, 2013 for corresponding CN Application No. 200980122516.0.
H. Zhang, et al., "A Sensitive and High-Throughput Assay to Detect Low-Abundance Proteins in Serum," Nature Medicine 12(4) 473-477 (2006).
J. W. Park, S. Kurosawa, H. Aizawa Y. Goda, M. Takai and K. Ishihara, "Piezoelectric Immunosensor for Bisphenol A Based on Signal Enhancing Step With 2-methacrolyloxyethyl Phosphorylcholine Polymeric Nanoparticle," Analyst, 131, 155-162 (2006).
A. M. Smith, G. Ruan, M. N. Rhyner, and S. Nie, "Engineering Luminescent Quantum Dots for in Vivo Molecular and Cellular Imaging," Ann. Biomed. Eng., 34 (1),3-14 (2006).
R. E. Jaeger and L. Egerton, "Hot-Pressing of Potassium-Sodium Niobates," J. Am. Ceram. Soc. 45, 209 (1962).
H. Birol, D. Damjanovic and N. Setter, "Preparation and Characterization of (K0.5Na0.5)NbO3 Ceramics", J. Eur. Ceram. Soc. 26, 861 (2006).
Y. Guo, K. Kakimoto, and H. Ohsato, "Phase Transitional Behavior and Piezoelectric Properties of (Na0.5K0.5)NbO3—LiNbO3 Ceramics," Appl. Phys. Lett., 85, 4121 (2004).
Y. Guo, K. Kakimoto, and H. Ohsato, "(Na0.5K0.5)NbO3—LiTaO3 Lead-free Piezoelectric Ceramics," Mater. Lett., 59, 241 (2005).
H. Li, W. Y. Shih, and W.-H. Shih, "Effect of Antimony Concentration on the Crystalline Structure, Dielectric and Piezoelectric Properties of (Na0.5K0,5)0.945Li0.055Nb1—xSbxO3 Solid Solutions", J. Am. Ceram. Soc., 90, 3070 (2007).
S. Zhang, R. Xia, T. R. Shrout, J. Zang, and J. Wang, "Piezoelectric Properties in Perovskite 0.948(K0.5Na0.5)NbO3—0.052LiSbO3 lead-free ceramics", J. App. Phys., 100, 104108 (2006).
X. Li, W. Y. Shih, J. S. Vartuli, D. L. Milius, L A. Aksay, and W.-H. Shih, "Effect of Transverse Tensile Stress on Electric-Field-Induced Domain Reorientation in Soft PZT: In Situ XRD Study", J. Am. Ceram. Soc. 85 (4), 844 (2002).
Q. Zhu, W. Y. Shih, and W.-H. Shih, "Real-Time, Label-Free, All-Electrical Detection of Salmonella typhimurium Using Lead Titanate Zirconate/Gold-Coated Glass Cantilevers at any Relative Humidity," Sensors and Actuators B, 125, 379-388 (2007).
Q. Zhu, W. Y. Shih, and W.-H. Shih, "Length and Thickness Dependence of Longitudinal Flexural Resonance Frequency Shifts of a Piezoelectric Microcantilever Sensor due to Young's Modulus Change," J. Appl. Phys. 104, 074503 (2008).
Q. Zhu, W. Y. Shih, and W.-H. Shih, "Enhanced Detection Resonance Frequency Shift of a Piezoelectric Microcantilever Sensor by a DC Bias Electric Field in Humidity Detection," Sensors and Actuators, B 138, 1 (2009).
Q. Zhu, W. Y. Shih, and W.-H. Shih, "Mechanism of the Flexural Resonance Frequency Shift of a Piezoelectric Microcantilever Sensor in a DC Bias Electric Field," Appl. Phys. Lett. 92, 033503 (2008).
Q. Zhu, Drexel University (2008).
McGovern, J.P. Drexel University (2008).
Luo, H.Y. Drexel University (2005).
Shin, S., Kim, J.P., Sim, S.J. & Lee, J. A multisized piezoelectric microcantilever biosensor array for the quantitative analysis of mass and surface stress. Applied Physics Letters 93, - (2008).
Pang, W. et al. Femtogram mass sensing platform based on lateral extensional mode piezoelectric resonator. Applied Physics Letters 88, -(2006).
Cherian, S. & Thundat, T. Determination of adsorption-induced variation in the spring constant of a microcantilever. Applied Physics Letters 80, 2219-2221 (2002).
Lee, J.H., Kim, T.S. & Yoon, K.H. Effect of mass and stress on resonant frequency shift of functionalized $Pb(Zr_{0.52}Ti_{0.48})O_3$ thin film microcantilever for the detection of C-reactive protein. Applied Physics Letters 84, 3187-3189 (2004).
Lee, J.H. et al. Immunoassay of prostate-specific antigen (PSA) using resonant frequency shift of piezoelectric nanomechanical microcantilever. Biosensors and Bioelectronics 20, 2157-2162 (2005).
Shen, Z., Shih, W.Y. & Shih, W.-H. Self-exciting, self-sensing $PbZr_{0.53}Ti_{0.47}O_3/SiO_2$ piezoelectric microcantilevers with femtogram/Hertz sensitivity. Applied Physics Letters 89, 023506-3 (2006).
Zhu, Q., Shih, W.Y. & Shih, W.-H. In situ, in-liquid, all-electrical detection of Salmonella typhimurium using lead titanate zirconate/gold-coated glass cantilevers at any dipping depth. Biosensors and Bioelectronics 22, 3132-3138 (2007).
McGovern, J.P. et al. Label-free flow-enhanced specific detection of Bacillus anthracis using a piezoelectric microcantilever sensor. Analyst 133, 649-654 (2008).
McGovern, J.P., Shih, W.Y. & Shih, W.H. In situ detection of Bacillus anthracis spores using fully submersible, self-exciting, self-sensing PMN-PT/Sn piezoelectric microcantilevers. Analyst 132, 777-783 (2007).
McGovern, J.-P, et al. Label-free flow-enhanced specific detection of Bacillus anthracis using a piezoelectric microcantilever sensor. The Analyst 133, 649-654 (2008).
McGovern, J.-P., Shih, W.Y. & Shih, W.-H. In situ detection of Bacillus anthracis spores using fully submersible, self-exciting, self-sensing PMN-PT/Sn piezoelectric microcantilevers. The Analyst 132, 777-783 (2007).
Zhu, Q., Shih, W.Y. & Shih, W.-H. Mechanism of flexural resonance frequency shift of a piezoelectric microcantilever sensor during humidity detection. Applied Physics Letters 92, 183505-3 (2008).
Su, W.-S., Chen, Y.-F., Shih, W.Y., Luo, H. & Shih, W.-H. Domain switching in lead magnesium niobate-lead titanate polycrystalline sheets at single grain level. Applied Physics Letters 91, 112903-3 (2007).
Shang, J.K. & Tan, X. Indentation-induced domain switching in Pb(Mg1/3Nb2/3)O3—PbTiO3crystal. Acta Materialia 49, 2993-2999 (2001).
Alguero, M., Jimenez, B. & Pardo, L. Rayleigh type behavior of the Young's modulus of unpoled ferroelectric ceramics and its dependence on temperature. Applied Physics Letters 83, 2641-2643 (2003).
Masys, A.J., Ren, W., Yang, G. & Mukherjee, B.K. Piezoelectric strain in lead zirconate titante ceramics as a function of electric field, frequency, and dc bias. Journal of Applied Physics 94, 1155-1162 (2003).
Capobianco, J.A., Shih, W.Y., Yuan, Q.-A., Adams, G.P. & Shih, W.-H. Label-free, all-electrical, in situ human epidermal growth receptor 2 detection. Review of Scientific Instruments 79, 076101 (2008).

(56) References Cited

OTHER PUBLICATIONS

Shih, W.Y., Luo, H., Li, H., Martorano, C. & Shih, W.-H. Sheet geometry enhanced giant piezoelectric coefficients. *Applied Physics Letters* 89, 242913-3 (2006).

Capobianco, J.A., Shih, W.Y. & Shih, W.-H. 3-mercaptopropyltrimethoxysilane as insulating coating and surface for protein immobilization for piezoelectric microcantilever sensors. *Review of Scientific Instruments* 78, 046106 (2007).

Morton, T.A., Myszka, D.G. & Chaiken, I.M. Interpreting Complex Binding—Kinetics from Optical Biosensors—a Comparison of Analysis by Linearization, the Integrated Rate-Equation, and Numerical-Integration. *Analytical Biochemistry* 227, 176-185 (1995).

Shuck, P. & Minton, A.P. Kinetic analysis of biosensor data: elementary test of self-consistency. *Trends Biochemical Sciences* 21, 458-460 (1996).

McKendry, R. et al. Multiple label-free biodetection and quantitative DNA-binding assays on a nanomechanical cantilever array. *Proceedings of the National Academy of Sciences of the United States of America* 99, 9783-9788 (2002).

Ndieyira, J.W. et al. Nanomechanical detection of antibiotic mucopeptide binding in a model for superbug drug resistance. *Nature Nanotechnology* 3, 691-696 (2008).

Sofian M. Kanan and Carl P. Tripp, "An Infrared Study of Adsorbed Organophosphonates on Silica: A Prefiltering Strategy for the Detection of Nerve Agents on Metal Oxide Sensors," Langmuir 2001, 17, 2213-2218, United States of America.

"Enhanced detection resonance frequency shift of a piezoelectric microcantilver sensor by a DC bias electric field in humidity detection," Sensors and Actuators B: Chemical, 2009, vol. 138, United States of America.

J. K. Shang and X. Tan, "Indentation-Induced Domain Switching in Pb(Mg1/3Nb2/3)03—PbTiO3 Crystal" Acta Mater., 2001, pp. 2993-2999, vol. 49, Urbana, Illinois.

IEEE Standard on Piezoelectricity IEEE, New York, 1988, Chap. 6.

L. Bellaiche and David Vanderbilt, Physical Review Letters, 83(7), Aug. 16, 1999, 1347.

S-F. Liu, W. Ren, B. K. Mukherjee, S. J. Zhang, T. R. Shrout, P. W. Rehrig, and W. S. Hackenberger, Appl. Phys. Lett., 83, 2886 (2003).

PZT data, IEEE Micro Electro Mechanical Systems Workshop, Jan.-Feb. 1991, Nara, Japan p. 118.

Xu, et al., "Longtitudinal piezoelectric coefficient measurement for bulk ceramics and thin films using pneumatic pressure rig," Journal of Applied Physics, Jul. 1, 1999, pp. 588-594, vol. 86, No. 1, Pennsylvania.

Li, "Sodium Potassium Niobate-based Lead-free Piezoelectric Ceramics: Bulk and Freestanding Thick Films," Thesis Submitted to Faculty of Drexel University, Jun. 2008, Philadelphia, Pennsylvania.

Li, "Synthesis of Na0.5K0.5NbO3 Piezoelectrics by a Solution Coating Approach," Int. J. Appl. Technol., 2009, pp. 205-215, vol. 6, Issue 2, United States of America.

Hudson, J.B. Surface Science: An Introduction, (Wiley-IEEE, New York, 1998).

Q. Thu. "Enhanced detection resonance frequency shift of a piezoelectric microcantilever sensor by a DC bias electric field in humidity detection," Sensors and Actuators B: Chemical, 2009, pp. 1-4, vol. 138.

Q. Thu, W. Y. Shih & W.H. Shih, "mechanism of flexural resonance frequency shift of a piezoelectric microcantilever sensor during humidity detection," Applied Physics Letters, 2008, vol. 92, United States of America.

Hudson, J.B. Surface Science: An Introduction, Wiley-IEEE, 1998, pp. 96-98, New York.

Leckband, D.E. et al. Force Probe Measurements of Antibody-Antigen Interactions. Methods 20, 329-340 (2000).

O'Sullivan, C.K. & Guilbault, G.G. Commercial quartz crystal microbalances—theory and applications. Biosensors & Bioelectronics 14, 663-670 (1999).

Lofgren, J.A. et al. Comparing ELISA and surface plasmon resonance for assessing clinical immunogenicity of panitumumab. J Immunol 178, 7467-72 (2007).

Borghaei, et al., "induction of Adaptive Anti-HER2/neu Immune Responses . . . " J. Immunother, Jun. 2007, pp. 455, vol. 30, No. 4.

H. Yengingil, "Breast Cancer Detection and Differentiation Using Piezoelectric Fingers," PhD Thesis, Drexel University, Philadelphia, PA, Jan. 2009.

E. E. Konofagou, T. Harrigan, and J. Ophir, "Shear Strain Estimation and Lesion Mobility Assessment in Elastography," Ultrasonics, 2000, pp. 400-404, vol. 38.

H.O. Yegingil, W. Y. Shih, W. Anjum, A. D. Brooks and W.-H. Shih, "Soft tissue elastic modulus measurement and tumor detection using piezoelectric fingers," Mat. Res. Soc. Symp. Proc., 2006, vol. 898E.

P. S. Wellman, E. P. Dalton,, D. Krag,, K. A. Kern, R. D. Howe, "Tactile Imaging of Breast Masses: First Clinical Report," Archives of Surgery 136(2), 204-08 (2001).

Z. Shen, W. Y. Shih, and W.-H. Shih, "Mass detection sensitivity of piezoelectric cantilevers with a nonpiezoelectric extension," Rev. Sci. Instrum. 77, 065101 (2006).

A. Markidou, W. Y. Shih, and W.-H. Shih, "Soft-materials elastic and sear moduli measurement using piezoelectric cantilevers," Rev. Sci. Ins. 76, 064302 (2005).

S . T. Szewczyk, W.Y. Shih, and W.-H. Shih, "Palpationlike soft-material elastic modulus measurement using piezoelectric cantilievers," Rev. Sci. Ins., 77, 044302 (2006).

H. O. Yegingil, W. Y. Shih, and W.-H. Shih, "All-electrical indentation shear modulus and elastic modulus measurement using a piezoelectric cantilever with a tip," J. Appl. Phys., 101, 054510 (2007).

W. Jiang and W. Cao, "Intrinsic and coupling-induced elastic nonlinearity of lanthanum-doped lead magnesium niobate-lead titanate electrostrictive ceramic," Appl. Phys. Lett., 77,1387 (2000).

A. W. McFarland, et al., "Influence of surface stress on the resonance behavior of microcantilevers," Appl. Phys. Lett. 87, 053505 (2005).

O. Kwon, "T-scan Electrical Impedance Imaging system for anomaly detection," SIAM J. Appl. Math., 2004, pp. 252-266, vol. 65, No. 1.

Sure Touch Exam [online] retrieved Nov. 29, 2010 from the internet @ http://www.medicaltactile.com/default.htm.

Q. Ren and Y. P. Zhao, "Influence of surface stress on frequency of microcantilever-based biosensors," Microsystem Technologies, 2004, pp. 307-314, vol. 10.

E. Chen, "Ultrasound Tissue Displacement and Tissue Elasticity Imaging," Ph.D. dissertation, University of Illinois at Urbana-Champaign, (1995).

Haun, M.J. "Thermodynamic Theory of the Lead Zirconate-Titanate Solid Solution System," The Pennsylvania State University (1988).

Chinese Office Action; dated Dec. 19, 2014 for corresponding CN Application No. 200980122516.0.

Lee, C. et al., "Sol-gel derived PZT force sensor for scanning force microscopy", Mater. Chem. Phys., 44: 25-29 (1996).

Lee, C. et al., "Self-excited piezoelectric PZT microcantilevers for dynamic SFM—with inherent sensing and actuating capabilities", Sensors and Actuators, A72: 179-188 (1999).

Lee, J. H. et al., "Label free novel electrical detection using micromachined PZT monolithic thin film cantilever for the detection of C-reactive protein", Biosensors and Bioelectronics, 20: 269-275 (2004).

Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).

Lee, J. H. et al., "Immunoassay of prostate-specific antigen (PSA) using resonant frequency shift of piezoelectric nanomechanical microcantilever", Biosensors and Bioelectronics, 20: 2157-2162 (2005).

Lee, S. S. et al., "Self-Excited Piezoelectric Cantilever Oscillators", The 8th International Conference on Solid-State Sensors and Actuators, and Eurosensors IX, Stockholm, Sweden: 417-420 (1995).

Lee, Y. et al., "A Piezoelectric Micro-Cantilever Bio-Sensor Using the Mass-Microbalancing Technique With Self-Excitation", The

(56) References Cited

OTHER PUBLICATIONS

13th International Conference on Solid-State Sensors, Actuators, and Microsystems, Seoul, Korea: 644-647 (2005).
Li, S. et al., "The intrinsic nature of nonlinear behavior observed in lead zirconate titanate ferroelectric ceramic", J. Appl. Phys., 69(10): 7219-7224 (1991).
Li, X. et al., "Detection of water-ice transition using a lead zirconate titanate/brass transducer", J. Appl. Phys., 92(1): 106-111 (2002).
Lin, Z. et al., "Operation of an Ultrasensitive 30-MHz Quartz Crystal Microbalance in Liquids", Anal. Chem., 65(11): 1546-1551 (1993).
Liu, W. et al., "Preparation and orientation control of Pb1.1(Zr0.3Ti0.7)O3 thin films by a modified sol-gel process", Mat. Lett., 46: 239-243 (2000).
Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).
Luo, H., "Colloidal Processing of PMN-PT Thick Films for Piezoelectric Sensor Applications", A Thesis Submitted to the Faculty of Drexel University in Jun. 2005.
Maki, K. et al., "Evaluation of Pb(Kr,Ti)O3 Films Derived from Propylene-Glycol-Based Sol-Gel Solutions", Jpn. J. Appl. Phys., 39(96): 5421-5425 (2000).
Matsui, Y. et al., "Highly Oxidation-Resistant TiN Barrier Layers for Ferroelectric Capacitors", Jpn. J. Appl. Phys., 36 (3B): 1586-1588 (1997).
McGovern, J.P. et al., "Real-Time *Salmonella* Detection Using Lead Zirconate Titanate-Titanium Microcantilevers", Mater. Res. Soc. Symp. Proc., 845: AA3.8.1-AA3.8.6 (2005).
Mueller, V. et al., "Nonlinearity and scaling behavior in donor-doped lead zirconate titanate piezoceramic", Appl. Phys. Lett., 72(21): 2692-2694 (1998).
Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).
Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).
Nguyen, L. T. T. et al., "Synthesis and characterization of a photosensitive polyimide precursor and its photocuring behavior for lithography applications", Optical Materials, 29: 610-618 (2007).
Oden, P. I. et al., "Viscous drag measurements utilizing microfabricated cantilevers", Appl. Phys. Lett., 68(26): 3814-3816 (1996).
Ohnmacht, M. et al., "Microcoils and microrelays—an optimized multilayer fabrication process", Sensors and Actuators, 83: 124-129 (2000).
Park, G.T. et al., "Measurement of piezoelectric coefficients of lead zirconate titanate thin films by strain-monitoring pneumatic loading method", Appl. Phys. Lett., 80(24): 4606-4608 (2002).
Park, S.E. et al., "Ultrahigh strain and piezoelectric behavior in relaxor based ferroelectric single crystals", J. Appl. Phys., 82(4): 1804-1811 (1997).
Piezo Systems, Inc., "Piezoceraminc Sheets and Their Properties", Piezo Systems, Inc. Catalog: 1-3 (2007).
Pons, T. et al., "Solution-phase single quantum dot fluorescence resonance energy transfer", J. Amer. Chem. Soc., 128(47): 15324-15331 (2006). Abstract Only.
Ren, W. et al., "Non linear strain and DC bias induced piezoelectric behaviour of electrostrictive lead magnesium niobate-lead titanate ceramics under high electric fields", J. Phys. D: Appl. Phys., 35: 1550-1554 (2002).
Ren, W. et al., "Nonlinear behavior of piezoelectric lead zinc niobate-lead titanate single crystals under ac electric fields and dc bias", Appl. Phys. Lett., 83(25): 5268-5270 (2003).
Rosenberg, RD et al., "Effects of age, breast density, ethnicity and estrogen replacement therapy on screening mammographic sensitivity and cancer stage at diagnosis: review of 183, 134 screening mammograms in Albuquerque, New Mexico", Radiology, 209(2): 511-5118 (1998). Abstract Only.
Saito, Y. et al., "Lead-free piezoceramics", Nature, 432: 84-87 (2004).
Schemmel, A. et al., "Single molecule force spectrometer with magnetic force control and inductive detection", Rev. Sci. Instrum., 70(2): 1313-1317 (1999).
Shen, Z. et al., "Microfabrication of Miniaturized PZT/SiO2 Piezoelectric Microcantilever for Rapid, Direct, in-situ Biosensing", MRS Fall Meeting, Boston: 1-23 (2005).
Shen, Z. et al., "Self-exciting, self-sensing PbZr0.53Ti0.4703/SiO2 piezoelectric microcantilevers with femtogram/Hertz sensitivity", Appl. Phys. Lett., 89: 023506-1-023506-3 (2006).
Shih, W. et al., "Simultaneous liquid viscosity and density determination with piezoelectric unimorph cantilevers", J. Appl. Phys., 89(2): 1497-1505 (2001).
Shih, W. et al., "Ultrasensitive Pathogen Quantification in Drinking Water Using Highly Piezoelectric Microcantilevers", Amer. Chem. Soc., Chapter 23, 179-185 (2005).
Shih, W. et al., "Nanosensors for Environmental Applications", Nanotechnologies for the Life Sciences, 5: 271-293 (2005).
Straub, V. et al., "Contrast Agent-Enhanced Magnetic Resonance Imaging of Skeletal Muscle Damage in Animal Models of Muscular Dystrophy", Magn. Reson. Med., 44: 655-659 (2000).
Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).
Thundat, T. et al., "Detection of mercury vapor using resonating microcantilevers", Appl. Phys. Lett., 66(13): 1695-1697 (1995).
Tslonsky, M. et al., "Sol-Gel-Derived Ceramic-Carbon Composite Electrodes: Introduction and Scope of Applications", Anal. Chem., 66: 1747-1753 (1994).
Tu, Y. L. et al., "A study of the effects of process variables on the properties of PZT films produced by a single-layer sol-gel technique", J. Mater. Sci., 30: 2507-2516 (1995).
Udayakumar, K. R. et al., "Thickness-dependent electrical characteristics of lead zirconate titanate thin films", J. Appl. Phys., 77(8): 3981-3986 (1995).
Wang, Q.M. et al., "Nonlinear piezoelectric behavior of ceramic bending mode actuators under strong electric fields", J. Appl. Phys., 86(6): 3352-3360 (1999).
Ward, M. D. et al., "In Situ Interfacial Mass Detection with Piezoelectric Transducers", Science, 249: 1000-1007 (1990).
Wellman, P. S. et al., "Tactile Imaging of Breast Masses", Arch. Surg., 136: 204-208 (2001).
Chinese Office Action; dated Jul. 17, 2017 for CN Application No. CN 201510391245.6.
European Office Action; dated Sep. 15, 2017 for EP Application No. EP09747741.8.

\* cited by examiner

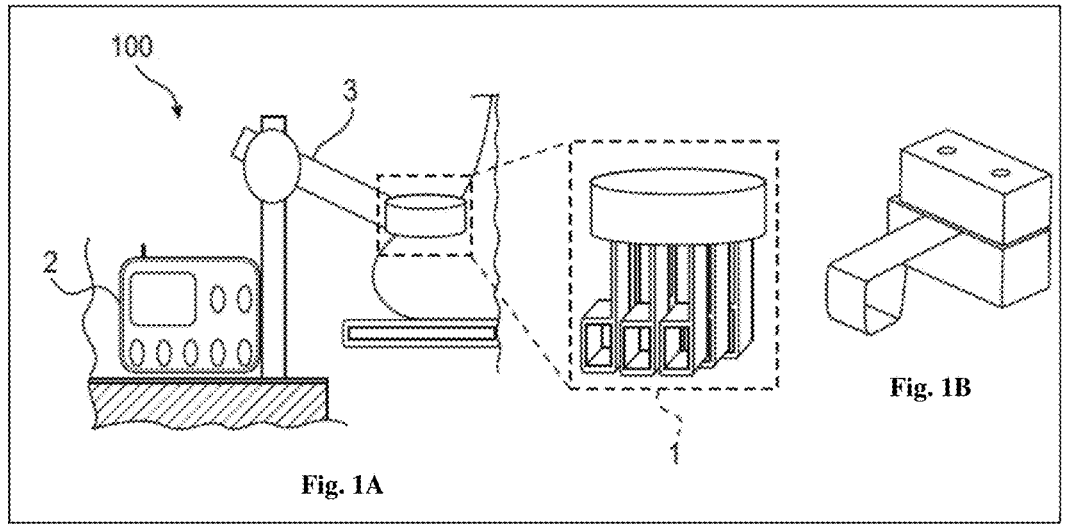
Fig. 1A
Fig. 1B
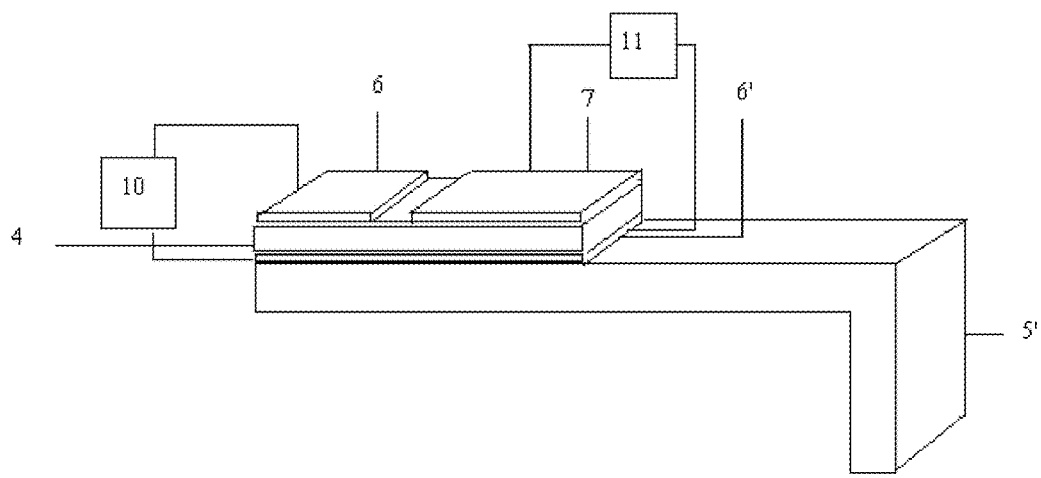
Figure 2A

Figure 3
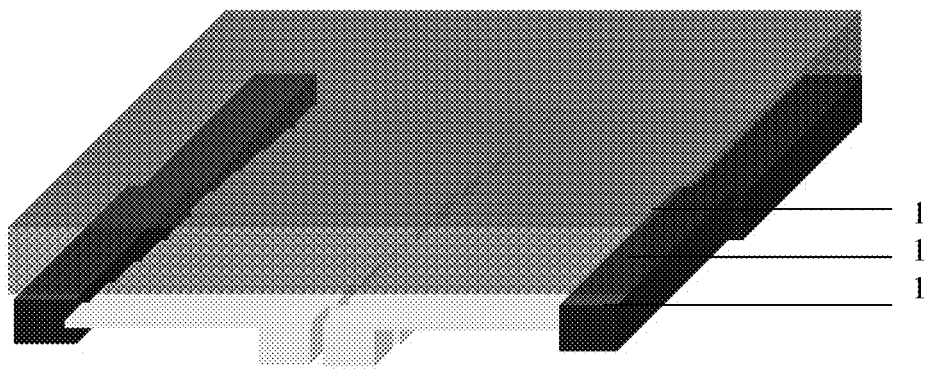
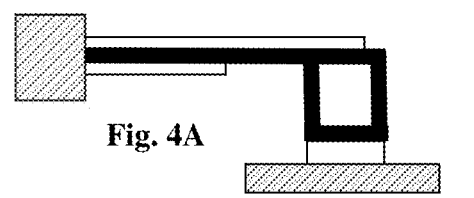
Fig. 4A
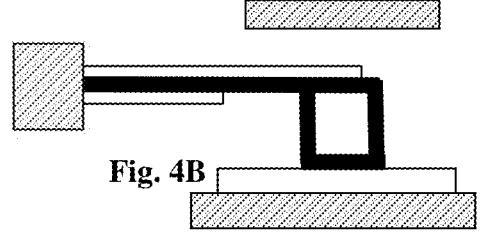
Fig. 4B
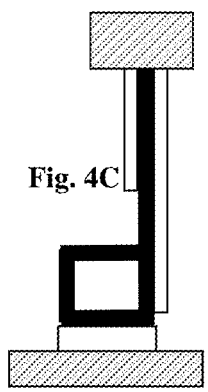
Fig. 4C
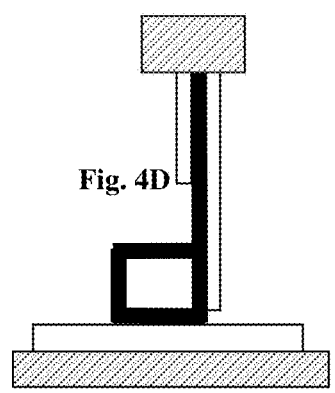
Fig. 4D

Elastic Modulus Scan

X Distance (mm)

Elastic Modulus Scan

Shear Modulus Scan

G / E Ratio

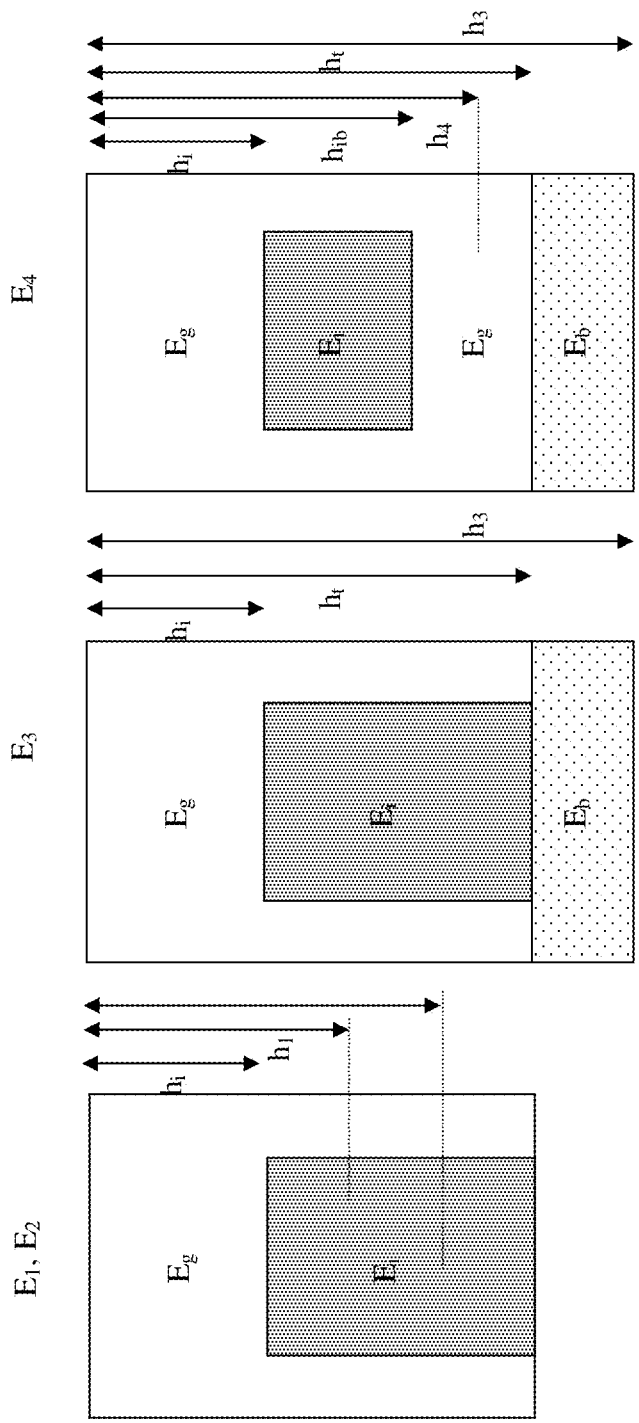

SYSTEM AND METHOD FOR EVALUATING TISSUE

CROSS-REFERENCE TO RELATED APPLICATIONS

This application claims priority to U.S. Non-Provisional patent application Ser. No. 14/031,307, filed Sep. 19, 2013; currently pending; which is a division of U.S. patent application Ser. No. 12/992,923, filed on Mar. 8, 2011, U.S. Pat. No. 8,562,546 issued Oct. 22, 2013, which is a 371 of International application PCT/US2009/044250 filed May 15, 2009; and is a non-provisional of U.S. Provisional Patent Application No. 61/054,100, filed on May 16, 2008, pursuant 35 U.S.C. 119(e), the entire disclosure of which is incorporated herein by reference.

STATEMENT OF GOVERNMENT INTEREST

This invention was reduced to practice with Government support under Grant No. RO1 EB000720 awarded by the National Institutes of Health; the Government is therefore entitled to certain rights to this invention.

BACKGROUND OF THE INVENTION

Field of Invention

The present invention relates to a system and method for quantitatively evaluating a tumor. More particularly, the invention involves using a piezoelectric sensor to detect the existence of, determine the dimensions of, determine the location of, identify the type of, determine the invasiveness of and/or determine the malignancy of a tumor.

Brief Description of the Prior Art

The key to successful treatment of cancer lies in early detection; in turn, the early detection and identification of cancerous growths is heavily dependent upon the capability of sensors and screening technologies. Currently, there are a variety of different sensors and tools used for investigating the mechanical properties of soft tissue and for imaging soft tissue.

One type of conventional soft tissue sensor uses an external force applicator for inducing displacement and an external displacement gauge for measuring resistive force.[1,2] The external force applicator may be hydraulic or piezoelectric, and the external displacement gauge may be optical or piezoelectric. These sensors, however, require the extraction and destruction of tissue specimens; during operation, since the specimens must be cut to conform with and fit within the sensor.

Exemplary soft tissue imaging tools include Computer Tomography (CT), Magnetic Resonance Imaging (MRI), Ultrasound (US), T-scan (TS) and Ultrasound elastography (UE).[3-8] CT scans[10] take 360 degree X-ray pictures and reconstructs 3D tissue structures using computer software. MRI scans[11] use powerful magnetic fields and radio waves to create tissue images for diagnosis. US scans[12] transmit high-frequency waves through tissue and capture the echoes to image tissue structures. TS[7] measures low-level bioelectric currents to produce real-time images of electrical impedance properties of tissues. UE scans[14] evaluate the echo time through tissue under a constant mechanical stress and compares it to that of the same tissue when unstressed. A tissue strain map is then obtained, from which an image of 2D elastic modulus distribution is created by conventional inversion techniques.

Tactile imaging[12] tools, such as mammography, use array pressure sensors to probe spatial tissue stiffness variations. Currently, mammography is used in breast cancer screening to detect abnormal tissue by tissue density contrast. Mammography is the only FDA approved breast cancer screening technique, which has a typical sensitivity of 85% that decreases to 65% in radiodense breasts.[9] However, in these screening processes there is a high incidence of false positives. In fact, only about 15-30% of breast biopsies yield a diagnosis of malignancy. Although effective for screening women over 40, mammography is not as effective for screening women who have dense breast tissue. Additionally, mammography and other tactile imaging tools do not have the ability to probe tumor interface properties.

Since many tissues harboring abnormal growths are stiffer than the surrounding normal tissues under compression, detecting a change in tissue stiffness has increasingly become an important factor in detection and diagnosis of abnormal tissue. For example, breast cancers are calcified tissues that are known to be more than seven times stiffer than normal breast tissue.[10-13] Similarly, plaque-lined blood vessels are also stiffer than normal, healthy blood vessels.

U.S. Pat. No. 7,497,133 discloses a piezoelectric finger sensor that may be used to detect tumors by measuring tissue stiffness. Tumor mobility was assessed from the ratio of the shear modulus to the elastic modulus (G/E) ratio of the tumor or by sensitive direct tumor mobility measurement using two piezoelectric finger sensors, one for pushing and one for measuring the movement of the tumor that results from the pushing. The patent concludes that the G/E ratio is higher in a tumor region than the G/E ratio for surrounding normal tissue and that a much higher G/E ratio in the cancer region indicated that the tumor was less mobile under shear than under compression, as compared to the surrounding normal tissue. Although the patent concludes that these measurements may offer the potential for non-invasive breast cancer malignancy screening, it does not disclose a method for determining malignancy, invasiveness or tumor type.

Consequently, there remains an important need to accurately and non-invasively detect and identify tumors. Moreover, there exists a need to develop a means for probing tumor stiffness to determine the type, malignancy and/or invasiveness of the tumor.

SUMMARY OF THE INVENTION

In a first aspect, the invention relates to a sensor system for measuring an elastic modulus and a shear modulus comprising a sensor, an apparatus for applying a voltage to a second electrode, a measuring means connected to said sensor; and a positioning means which may be automated or manual for positioning said sensor.

In another aspect, the invention pertains to a method for evaluating a tissue. The method involves applying a set of forces of different magnitudes to one or more locations of tissue, detecting the corresponding displacements due to said applied forces, determining the forces acting on those locations of tissue which are a combination of forces from the applied voltages and the countering forces from tissue deformation, obtaining the elastic modulus and/or shear modulus for a plurality of locations, and determining abnormal growth invasiveness, malignancy or the presence of a tumor from said elastic and/or shear moduli.

In another aspect, the present invention provides the ability to measure the dimensions and/or position of abnormal tissue in a tissue sample. The dimensions and/or position of abnormal tissue may be determined by measuring the elastic modulus and thickness of the tissue sample using a PEFS array having a plurality of PEFS' of different widths, i.e. tissue contact regions. By measuring the elastic modulus of the tissue sample using PEFS' of different widths, and consequently different depth sensitivities, the elastic modulus and thickness of the abnormal tissue and the elastic modulus of the surrounding tissue can be calculated. From these calculations, the dimensions of the abnormal tissue as well as the depth and position of the of the abnormal tissue within the tissue sample can be determined.

BRIEF DESCRIPTION OF THE DRAWINGS

FIG. 1(a) is a schematic of a PEFS system including at least one PEFS, a measuring means and an automated sensor positioning means.

FIG. 1(b) is a photograph of a PEFS.

FIG. 2(a) is a schematic of a PZT/stainless steel cantilever with driving electrode and a sensing electrode on a top side of the piezoelectric layer.

FIG. 3 is a schematic of a PEFS array.

FIG. 4(a) is a schematic of a PEFS being used for standard compression measurement to determine elastic modulus.

FIG. 4(b) is a schematic of a PEFS being used for indentation compression measurement to determine elastic modulus.

FIG. 4(c) is a schematic of a PEFS being used for standard shear measurement to determine shear modulus.

FIG. 4(d) is a schematic of a PEFS being used for indentation shear measurement.

FIG. 29(a) is a diagram illustrating a tissue sample probed with 2 PEFS to determine the depth of abnormal tissue in a breast tissue sample.

FIG. 29(b) is a diagram illustrating a tissue sample that needs to be probed with 3 PEFS ($E_1$, $E_2$, and $E_3$) to determine the depth of abnormal tissue attached to the base of the breast.

FIG. 29(c) is a diagram illustrating a tissue sample that needs to be probed with 4 PEFS ($E_1$, $E_2$, $E_3$, and $E_4$) to determine the depth of abnormal tissue suspended within the breast.

DETAILED DESCRIPTION OF THE PREFERRED EMBODIMENT(S)

Figure 2B:
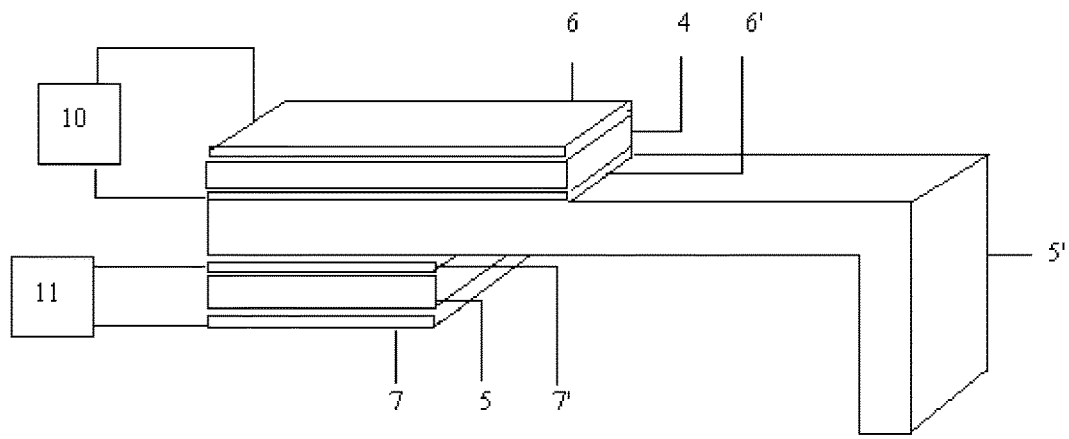
FIG. 2(b) is a schematic of a PZT/stainless steel cantilever with a driving PZT layer and a sensing PZT layer and an L-shaped cantilever.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. Thus, for example, reference to "a sensor" includes a plurality of sensors and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The present invention is directed to a system and method for evaluating tissue, specifically soft tissue, to detect and/or identify an abnormal growth using a piezoelectric finger sensor (PEFS) system 100. The PEFS system may include at least one PEFS 1, a measuring means 2 and an automated sensor positioning means 3. In an exemplary embodiment, PEFS 1 may include both an actuator and sensor capable of being simultaneously operated using a simple all electrical means.

In accordance with the method of the present invention, PEFS 1 may be used in vivo to measure elastic and shear properties of tissue. By quantitatively determining the shear modulus, elastic modulus and/or the ratio of shear modulus to elastic modulus (hereinafter referred to as the "G/E ratio") of the tissue, PEFS 1 may be used to determine the existence, dimension, location, type, invasiveness and/or malignancy of a tumor contained within the tissue. The method of the present invention may be used to detect, screen for, diagnose and/or confirm the presence of various different forms of cancerous tissue and may be particularly suitable for detecting breast cancer, prostate cancer, skin cancer or liver cancer.

1. Piezoelectric Finger Sensor (PEFS) System

As shown in FIG. 1, the PEFS system 100 of the present invention may include at least one PEFS 1 attached to a measuring means 2 for generating an image, graphical or numerical representation of the spatial distribution of the elastic modulus, shear modulus and/or the G/E ratio of tissue. In an exemplary embodiment, the PEFS system may further include an automated or manual sensor positioning means 3 that is attached to and capable of positioning PEFS 1 relative to a tissue surface.

The at least one PEFS 1 of the present invention may be constructed as a cantilever, including at least one piezoelectric layer 4 bonded to at least one non-piezoelectric layer 5 and including at least one conductive element 6, 7 for applying a voltage to and relaying an induced voltage from at least one piezoelectric layer 4.

Figure 2C:
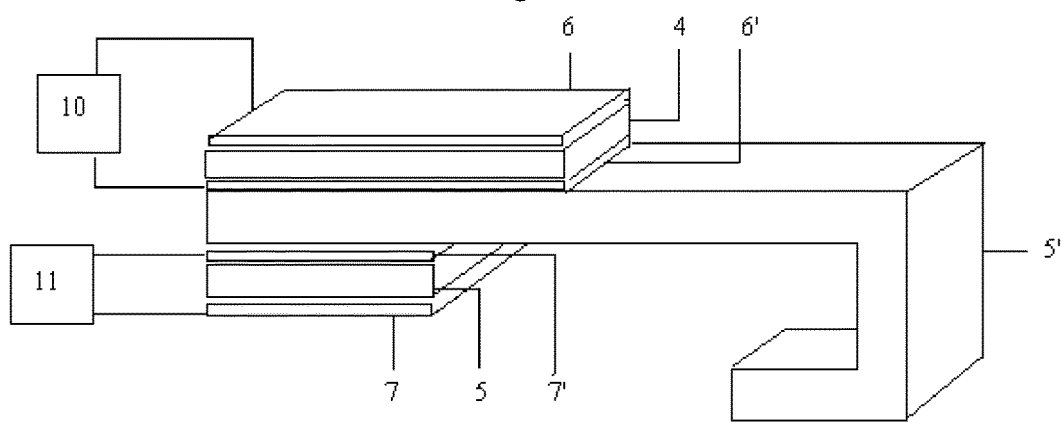
FIG. 2(c) is a schematic of a PZT/stainless steel cantilever with a driving PZT layer and a sensing PZT layer and a U-shaped cantilever.
Figure 2D:
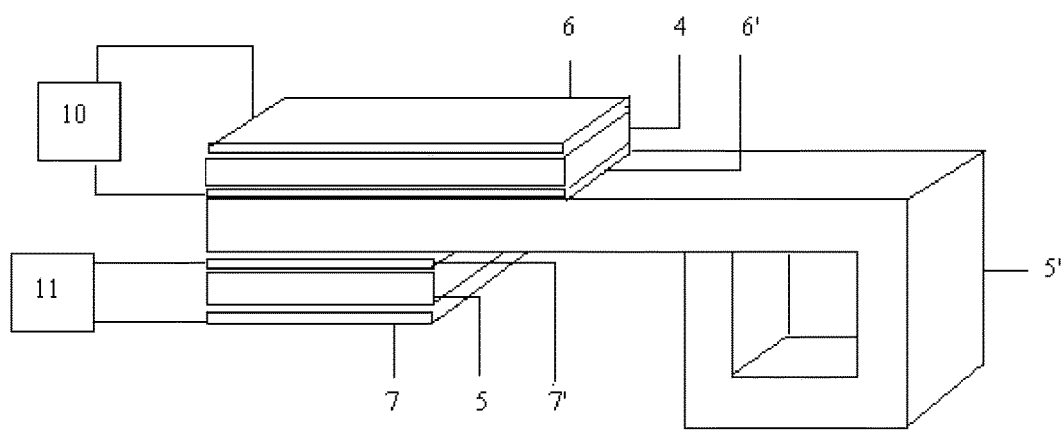
FIG. 2(d) is a schematic of a PZT/stainless steel cantilever with a driving PZT layer and a sensing PZT layer and a square-shaped cantilever.

FIG. 2(a) shows one embodiment in which a driving electrode 6 and a sensing electrode 7 are attached to the same side of piezoelectric layer 4. A third electrode 6' may be positioned on an opposite side of piezoelectric layer 4. FIGS. 2(b)-2(d) show another embodiment including a first piezoelectric layer 4 with electrodes 6, 6' on opposing surfaces for driving PEFS 1, a non-piezoelectric layer and a second piezoelectric layer 5' with electrodes 7, 7' on opposing surfaces for sensing a displacement of PEFS 1. To facilitate simultaneous force application and displacement measurement, the present piezoelectric cantilever sensor may be constructed as a two circuit system. A first circuit may be used to apply a driving force to PEFS 1. In an exemplary embodiment, the force application circuit may contain a power supply 10 connected to electrodes 6 and 6' in a first embodiment shown in FIG. 2(*a*). Alternatively, the power supply 10 may be connected to electrodes 6 and 6' across the first piezoelectric layer 4 in a second embodiment shown in FIGS. 2(*b*)-2(*d*). A second circuit may be used to sense and quantitatively measure the displacement of the PEFS 1 that results from the applied driving force. In an exemplary embodiment, the voltage measurement circuit may contain a voltage measuring device 11 connected to electrode 7 and 6', as shown in the first embodiment shown in FIG. 2(*a*). Alternatively, voltage measuring device 11 may be connected to electrodes 7 and 7' across the second piezoelectric layer 5' in the second embodiment shown in FIGS. 2(*b*)-2(*d*).

PEFS 1 may operate without sensing electrode 7 in the embodiment shown in FIG. 2(*a*) or without the second piezoelectric layer 5' and electrodes 7 and 7' in the embodiment shown in FIGS. 2(*b*)-2(*d*). These components may be replaced with other means for measuring displacement of the piezoelectric cantilever under compression or shear, such as a laser or a piezoelectric displacement meter. However, without the self-sensing capability provided by electrode 7 in the first embodiment or the second piezoelectric layer 5' and electrodes 7 and 7' in the second embodiment, the device would not be capable of in vivo or in situ measurements of tissues having complex shapes.

PEFS 1 may have a variety of different shapes and configurations that facilitate tissue analysis. Exemplary configurations may include an L-shaped, U-L-shaped, U-shaped, square-shaped, rectangle-shaped, O-shaped or tapered structure having various lengths and widths. In an exemplary embodiment, PEFS 1 may have an L-shaped tip adapted to accurately measure the shear modulus of soft tissues and materials under a negligible degree of strain of less than about 0.1% so as to avoid any patient discomfort. Preferably, PEFS 1 is constructed as a small cantilever probe having one or more cantilevered fingers suitable for detecting prostate cancer, breast cancer, skin cancer or liver cancer.

In an exemplary embodiment, PEFS 1 is a cantilever all-electrical sensor capable of simultaneously applying a force to tissue and detecting the corresponding induced displacement of the tissue. This ability to self-excite and self-detect enables PEFS 1 to directly measure the elastic and shear moduli of specimens having complex shapes using its cantilevered tip. In operation, the tip of the PEFS 1 cantilever is positioned adjacent to and/or in contact with a tissue surface. A voltage is then applied to driving electrode 6 of piezoelectric layer 4 in order to generate a bending force that induces a corresponding displacement of PEFS 1. When the sensor tip is in contact with the tissue, the displacement of cantilever will be altered by the resistance of the tissue, with stiffer tissue producing less bending. The net force acting on the tissue is therefore the combination of the force generated by the applied voltage and the countering force resisting tissue deformation. Bending of the PEFS 1 cantilever generates an induced piezoelectric voltage in the bottom sensing PZT layer in proportion to the displacement at the cantilever tip. The displacement of the cantilever tip may be measured by detecting the induced piezoelectric voltage from sensing electrode 7. Carefully monitoring the displacement at the cantilever tip during a given test provides an accurate measurement of the force exerted on and the resulting displacement of a tissue surface. This information may then be used to accurately determine the mechanical properties of the tissue sample. For example, the slope of the net force versus displacement plot, may be used to determine the elastic modulus, shear modulus or G/E ratio of the tissue. PEFS 1 may have a high degree of detection sensitivity. In an exemplary embodiment, PEFS 1 may have a depth detection sensitivity that is about twice the width of PEFS 1. For example, a 1 cm wide PEFS 1 may be capable of measuring, detecting and analyzing tissue up to a depth of about 2 cm.

In an exemplary embodiment, PEFS system 100 may include several PEFS 1 arranged in an array to facilitate real-time compression and shear measurement. PEFS arrays of varying probe widths or identical probe widths ranging from less than 1 millimeter to several centimeters may be constructed to assess stiffness variations of soft materials/tissues up to tens of centimeters in depth with increased spatial resolution of less than one-millimeter. The depth sensitivity may be further enhanced and customized by adjusting the width of the PEFS contact area. The preferred PEFS width may range from 1-15 mm to provide adequate measurement speeds.

The PEFS array may have any configuration and dimension; preferably, the array may have a contact surface of about 5 to 10 cm in diameter. The array may be formed from PEFS of any dimension. In an exemplary embodiment, the PEFS array may be fabricated from PEFS with a contact area of about 0.1×0.1 mm to about 10×10 mm. The PEFS may have a dimension of about 1-10 mm wide by about 1-3 cm long. As shown in the exemplary embodiment of FIG. 3, each PEFS may be provided with a long driving PZT layer on one side of a stainless steel sham and a shorter sensing PZT layer on the other side of the stainless steel sham. The PEFS's of the array may all be oriented perpendicular to a tissue surface, as depicted in FIGS. 4(*c*)-4(*d*), for measuring the shear modulus. Alternatively, the PEFS's of the array may be oriented parallel with a tissue surface, as depicted in FIGS. 4(*a*)-4(*b*), for measuring the elastic modulus.

The PEFS array may include a plurality of PEFS of uniform or varying dimensions, forming a tissue contact surface of suitable dimensions. The PEFS array may be fabricated by cutting previously bonded PZT/stainless steel bi-layer or PZT/stainless steel/PZT multi-layer into parallel PEFS using a diamond-saw or wire-saw cutter. These individual PEFS 1 may then be arranged and assembled in an array, as shown in FIG. 3. In an exemplary embodiment, the array may be customized to correspond to the contours and dimensions of a particular tissue surface.

Moreover, in addition to facilitating the detection process, the PEFS array increases depth sensitivity. The depth detection sensitivity of an array of PEFS 1 may be about twice the combined width of the PEFS 1 of the array. Arranging several PEFS in an array and synchronizing the measurements of neighboring PEFS 1 induces multiple PEFS' 1 to behave as a single sensor having a wide contact surface, thereby increasing the depth sensitivity of the device.

PEFS system 100 may further include a measuring means 2 operatively associated with PEFS 1 or an array of PEFS's 1. Measuring means 2 may be any electrical device, such as an oscilloscope or a voltage meter coupled with a computer, capable of measuring a displacement of the cantilever in the form of an induced voltage between electrodes 7 and 6' across the piezoelectric layer 4 in the first embodiment shown in FIG. 2(a) or an induced voltage between electrodes 7 and 7' of the second piezoelectric layer 5' in the second embodiment shown in FIG. 2(b), that may be used together with the applied force to obtain a force-displacement plot whose slope may be used to deduce elastic modulus, shear modulus and/or a G/E ratio for the tested tissue. Measuring means 2 may be capable of numerically, graphically or otherwise displaying the measurements obtained from PEFS 1 and/or calculations based on these measurements, including the elastic modulus, shear modulus and/or G/E ratio. In one embodiment, measuring means 2 may be capable of analyzing the data and expressing the location of tissue abnormalities in polar coordinates so as to graphically and accurately locate the abnormal tissue within or relative to the tested tissue. In an exemplary embodiment, the measuring means 2 may be a portable electrical measurement unit capable of handling multiple measurements from a plurality of PEFS's 1 in an array. Preferably, the measuring unit may also be programmed to automatically deduce the elastic modulus, shear modulus and/or G/E ratio associated with a particular tissue sample.

In an exemplary embodiment, the measuring means 2 enables real time imaging and/or graphical representation of these calculations. Preferably, the measuring means 2 may employ data processing speeds which enable real time in vivo data processing, scanning and imaging. More preferably, the measuring means 2 may be portable and may enable visualization of the analyzed data and/or calculated properties of the tissue. In an exemplary embodiment, measuring means 2 may be a portable unit the size of a pocket calculator and may run on electricity or a battery-based power source.

PEFS 1 or an array of PEFS 1 may also be attached to an automated and/or manual positioning means 3 that facilitates the positioning of the PEFS 1 relative to the soft tissue. Although the PEFS 1 may be manually placed on a tissue surface, the automated positioning means 3, as shown in FIG. 1, may be employed to more efficiently, more quickly and/or more accurately position PEFS 1. Furthermore, the automated positioning means 3 may be used to move PEFS 1 from location to location, speeding up the measuring process and facilitating in vivo clinical application of the device. In an exemplary embodiment, the automated positioning means 3 may be a programmable robotic arm capable of 3-D automated positioning, such as the Crust-Crawler AX-12 Smart Arm w/CM-5 Bundle. Alternatively, automated positioning means 3 may also be a three-dimensional positioner using a set of stepping motors.

2. Method for Using the Piezoelectric Finger Sensor (PEFS) System

The method of the present invention is a noninvasive method of using a PEFS 1 to determine the type, invasiveness and/or malignancy of a tumor contained within a tissue. The method involves placing a PEFS 1 or an array of PEFS 1 in contact with a tissue surface. In an exemplary embodiment, PEFS 1 may be applied to a tissue surface in a manner similar to manual palpation by contacting and rubbing the tissue surface. PEFS 1 therefore functions like an electronic finger that enables electronic palpation by electrically applying a force to and electronically measuring a displacement of the tissue.

PEFS 1, as shown in FIG. 2(b), may be operated by applying a voltage to piezoelectric layer 4 of PEFS 1. The voltage causes PEFS 1 to bend due to the converse piezoelectric effect, which generates a force and displacement at the sensor's cantilever tip. The bending of the cantilever generates an induced piezoelectric voltage in a piezoelectric layer 4 or 5 of PEFS 1 in proportion to the displacement at the cantilever tip. Therefore, by carefully monitoring the displacement of the cantilever tip and determining the net force exerted on the tissue which is a combination of the force from the applied voltage and the countering force from tissue deformation, it is possible to determine the elastic modulus and shear modulus of a particular tissue sample based on the displacement of the cantilever tip, relative to the expected displacement of the tip in the absence of the tissue sample. The displacement measurements may be used to determine the elastic modulus, shear modulus and G/E ratio for a particular tissue sample.

Figure 5A:
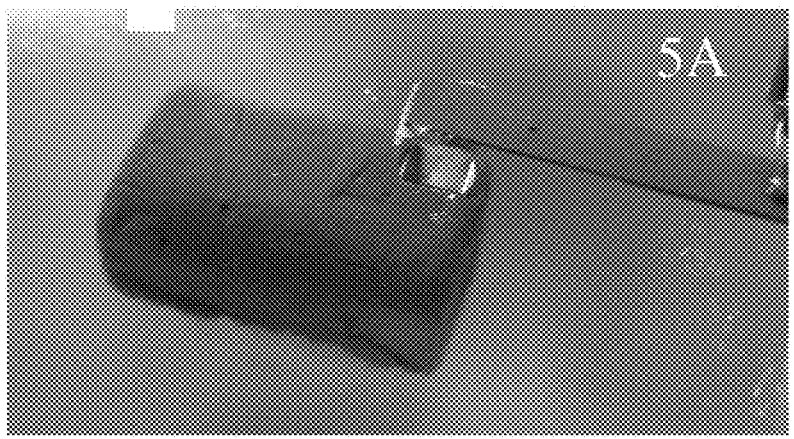
FIG. 5(a) is a photograph of a smooth inclusion with the piezoelectric cantilever positioned for elastic modulus measurement.

To measure the elastic modulus, PEFS 1 may be placed in contact with a tissue surface, as shown in FIG. 5(a). When a voltage is applied to PEFS 1, a force is exerted by the PEFS on the tissue in a direction orthogonal to the tissue surface, inducing vertical displacement of the tip of PEFS 1 into the plane of the tissue. By measuring the applied force and the resultant displacement of the cantilever tip, it is possible to determine net force exerted on the sample and obtain the elastic modulus of the tissue from the slope of the force-displacement curve. The PEFS 1 may be used to directly determine the elastic modulus of tissue in any direction, including the length, width or thickness of a tissue sample. The measured elastic modulus may, in some cases, be employed to screen for the presence of abnormal tissue. Specifically, tissue having an abnormally large elastic modulus may indicate the presence of abnormal tissue.

Figure 5B:
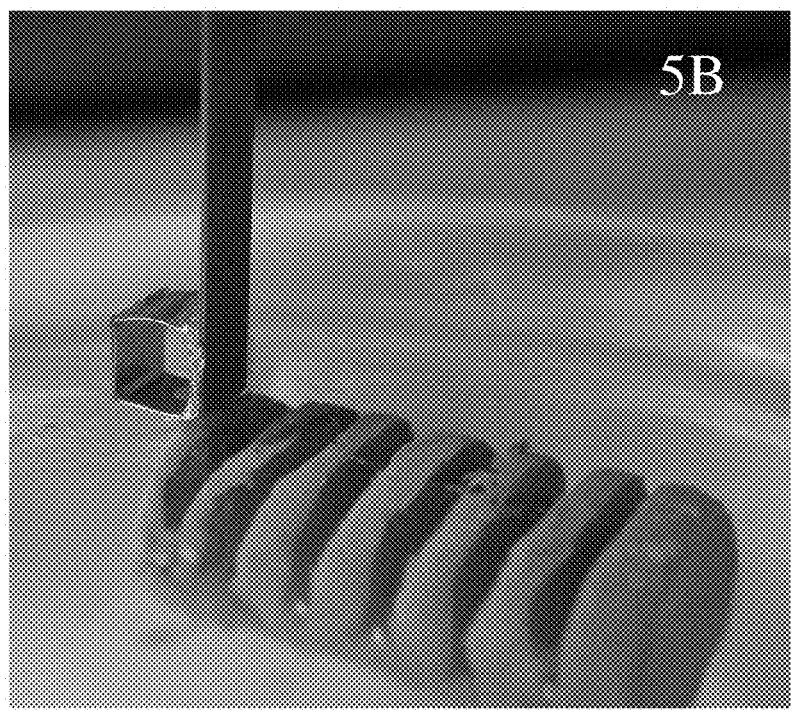
FIG. 5(b) is a photograph of a rough inclusion with the piezoelectric cantilever positioned for shear measurement perpendicular to the direction of the corrugation.

To measure the shear modulus, PEFS 1 may be placed in contact with a tissue surface, as shown in FIG. 5(b). A voltage is applied to PEFS 1 inducing exertion of a force on the tissue in a direction parallel to the tissue surface and consequently, producing a horizontal displacement of the PEFS 1 tip. By measuring the applied force and the resultant displacement of the cantilever tip, it is possible to determine the net force exerted on a tissue and deduce the shear modulus of the tissue from the net force-displacement curve. PEFS 1 may be used to directly determine the shear modulus of tissue with the shear movement in any direction, including the length or the width direction of a tissue sample. The measured shear modulus distribution map may be used as a screening test to determine for the presence of abnormal tissue. Specifically, tissue having an abnormally large shear modulus may indicate the presence of abnormal tissue.

A shear modulus measurement indicative of a smooth interfacial area may be an indicator of a non-invasive tumor whereas a shear modulus measurement representative of a rough and branchy interfacial area may be an indicator of an invasive tumor. Without wishing to be bound by theory, it is thought that the shear modulus measurement is different for invasive and non-invasive tumors when measured in a particular direction which is preferably perpendicular to the interfacial branchy and rough protrusions of invasive tumors because the interlocking nature of the tissue in the interfacial area of invasive tumors renders the tissue specimen less mobile in the interfacial area than the tissue in the interfacial area for less interconnected non-invasive tumors. Similarly, the shear modulus may also provide a means for determining malignancy.

While either an elastic modulus distribution map or a shear modulus distribution map of a tissue sample may assist in determining the location, dimension and depth of a tumor, as well as the presence of abnormal tissue, a comparison of the G/E ratio of tissue samples enables further information to be determined about the abnormality. In an exemplary embodiment, the elastic and/or shear modulus distribution map may extend to an area of normal/healthy tissue in order to provide baseline elastic and/or shear modulus values for normal/healthy tissue. In this manner, the procedure can be carried out on any patient since no assumptions need to be made regarding the elastic or shear modulus of normal/ healthy tissue for that patient because the present method actually measures these values. Also, the accuracy and specificity of the present predictive method is enhanced since measured values for normal/healthy tissue of each patient are used as a basis for comparison thereby allowing for variations in the stiffness of tissue in different patients.

The G/E ratio is the ratio of the shear modulus to the elastic modulus for a particular tissue sample. Specifically, such a comparison may be used to determine information about the properties of the interfacial area of abnormal tissue, which may be used to assess tumor malignancy, invasiveness and, in some cases the type of tumor.

If it is known from the individual shear and/or elastic modulus distribution map that abnormal tissue is present, a low G/E ratio less than about 0.7, more preferably, about 0.5 or less and most preferably, about 0.3 or less at the location of abnormal tissue may be indicative of a non-invasive tumor such as carcinoma in situ and a high G/E ratio of 0.7 or larger may be indicative of an invasive tumor such as invasive carcinoma. Similarly, G/E ratio may also be used to determine malignancy. The first step to determining malignancy is identifying whether the tumor is confined by a tissue boundary which would otherwise alter the stiffness characteristics of the tissue. If the tumor is not confined, a G/E ratio of 0.7 or greater may be indicative of malignancy. If the tumor is confined, such as is the case for malignant ductal carcinoma in situ, a G/E ratio of about 0.3 or larger may be indicative of malignancy.

Notably, PEFS system 100 and the method of the present invention are extremely effective and accurate, achieving about 100% sensitivity in detecting breast abnormalities; about 96% sensitivity and about 54% specificity in detecting malignancy or invasive carcinoma with G/E>0.7 for a tumor that is not confined or a G/E>0.3 for a tumor that is confined and about 89% sensitivity and about 82% specificity in detecting malignancy with a G/E>0.7. For mechanically dense breast tissue the method achieved is about a 94% sensitivity and about 63% specificity for detecting malignancy with a G/E>0.7 for a tumor that is not confined or a G/E>0.3 for a tumor that is confined; and about 93% sensitivity and about 80% specificity for detecting malignancy in mechanically dense breast tissue with a G/E>0.7.

For purposes of the present application, specificity for malignancy is the number of non-cancer predictions divided by the number of actual non-cancer pathological diagnosis multiplied by 100. Specificity for invasive carcinoma is the number of non-invasive carcinoma predictions divided by the number of actual non-invasive carcinoma pathological diagnosis multiplied by 100. For purposes of the present application, sensitivity for malignancy is the number of cancer predictions divided by the number of actual cancer pathological diagnosis multiplied by 100. Sensitivity for invasive carcinoma is the number of invasive carcinoma predictions divided by the number of actual invasive carcinoma pathological diagnosis multiplied by 100. Accuracy for malignancy is the sum of the number of cancer predictions confirmed by cancer pathological diagnosis and the number of non-cancer predictions confirmed by non-cancer pathological diagnosis divided by the total number of cases multiplied by 100. Accuracy for invasive carcinoma is the sum of the number of invasive carcinoma predictions confirmed by invasive cancer pathological diagnosis and the number of non-invasive cancer predictions confirmed by non-invasive cancer pathological diagnosis divided by the total number of cases multiplied by 100.

One advantage of the invention is that it provides significantly less false positive readings than current mammography techniques, thereby minimizing the need to perform numerous unnecessary tissue biopsies for the false positive results of the mammograms.

Another potential advantage of the present invention is that it has a very high sensitivity indicating that there is a very low likelihood that cancerous tissue would be overlooked using the method of the present invention. This is important because it ensures that the method of the present invention, used alone, may be a reliable cancer screening method.

The G/E ratio may also be used to identify specific types of malignant or benign tumors. Specifically, a G/E ratio of about 0.5, more preferably about 0.5 to 0.6, may be indicative of hyperplasia, and a G/E ratio of about 0.3, more preferably about 0.2-0.4 combined with an identification of the presence of abnormal tissue obtained from one or more of the individual shear and elastic modulus maps of the sample, may be indicative of carcinoma in situ or benign tumors, such as fibrocystic or fibroadipose. Although healthy tissue may also exhibit G/E ratios about 0.3, cancerous tissue and tumors having a G/E ratio in this range can still be identified by its higher shear and elastic modulus than that of the healthy surrounding tissue. It has been found, for example, that a benign tumor may have a G/E ratio of about 0.3, the same as for healthy tissue, but that the individual measurements of shear modulus and elastic modulus of the benign tumor are typically higher than the individual measurements of shear modulus and elastic modulus for healthy tissue, thereby allowing the prediction of the presence of a benign tumor under these circumstances.

In the case of carcinoma in situ, it may be necessary to also consider the location of the tissue in question to complete the prediction of whether there is cancerous tissue or not. In this case, the surrounding tissue of, for example, a milk duct, can confine the cancerous tissue, thereby altering the shear and/or elastic moduli of the cancerous tissue in the interfacial area. As a result, the carcinoma in situ will typically exhibit a G/E ratio of about 0.3 due to confinement of the interfacial area by the surrounding tissue. However, individual shear and elastic modulus measurements can again be used to predict the presence of the carcinoma in situ under these circumstances since the individual shear and elastic moduli will differ from that of healthy tissue. Although benign tumors such as fibrocystic tumors also exhibit a higher shear modulus and elastic modulus value than those of the surrounding healthy tissue, inclusion of abnormal tissue as identified by the individual elastic modulus map or shear modulus map that exhibit a G/E about 0.3 would still allow positive predictions of all carcinomas in situ.

The method of the present invention may further involve the step of artificially increasing the perceived interfacial roughness of a tumor in order to enhance the sensitivity of the indicator for malignancy, invasiveness or tumor type. The perceived interfacial roughness may also be enhanced for examination of tumors located at a significant depth below the tissue surface or tumors which have developed large interlocking networks. In an exemplary embodiment, the perceived interfacial roughness may be increased by increasing the angle of the scan path relative to the interfacial protrusions. For purposes of the present invention, the angle of the scan path refers to the orientation of PEFS 1 relative to the interfacial protrusions when the shear force is applied. Different scan angles are achieved by rotating PEFS 1, shown in FIG. 5(b), about its longitudinal axis, relative to the tissue sample. Preferably, the angle is at least 30 degrees, more preferably, at least 60 degrees and, most preferably, about 90 degrees.

Upon analyzing and diagnosing the tissue sample, measuring means 2 may be used to express the location of tissue abnormalities in polar coordinates so as to graphically and accurately locate the abnormal tissue within or relative to the tested tissue based on the elastic modulus, shear modulus and/or G/E measurements. Additionally, measuring means 2 may be also be used to quantitatively determine and map the size and depth of the tissue abnormalities. In an exemplary embodiment, the location and dimensions of the abnormal tissue may be displayed on a 2D or 3D map to facilitate surgery.

The PEFS system 100 and method of the present invention are particularly advantageous in comparison to the tumor detection and evaluation methods of the prior art. The method of the present invention is capable of screening for the type, invasiveness and malignancy of a tumor by quantitatively measuring tissue stiffness and is not dependent upon the density difference between the tumor and the surrounding tissue or angiogenesis. These quantitative measurements may be unilaterally and uniformly used by any oncologist or physician to render an objective determination as to the presence of, dimension of, location of, type of, invasiveness of and/or malignancy of a tumor without requiring the interpretation of a highly trained radiologist.

Furthermore, the method and system 100 of the present invention is a highly effective means for evaluating tissue specimens and is particularly well suited for in vivo tissue imaging. The PEFS system 100 is sensitive and capable of detecting minute tumors less than about 0.5 cm (in a demonstrated case, the cancer was 3 mm in size) that are frequently missed by mammography, ultrasound, and/or palpation, which typically have a size sensitivity limitation of about 1 cm. The PEFS is extremely accurate and highly sensitive, producing results unmatched by currently existing technologies. In comparison to screening tests such as mammography, magnetic resonance imaging, ultrasound imaging and SureTouch™ imaging, the PEFS system 100 has a higher sensitivity and specificity for identifying the presence of a tumor as well as for predicting malignancy and tumor invasiveness. The depth sensitivity may be further enhanced or customized by changing the width of the PEFS sensor or PEFS array, as discussed above.

Another particularly advantageous feature of the present invention is the ability to detect tumors, malignancies and invasive carcinomas in mechanically dense tissue. For example, in breast cancer detection, the device of the present invention is suitable for both heterogeneously dense tissue which is defined as being composed of 51-75% glandular tissue and extremely dense tissue which is defined as being greater than 75% glandular tissue. These definitions are taken from the BI-RADS Breast Imaging Lexicon found at http://www.radiologyassistant.nl/en/4349108442109 which classifies mammographic breast tissue composition into four distinct categories. This is important since human females under 40 years of age tend to have breast tissue that falls into one of these two categories and mammographic imaging methods are not well-suited for distinguishing tumors from, for example, extremely dense breast tissue.

Moreover, because the PEFS system 100 of the present invention does not operate on radiation or electromagnetic waves, patients are not exposed to potentially harmful effects as a result of the testing and may repeat the testing at any time without concern for adverse health risks. This may be particularly beneficial for physicians attempting to track fast growing cancers. By contrast, screening procedures such as mammography, may only be preformed once a year. The method of the present invention is also noninvasive and gentle, requiring a strain of less than 1%, thereby causing minimal to no patient discomfort. Furthermore, the PEFS system 100 is also portable, inexpensive and may be mass produced with relative ease, making it capable of being widely implemented.

In another aspect, the present invention provides the ability to measure the dimensions and/or position of abnormal tissue in a tissue sample. The dimensions and/or position of abnormal tissue may be determined by measuring the elastic modulus and thickness of the tissue sample and abnormal tissue using a PEFS array having a plurality of PEFS' 1 of different widths, i.e. tissue contact regions. In an exemplary embodiment, a PEFS' array having 3 or more PEFS' 1 may be used to analyze abnormal tissue positioned on or near the surface of the tissue, and a PEFS' array having 5 or more PEFS' 1 may be used to detect abnormal tissue suspended in or supported on a distal bottom surface of the tissue. By measuring the elastic modulus of the tissue sample using PEFS' 1 of different widths, and consequently different depth sensitivities, the elastic modulus and thickness of the abnormal tissue and the elastic modulus of the surrounding tissue can be calculated. From these calculations, the dimensions of the abnormal tissue as well as the depth and position of the of the abnormal tissue within the tissue sample can be determined. The length and width of the abnormal tissue can be determined from the tissue map as described above.

The depth and position of the abnormal tissue can be determined using a PEFS array with 3 PEFS' 1 having a depth sensitivity of $h_1$, $h_2$, and $h_3$, the elastic elastic moduli for each of these PEFS', $E_1$, $E_2$, and $E_3$, may be obtained in the manner discussed above. By solving the equations (1)-(3) below, $$\text{For Cantilever 1: } \frac{1}{\frac{E_1}{h_1}} = \frac{1}{\frac{Es}{ts}} + \frac{1}{\frac{Ef}{(h_1 - ts)}} \quad (1)$$

$$\text{For Cantilever 2: } \frac{1}{\frac{E_2}{h_2}} = \frac{1}{\frac{Es}{ts}} + \frac{1}{\frac{Ef}{(h_2 - ts)}} \quad (2)$$

$$\text{For Cantilever 3: } \frac{1}{\frac{E_3}{h_3}} = \frac{1}{\frac{Es}{ts}} + \frac{1}{\frac{Ef}{(h_3 - ts)}} \quad (3)$$

it is then possible to determine the elastic modulus and thickness (i.e. depth) of the abnormal tissue, $E_s$ and $t_s$, respectively, as well as the elastic modulus, $E_f$, of the surrounding tissue. This methodology is exemplified in Example 11 below.

Previously we have described a two-spring model that measures the depth of a bottom-supported tumor embedded inside tissues (See Rev. Sci. Instr. 78, 115101 (2007)). The present invention extends this to cover the situation where the effect of a bottom-supported tumor is determined, as well as to make depth determinations in the situation where the tumor is suspended above the bottom support.

Bottom-supported Inclusions

Three piezoelectric fingers (PEFs) are used for this determination, as shown in FIG. 29(b). FIG. 29(a) illustrates the situation where the bottom support is not considered. This situation is discussed above.

For bottom-supported inclusions it is desirable to determine the elastic modulus of the normal tissue, $E_g$, the elastic modulus of the abnormal tissue, $E_i$, the elastic modulus of the bottom support (i.e. chest wall for breast tissue), $E_b$, the depth or height from the surface to the bottom support, $h_t$, and the depth or height to the top of the abnormal tissue, $h_i$.

Using a first PEF with depth sensitivity $h_1 < h_t$, the following equations can be developed:

Away from the inclusion:

$E_1 = E_g$

Above the inclusion:

$h_1/E_1 = h_i/E_g + (h_1 - h_i)/E_i$,

Using a second PEF with depth sensitivity $h_2 < h_t$, the following additional equation can be developed:

Above the inclusion:

$h_2/E_2 = h_i/E_g + (h_2 - h_i)/E_i$.

Using a third PEF with depth sensitivity $h_3 > h_t$, the following additional equations can be developed:

Away from the inclusion:

$h_3/E_3 = h_t/E_g + (h_3 - h_t)/E_b$,

Above the inclusion:

$h_3/E_3 = h_i/E_g + (h_t - h_i)/E_i + (h_3 - h_t)/E_b$.

With the five equations we can solve for the five unknowns: $E_g$, $E_i$, $E_b$, $h_i$, and $h_t$. It can be verified that the PEFs correspond to PEF1, PEF2, and PEF3. When PEF1 and PEF2 are used, away from the inclusion the E values are the same and are smaller than when PEF3 is used. Also, above the inclusion, $E_3$ should be larger than $E_1$ and $E_2$.

Suspended Inclusions

This is the situation of FIG. 29(c) and for this situation a fourth PEF is required. For suspended inclusions it is desirable to determine the elastic modulus of the normal tissue, $E_g$, the elastic modulus of the abnormal tissue, $E_i$, the elastic modulus of the bottom support (i.e. chest wall for breast tissue), $E_b$, the depth or height from the surface to the bottom support, $h_t$, the depth or height from the surface to the bottom of the abnormal tissue, $h_{ib}$, and the depth or height to the top of the abnormal tissue, $h_i$.

Using a first PEF with depth sensitivity $h_1 < h_t$, we have the following equations:

Away from the inclusion:

$E_1 = E_g$

Above the inclusion:

$h_1/E_1 = h_i/E_g + (h_1 - h_i)/E_i$

Using a second PEF with depth sensitivity $h_2 < h_t$, we have the following equation:

Above the inclusion:

$h_2/E_2 = h_i/E_g + (h_2 - h_i)/E_i$

Using a third PEF with depth sensitivity $h_3 > h_t$, we have the following equations:

Away from the inclusion:

$h_3/E_3 = h_t/E_g + (h_3 - h_t)/E_b$,

Above the inclusion:

$h_3/E_3 = h_i/E_g + (h_{ib} - h_i)/E_i + (h_t - h_{ib})/E_g + (h_3 - h_t)/E_b$.

Using the fourth PEF with $h_t > h_4 > h_{ib}$, we have following equation:

Above the inclusion:

$h_4/E_4 = h_i/E_g + (h_{ib} - h_i)/E_i + (h_4 - h_{ib})/E_g$.

With these six equations we can solve for the five unknowns: $E_g$, $E_i$, $E_b$, $h_i$, $h_{ib}$, and $h_t$. The identify of PEF4 can be verified since away from the inclusion for PEF4, $E_4 = E_1 = E_2$. Above the inclusion, $E_4$ may be smaller or larger than $E_2$, but must be smaller than $E_3$. Meanwhile, away from the inclusion, $E_3 > E_1 = E_2 = E_4$ and above the inclusion $E_3 > E_4$.

It is envisioned that the PEFS system 100 will assist physicians in screening for tumors and various forms of cancer, including but not limited to breast cancer, prostate cancer, skin cancer or liver cancer, prior to or in conjunction with procedures such as biopsy, surgical procedures, mammography, magnetic resonance imaging, ultrasound imaging, or other radioactive or electromagnetic screening tests. The PEFS system 100 of the present invention may either be used independently or in conjunction with traditional screening methods to assist in the early detection of tumors or diagnosis/confirmation of cancer. It is further envisioned that because this novel method and PEFS system 100 may be used to detect millimeter-sized tumors that are typically missed by traditional screening methods, it may be particularly beneficial for early cancer detection. Also, since the present method does not rely on tissue density, it may also be particularly useful in women for whom traditional screening methods are ineffective due to tissue density issues. It may also be used for cancer/tumor monitoring for treatment evaluation. It may also be used before surgery to locate the cancer/tumor to help guide surgeons.

Additionally, the PEFS system 100 may also be used in the field of dermatology for testing skin elasticity, cellular elasticity/plasticity or other tissue related properties. Of course, the PEFS system 100 may be effectively used in conventional methods for making compression and shear measurements on pliable materials of any kind. It is to be understood that the PEFS system 100 is not intended to be limited to applications involving tissue measurements.

EXAMPLES

Example 1

A study was performed to determine the effectiveness of the PEFS of the present invention to accurately evaluate a set of artificial tissues, which mimic the physical properties of various types of tumors. The PEFS was used to determine whether the artificial tumors embedded in the artificial tissue samples have a rough or branchy interfacial surface, a potential indicator of invasive malignant cancer such as malignant breast cancer, by measuring the elastic modulus (E), shear modulus (G) and determining the G/E ratio for the artificial tissues. It was found that either the elastic modulus or the shear modulus may be used to discern the dimensions of the artificial tumor, and that the shear modulus may further be used to characterize the texture of interface of a tumor with the surrounding tissue. Additionally, when the shear modulus was measured using a scan path substantially perpendicular to the direction of corrugation at the interface of the tissue, a G/E ratio of greater than about 0.7 was found when probing malignant tissue.

The piezoelectric cantilever used in the study, which is schematically shown in FIG. 4(a), was constructed to have a 22±0.2 mm in length top layer of lead zirconate titanate (PZT) (T105-H4E-602, Piezo Systems Inc., Cambridge, Mass.) and a 11±0.2 mm long bottom layer of PZT bonded to a 50-μm thick stainless steel layer (Alfa Aesar, Ward Hill, Mass.) located between the PZT layers using a nonconductive epoxy (Henkel Loctite Corporation, Industry, Calif) cured at room temperature for one day. The cantilever was 3.8±0.2 mm wide. Both the top and bottom PZT layers were 127 μm thick. The top PZT layer was used for force application. When a voltage was applied across the thickness of the top PZT layer, it created a lateral strain in the top PZT layer due to the converse piezoelectric effect of the top PZT layer. The created strain bends the cantilever. The force produced by the cantilever bending was calibrated for force application.[14] The bottom PZT layer was used as a displacement meter. Upon bending of the cantilever, a voltage difference was generated across the thickness of the bottom PZT layer due to the direct piezoelectric effect and the axial displacement of the cantilever was calibrated with the induced voltage across the bottom PZT layer.[15] Thus, with both the top and bottom PZT layers, the cantilever was able to both apply a force and provide a displacement sensor in one device using simple electrical means.[15] The stainless steel tip was further fashioned into a square loop at the free end with each side of the square equal to the width of the cantilever to facilitate both compression and shear measurements using the same cantilever. The cantilever was clamped with a fixture made of 7.5 mm thick acrylic (McMaster-Carr, New Brunswick, N.J.). The PZT layers had a piezoelectric coefficient, $d_{31}$=−320 pC/N as specified by the vendor. The elastic modulus of the stainless steel and that of the PZT layers were 200 GPa and 62 GPa, respectively according to the vendors. The capacitance and the loss factor of a PZT layer were measured using an Agilent 4294A Impedance Analyzer (Agilent, Palo Alto, Calif.). The contact area of the square stainless steel loop was 3.8 mm×3.8 mm. The effective spring constant, K, of the cantilever was 143 N/m as determined using a published procedure.[15] A DC power supply, HP E3631A, (Hewlett-Packard Company, Palo Alto, Calif.) was used as the programmable DC voltage source. The measurements were obtained using a Newport optical table (RS1000, Newport Corporation, Irvine, Calif.) to minimize low-frequency background vibrations. The applied voltages across the driving PZT layer and the induced voltage across the sensing PZT layer were recorded on an Agilent Infiniium S4832D digital oscilloscope (Agilent, Palo Alto, Calif.). The DC power source and the oscilloscope were connected to a personal computer (PC). All voltage measurements, real-time elastic modulus computations, and data acquisition were controlled from a PC by LabView (National Instrument, Austin, Tex.) programming.

The artificial tissues tested in the study were constructed by embedding modeling clay in gelatin (Fisher Scientific, Pittsburgh, Pa.). Three types of modeling clays were used: Modeling clay C54 (Play-Doh, Hasbro Ltd., Newport, UK) with an elastic modulus of 54±12 kPa. Modeling clay C92 (Model Magic, Crayola, Easton, Pa.) with an elastic modulus of 92±9 kPa, and modeling clay C145 (Modeling Clay, Crayola, Easton, Pa.) with an elastic modulus of 145±10 kPa. In order to evaluate the interfacial properties of different tumors, each type of modeling clay was molded to form two types of inclusions 8 of the same size, about 22 mm long, 12 mm wide, and 14 mm high, having different surface textures. A first inclusion 8 fabricated with a smooth top surface S, as shown in FIG. 5(a), represented benign tumors and a second inclusion 8 with a corrugated top surface R, as shown in FIG. 5(b), represented malignant tumors. The corrugated surface mimicked the physical properties of the branchy or roughened interfacial area of malignant tumors. All R inclusions had rectangular grooves 2-4 mm wide and 7 mm deep running along the width of the inclusions. After formation, the modeling clay inclusions were embedded in a matrix 9, such as gelatin, wherein the top of the inclusion surface was 3 mm from the top gelatin surface. The concentration of the gelatin matrix 9 was 0.21 g/ml prepared by mixing 57.75 g of gelatin (Fisher Scientific, Pittsburgh, Pa.) in 275 ml of water at 80° C. on a hot plate for 5 min. After placing each of the samples in a dish, the gelatin mixture was poured over the samples to the desired height, cooled at 5° C. for 1 hr to facilitate solidification and then equilibrated at room temperature for 1 hr prior to measuring.

The elastic modulus (E) of the artificial tissue samples was used to determine the dimension of a tumor. The elastic modulus of the samples was measured using the PEFS in the indentation mode[16,17] such that the cantilever was oriented parallel to the artificial tissue surface, as shown in the photograph in FIG. 5(a). When a voltage $V_a$, was applied to the driving PZT layer of the cantilever, it generated a force producing a vertical displacement d (indentation) into the tissue, thereby inducing a voltage, $V_{in}$, across the sensing PZT layer. The elastic modulus, E, of the tissue is related to the applied force F, contact area, A, and vertical tissue displacement, d, as $$E = \frac{1}{2}\left(\frac{\pi}{A}\right)^{1/2}(v - v^2)\frac{F}{d}, \qquad (1)$$

where v the Poisson's ratio of the tissue. Because the tip displacement, d, of the measuring cantilever is linearly proportional to $V_{in}$, the elastic modulus, E, can be conveniently expressed in terms of $V_{in}$ as $$E = \frac{1}{2}\left(\frac{\pi}{A}\right)^{1/2}(1 - v^2)\frac{K(V_{in,0} - V_{in})}{V_{in}}, \qquad (2)$$

where K is the spring constant of the measuring cantilever, $V_{in,0}$ is the induced voltage across the sensing PZT layer of the measuring cantilever without the tissue. Thus, by knowing the $V_{in,0}$ before hand and by measuring $V_{in}$ at various $V_p$, the elastic modulus, E, of the tissue can be deduced by plotting $$\frac{1}{2}\left(\frac{\pi}{A}\right)^{1/2}(1 - v^2)K(V_{in,0} - V_{in})$$

versus $V_{in}$, and conveniently done through LabView. The measurement detail can be found in Ref. 18.

The elastic moduli of each inclusion obtained by scanning along the x and y directions are termed $E_x$ and $E_y$, respectively. Note that all the S inclusions and R inclusions had the same length, width, and height, only differing in the fact that the S inclusions had a smooth top surface while the R inclusions had a corrugated surface. The scanned area for each inclusion and its vicinity was 44 mm×68 mm with a 4 mm interval.

Figure 6A:
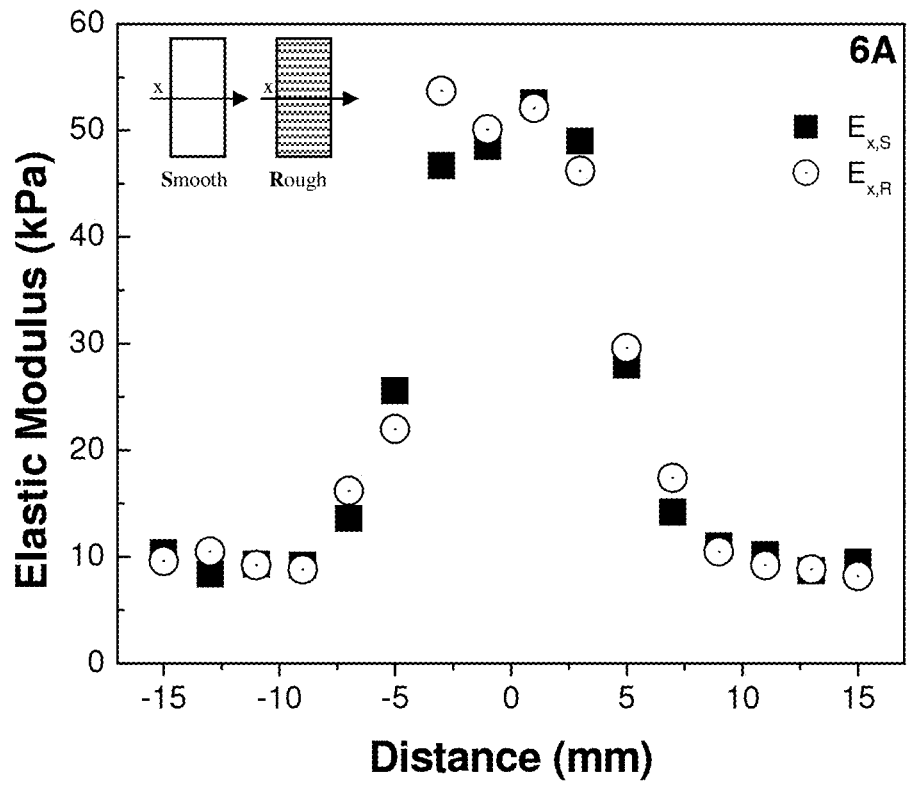
FIG. 6(a) is a graph of elastic modulus as a function of distance from the center of the inclusion in an x direction for smooth (full squares) and rough (open circles) inclusions made of C145.
Figure 6B:
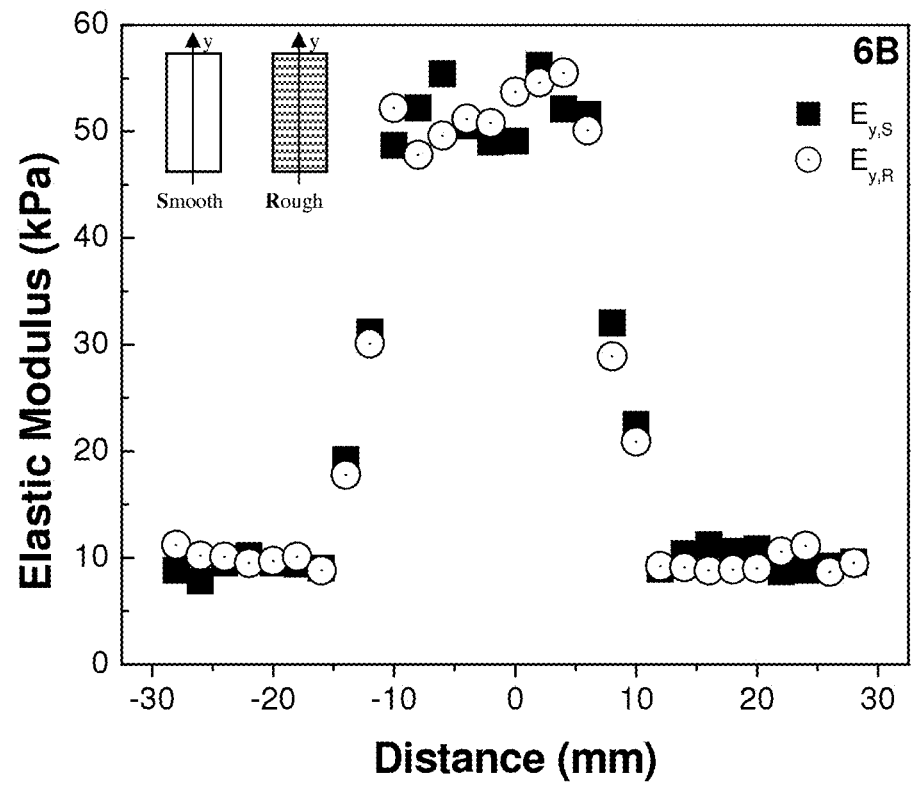
FIG. 6(b) is a graph of elastic modulus as a function of distance from the center of the inclusion in a y direction for smooth (full squares) and rough (open circles) inclusions made of C145.

As an example, the elastic modulus profiles in the x direction and those in the y direction of the C145 modeling clay S and R inclusions are shown in FIG. 6(a) and FIG. 6(b), respectively. $E_{x,S}$ and $E_{x,R}$ are the elastic moduli of the S and R inclusions, in the x direction along the center line of the inclusions, respectively, as schematically shown in the insert in FIG. 6(a), and $E_{y,S}$ and $E_{y,R}$ are the elastic moduli of the S and R inclusions in the y direction along the center line of the inclusions, as schematically shown in the insert in FIG. 6(b). Clearly, $E_{x,S}$, $E_{x,R}$, $E_{y,S}$, and $E_{y,R}$ were all about 52±3 kPa above the inclusions and dropped to a constant value of about 9±1 kPa away from the inclusions, indicating that the elastic modulus measurement was independent of the surface roughness and scan direction. The elastic modulus of the gelatin matrix away from the inclusions was about 9±1 kPa. The length and width of the model tumors were estimated based on the width at half the peak height, which indicates a length of about 19±1 mm and about 20±1 mm and a width of about 9±1 mm and about 9.4±1 mm for the S and R inclusions, respectively. These figures are in agreement with the known lengths and widths of the S and R inclusions.

The shear modulus, when measured perpendicular to the direction of corrugation of the artificial tissue samples, was used to discern the texture of the interfacial area of the artificial tumor, which may be an indicator of malignancy. The shear modulus of the tissue was measured using the indentation shear experimental method wherein the cantilever was oriented perpendicular to the tissue surface, as shown in FIG. 5(b). In this geometry, a force, F, parallel to the tissue surface was exerted on the tissue when a voltage, $V_a$, was applied to the driving PZT layer of the measuring cantilever, producing a horizontal displacement, d, to the tissue and an induced voltage, $V_{in}$, to the sensing PZT layer. The shear modulus G of the tissue can be empirically expressed in terms of the horizontal force, F, the horizontal displacement, d, and the contact area, A as:

$$G = \alpha \frac{1}{2}\left(\frac{\pi}{A}\right)^{1/2}(1-v^2)\frac{F}{d}, \quad (3)$$

where α is a constant determined empirically. Experimentally, α was found to be 1±0.2. Because the induced voltage of the sensing PZT layer is proportional to the horizontal displacement of the tissue, similarly, the shear modulus, G, can be deduced using the induced voltage as $$E = \frac{1}{2}\left(\frac{\pi}{A}\right)^{1/2}(1-v^2)\frac{K(V_{in,0}-V_{in})}{V_{in}}, \quad (4)$$

which can be obtained by measuring $V_{in}$ and plotting $$\frac{1}{2}\left(\frac{\pi}{A}\right)^{1/2}(1-v^2)K(V_{in,0}-V_{in})$$

versus $V_{in}$ using LabView.

Figures 7A, 7B:
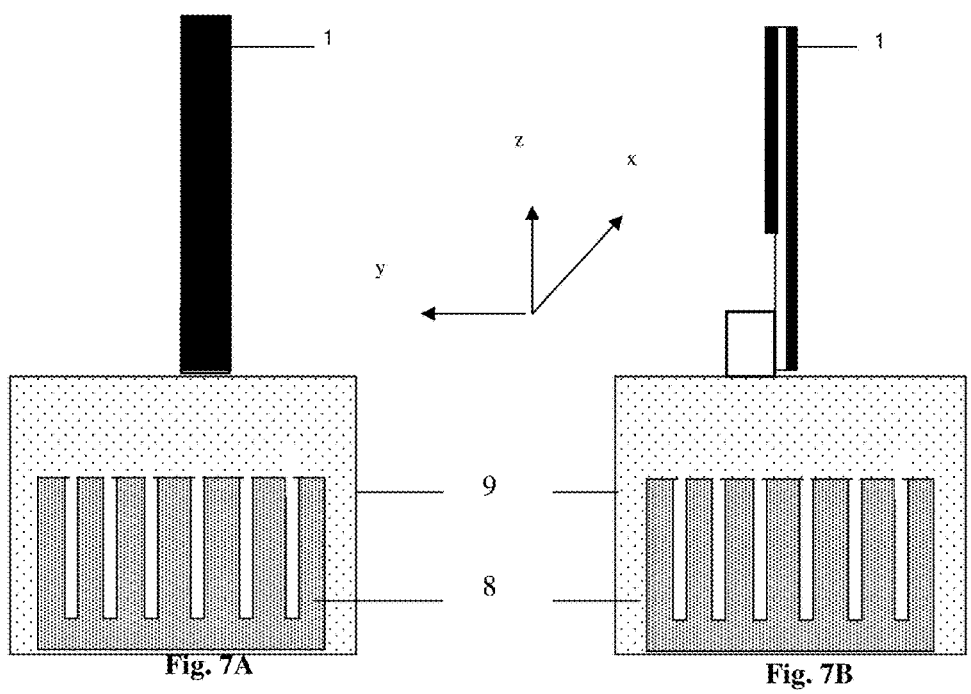
FIG. 7(a) is a schematic of a PEFS being used to apply a shear force parallel to the direction of corrugation (x direction).
FIG. 7(b) is a schematic of a PEFS being used to apply a shear force perpendicular to the corrugation (y direction).

For shear measurements, the PEFS was displaced parallel to the corrugation (i.e., the displacement is in the x-direction) as schematically shown in FIG. 7(a), and perpendicular to the corrugation (i.e., the displacement is in the y direction), as schematically shown in FIG. 7(b). The shear modulus was measured both with the contact area moving parallel to the corrugation, as shown in FIG. 7(a), and perpendicular to the corrugation, as shown in FIG. 7(b). Since the corrugation resides in the x direction of FIGS. 7(a) and 7(b), the measured shear modulus in which the contact area was moved parallel to the corrugation is $G_x$ and the measured shear modulus in which the contact area was moved perpendicular to the corrugation is $G_y$. Similarly, $G_x$ and $G_y$ are also measured over the S inclusions.

Figures 8A, 8B:
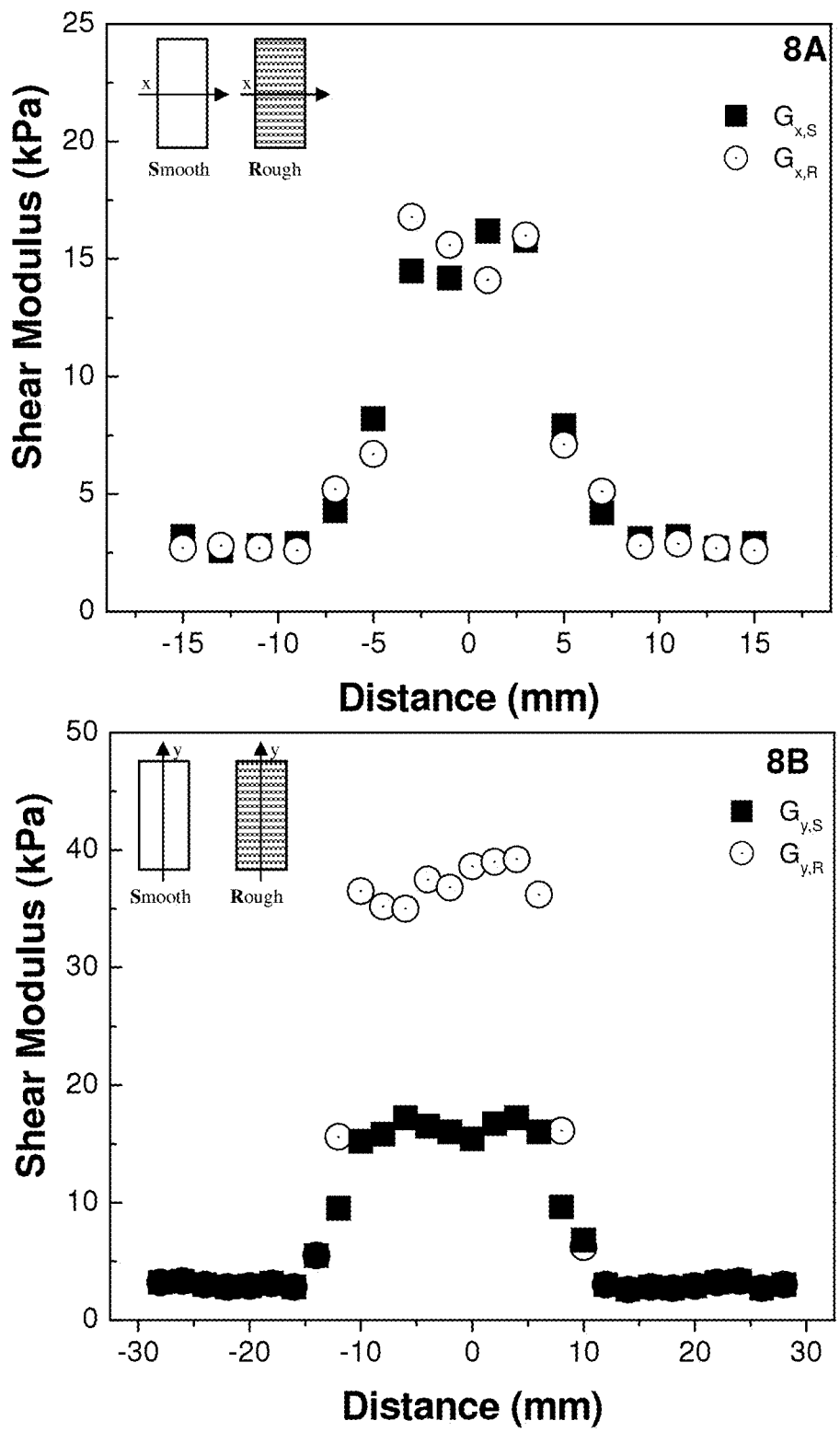
FIG. 8(a) is a graph of shear modulus as a function of distance from the center of an inclusion in an x direction for smooth (full squares) and rough (open circles) inclusions made of C145.
FIG. 8(b) is a graph of shear modulus as a function of distance from the center of an inclusion in a y direction for smooth (full squares) and rough (open circles) inclusions made of C145.

The shear modulus profiles in the x direction and those in the y direction are shown in FIGS. 8(a) and 8(b), respectively, where $G_{x,S}$ and $G_{x,R}$ were respectively the shear moduli of the S and R inclusions measured with the shear motion in the x direction (parallel to the corrugation of the R inclusions) along the center line of the inclusions as schematically shown in the insert in FIG. 8(a). $G_{y,S}$ and $G_{y,R}$ are, respectively, the shear moduli of the S and R inclusions measured with the shear motion in the y direction (perpendicular to the corrugation of the R inclusions) along the center line of the inclusions as schematically shown in the insert in FIG. 8(b). For the S inclusion, both $G_{x,S}$ and $G_{y,S}$ were about 16±1 kPa above the inclusion independent of the shear direction and fell off to about 3±1 kPa away from the inclusion. In contrast, for the R inclusion, the shear modulus measured perpendicular to the corrugation, $G_{y,R}$, and was found to be 37±2 kPa above the inclusion whereas the shear modulus measured parallel to the corrugation, $G_{x,R}$, was about 16±1 kPa. The length and width of the S and R inclusions as estimated from the width at half the peak height were 19.2±1 mm and 19.8±1 mm, 9.8±1 mm and 9.6±1 mm, respectively, in agreement with those obtained from the elastic modulus profiles and with the known values. Away from the inclusion both $G_{y,R}$ and $G_{x,R}$ fell off to a constant value of about 3±1 kPa. The above results indicate that surface roughness played a role in the shear modulus measurements above the inclusion. When the shear motion was parallel to the direction of corrugation, the measured shear modulus of a corrugated inclusion was similar to that of a smooth inclusion. On the other hand, when the shear motion was perpendicular to the direction of corrugation, the measured shear modulus was more than twice that of a smooth inclusion. Finally, the constant value of about 3±0.5 kPa in $G_{y,S}$, $G_{y,S}$, $G_{x,S}$ and $G_{x,R}$ away from the inclusions corresponded to the shear modulus of the gelatin matrix.

The ratio of the shear modulus, when measured perpendicular to the direction of corrugation, to the elastic modulus (G/E), was used to determine malignancy. It is known that Poisson's ratio, v, of an isotropic tissue or soft material is 0.5, which gives a G/E ratio of about 0.3. We plot $G_{x,S}/E_{x,S}$ and $G_{x,R}/E_{x,R}$ in FIG. 9(a) for the S and R inclusions and $G_{y,S}/E_{y,S}$ and $G_{y,R}/E_{y,R}$ in FIG. 9(b) for the S and R inclusions. Note that FIGS. 9(a) and 9(b) include the results from the S and R inclusions made from all three different modeling clays, C54, C92 and C145, which is also summarized in Table I.

TABLE I

Sample Measurements

| Sample | Interface | Elastic Modulus ($E_{y,S}$, $E_{y,R}$) | Shear Modulus ($G_{y,S}$, $G_{y,R}$) | $G_{y,S}/E_{y,S}$, $G_{y,R}/E_{y,R}$ | Elastic Modulus ($E_{x,S}$, $E_{x,R}$) | Shear Modulus ($G_{x,S}$, $G_{x,R}$) | $G_2/E_2$ |
|---|---|---|---|---|---|---|---|
| C54  | Smooth | 33.6 ± 1.9 kPa | 9.9 ± 0.3 kPa  | 0.29 | 30.5 ± 4.7 kPa | 8.7 ± 0.1 kPa  | 0.29 |
| C92  | Smooth | 43.4 ± 2.9 kPa | 13.1 ± 0.6 kPa | 0.30 | 41.8 ± 3.2 kPa | 12.7 ± 0.3 kPa | 0.30 |
| C145 | Smooth | 51.6 ± 2.7 kPa | 16.2 ± 0.7 kPa | 0.31 | 49.2 ± 2.5 kPa | 15.2 ± 1.0 kPa | 0.31 |
| C54  | Rough  | 32.3 ± 2.8 kPa | 24.8 ± 1.0 kPa | 0.77 | 29.3 ± 2.3 kPa | 8.5 ± 0.3 kPa  | 0.29 |
| C92  | Rough  | 41.4 ± 1.7 kPa | 30.0 ± 1.1 kPa | 0.72 | 41.4 ± 1.6 kPa | 12.6 ± 0.9 kPa | 0.30 |
| C145 | Rough  | 51.7 ± 2.5 kPa | 37.1 ± 1.6 kPa | 0.72 | 50.5 ± 3.2 kPa | 15.6 ± 1.1 kPa | 0.31 |

Figure 9A:
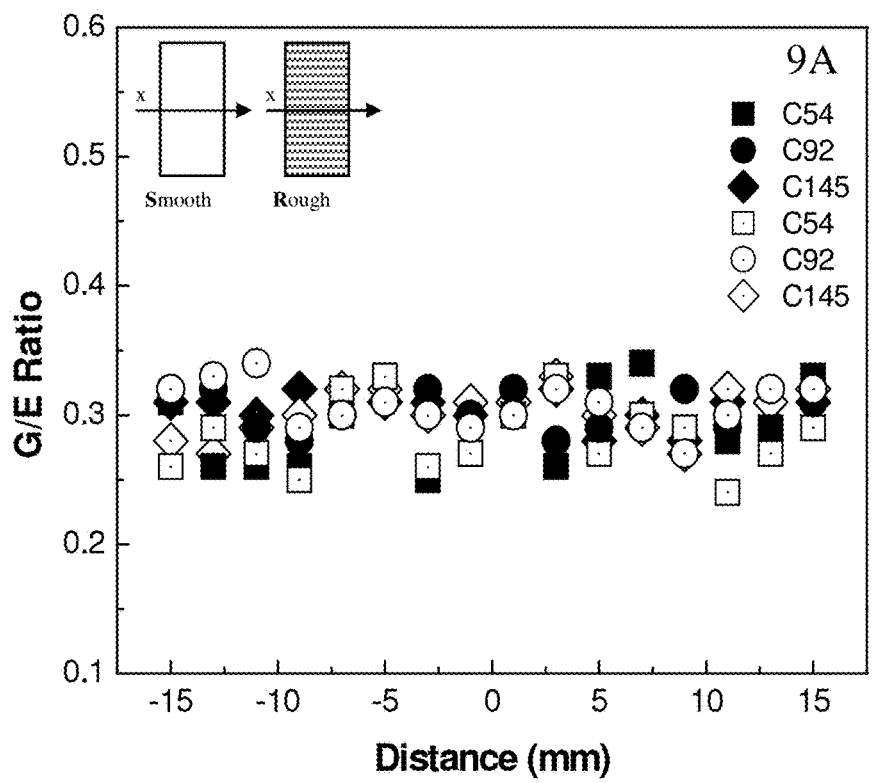
FIG. 9(a) is a graph of G/E ratio as a function of distance in an x direction for rough and smooth inclusions made of C54, C92, and C145.
Figure 9B:
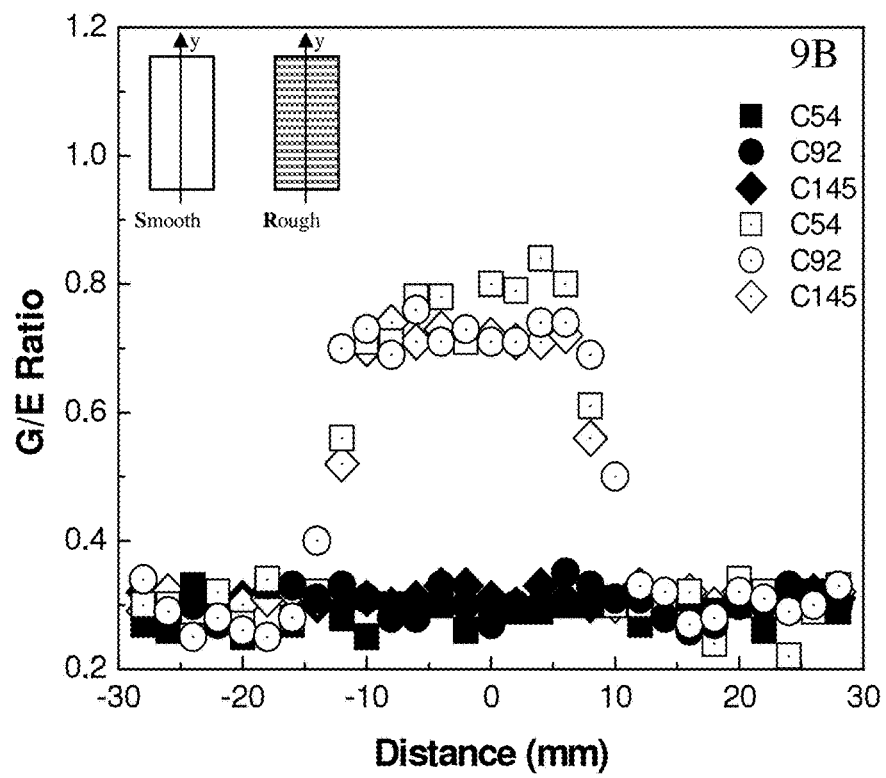
FIG. 9(b) is a graph of G/E ratio as a function of distance in a y direction for rough and smooth inclusions made of C54, C92, and C145.

FIG. 9(a) shows that for all the S inclusions, the G/E ratio remained around 0.3 above or away from the inclusion in both the x and y direction. FIG. 9(b) shows that unlike that of the S inclusions, the G/E ratio of all the R inclusions ($G_{y,R}/E_{y,R}$) was larger than 0.7 above the inclusion when the shear measurement was perpendicular to the direction of corrugation and fell off to about 0.3 away from the inclusion. In contrast, the G/E ratio of the R inclusions ($G_{x,R}/E_{x,R}$) was constant at about 0.3 above or away from the inclusion when the shear measurement was parallel to the direction of corrugation. As can be seen, the enhanced shear modulus of the R inclusions, when measured perpendicular to the corrugation, translated to an enhanced G/E ratio much larger than the 0.3 expected of isotropic soft tissues.

The shear modulus, when measured perpendicular to the direction of corrugation, was more than twice that measured parallel to the corrugation or that measured over a smooth inclusion. As a result, the G/E ratio was enhanced to over 0.7 above a rough inclusion when measured perpendicular to the corrugation, in contrast to the G/E ratio of a smooth inclusion or that of a rough inclusion measured parallel to the corrugation. Without wishing to be bound by theory, the enhanced shear modulus, and hence the enhanced G/E ratio over a rough inclusion when measured perpendicular to the direction of corrugation, was due to the interlocking nature of the corrugated surface which rendered it harder for either the gelatin or the modeling clay to move horizontally when subject to a shear stress.

Figure 11:
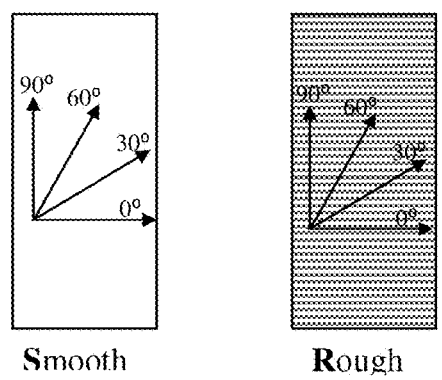
FIG. 11 is a schematic of the scanning paths.
Figure 12:
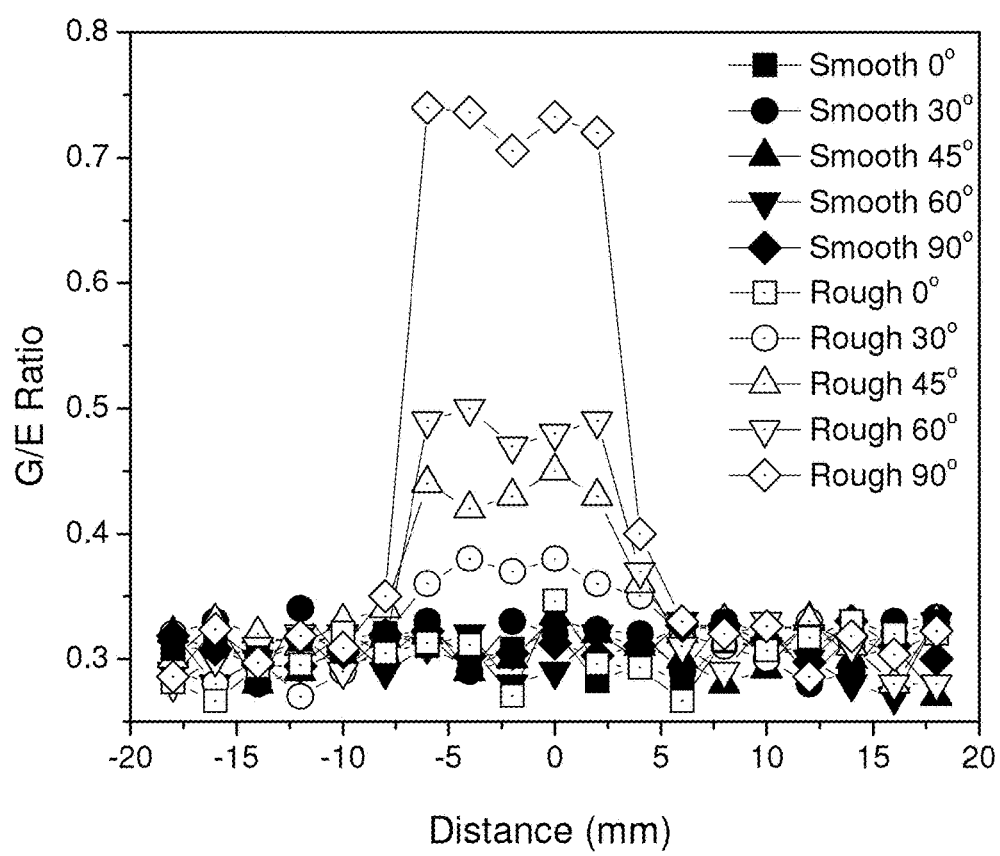
FIG. 12 is a graph of G/E ratio as a function of distance from the center of the inclusion at θ=0°, 30°, 60° and 90°.

To investigate whether the G/E ratio would change with a different degree of interfacial roughness, the E and G were measured along a scan path at an angle, θ to the x-axis, as schematically shown in FIG. 11. The obtained G/E ratio versus distance from the center of the inclusion at various θ is shown in FIG. 12. With respect to FIG. 12, all distances were normalized, such that the inclusions had the same width at all angles for easier comparison. As can be seen, the G/E ratio progressively increased from 0.33 for θ=0 (parallel to corrugation) to above 0.7 for θ=90° above the rough inclusion, whereas for the smooth inclusion, the G/E ratio remained around 0.33 regardless of the angle θ and whether it was above the inclusion or the gelatin. While changing the angle of the scan path relative to the direction of corrugation was not the only way to artificially increase the interfacial roughness, it served to illustrate that G/E ratio of the inclusion increased with the artificial increase in interfacial roughness as θ increased from 0 to 90°.

Additionally, the tested PEFS contact size was 3.8 mm, which was larger than the groove width, 2 mm. Therefore, most likely, in most measurements, the contact area either covered only a modeling-clay tooth or part of a modeling-clay tooth and part of a groove. Under such conditions, the depth of the R inclusion was essentially the depth of the modeling clay teeth, which was what was used for comparison in this study. However, if the contact size were smaller than the groove size, the measured shear modulus might differ depending on whether the measurement was above a tooth either partially or completely or entirely above a groove. The shear modulus measured above a tooth would be similar to what we measured in this study whereas that measured above a groove may be different as the groove had a much larger depth than the teeth.

Example 2

A PEFS was investigated to determine the depth sensitivity of elastic modulus measurements. The PEFS was fabricated from two piezoelectric layers, namely, a top 127 um thick PZT layer (105-H4E-602, Piezo System, Cambridge, Mass.) that functioned to drive a bottom 127 um thick sensing PZT layer bonded to a 50 um thick stainless steel layer (Alfa Aesar, Ward Hill, Mass.). The stainless steel layer formed a square tip at a distal end of the PEFS that was used to perform compression and shear tests.

Figures 13A, 13B:
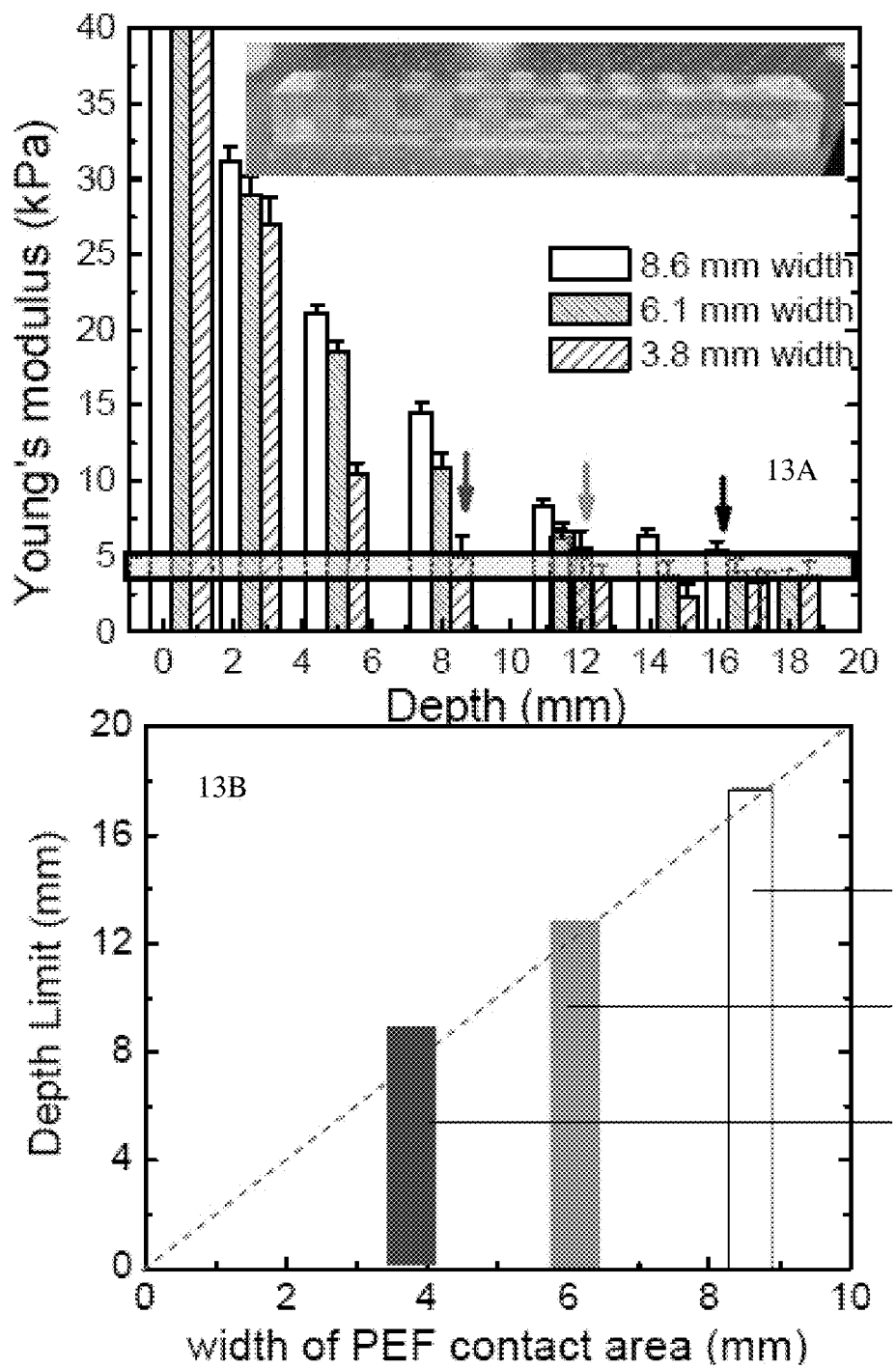
FIG. 13(a) is a graph of elastic modulus as a function of depth for modeling clay inclusions embedded at various depths, shown in the insert figure.
FIG. 13(b) is a graph of depth sensitivity limit as a function of the width of the PEFS contact area.

To determine the depth sensitivity of the PEFS, artificial tissue samples were prepared by embedding modeling clay model inclusions, having an elastic modulus of about 80 kPa, in a gelatin matrix, which has an elastic modulus of about 4±1 kPa, at various depths ranging from 2 to 17 mm, as shown in FIG. 13(a). The elastic moduli of the model tissues were then measured by indentation compression tests using three PEFS of various widths, namely 8.6 mm, 6.1 mm and 3.6 mm. The resultant elastic moduli of the model tissues were then plotted versus the depth at which the modeling clay were embedded in the gelatin matrix, as shown in FIG. 13(a). The white, green and red bars correspond to elastic moduli measured by the 8.6 mm, 6.1 mm, and 3.6 mm wide PEFS, respectively. As can be seen, the elastic moduli of the model tissues were essentially the same as that of gelatin matrix at a depth of ≥8 mm (red), ≥12 mm (green), and ≥16 mm (black), for the 3.6 mm (red), 6.1 mm (green), and 8.6 mm (black) wide PEFS, respectively. FIG. 13(b) shows a graph of the resultant depth sensitivity limit, which proves that the depth sensitivity limit of a PEFS is approximately twice the width of the contact area.

Example 3

The depth sensitivity of the PEFS of Example 1, defined as the maximum depth for which it is possible to obtain an accurate measurement, was investigated to determine sensor accuracy and reliability. Specifically, the depth sensitivity of the PEFS was investigated for determining the shear modulus and the G/E ratio of a tissue sample. Similar to previous studies which have confirmed that elastic modulus measurements are accurate to a depth sensitivity of about twice the size of the contact area of the PEFS, the depth limit for shear modulus measurements and the G/E ratio was also found to be about twice the size of the contact area.

The shear modulus of seven S inclusions embedded in artificial tissue samples and seven R inclusions embedded in artificial tissue samples were investigated. Each inclusion was about 22 mm long and 12 mm wide and was made of C92 modeling clay, which has an elastic modulus that closely mimics that of breast tumors. The inclusions were embedded at varying depths within a gelatin matrix. The depths of the inclusions were as summarized in Table II.

TABLE II

Inclusion Depth

| S Inclusion # | R Inclusion # | Depth (mm) |
|---|---|---|
| 1 | 1 | 1.7 |
| 2 | 2 | 3 |
| 3 | 3 | 4.7 |
| 4 | 4 | 7 |
| 5 | 5 | 8.6 |
| 6 | 6 | 10.1 |
| 7 | 7 | 11.6 |

The inclusions were embedded in a gelatin having an elastic modulus of 3±0.2 kPa and shear modulus of 1±0.2 kPa as determined on a separate gelatin sample prepared in the same manner. The elastic moduli and shear moduli of the seven S inclusions and seven R inclusions were measured above the centers of the inclusions and the shear moduli of the R inclusions were measured perpendicular to the direction of corrugation.

Figure 10A:
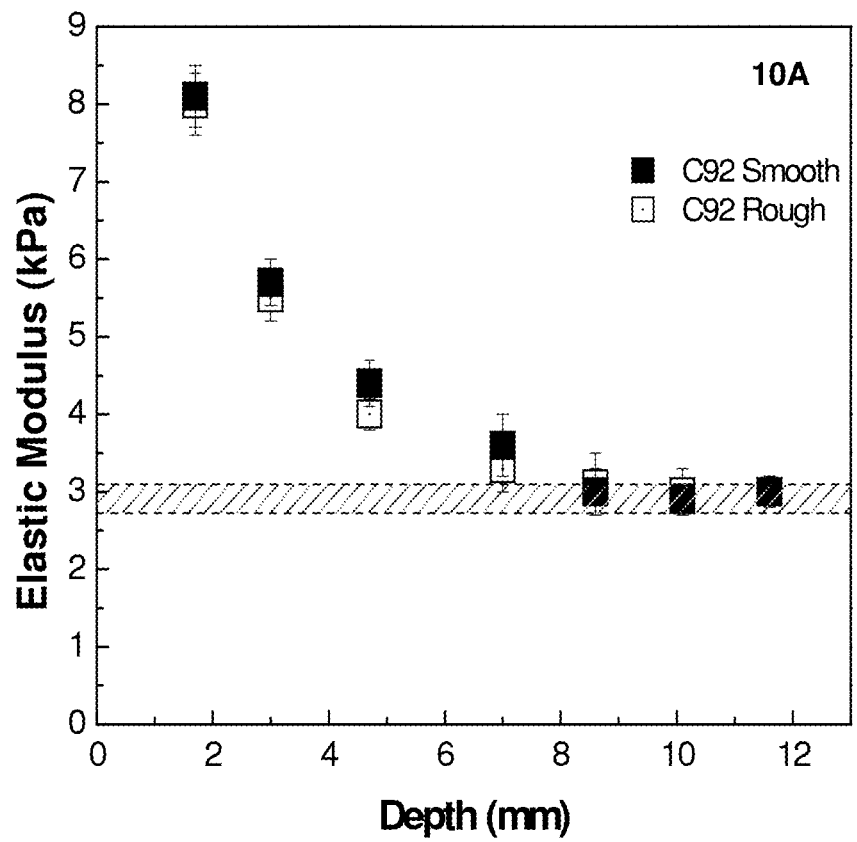
FIG. 10(a) is a graph of elastic modulus as a function of inclusion depth for rough and smooth inclusions made of C92.

FIG. 10(a) shows the resultant elastic modulus versus inclusion depth for both the S inclusions (open circles) and the R inclusions (open squares). The shaded horizontal band, shown in FIG. 10(a), represents the elastic modulus of the gelatin matrix with its experimental uncertainty. Empirically, the depth sensitivity of the elastic modulus measurement is the depth at which the measured elastic modulus of an inclusion became indistinguishable from that of the gelatin matrix. As can be seen, the measured elastic modulus versus depth of the S inclusions corresponded to that of the R inclusions, both exhibiting a depth sensitivity of between 7 mm and 8 mm, about twice the 3.8 mm width of the cantilever.

Figure 10B:
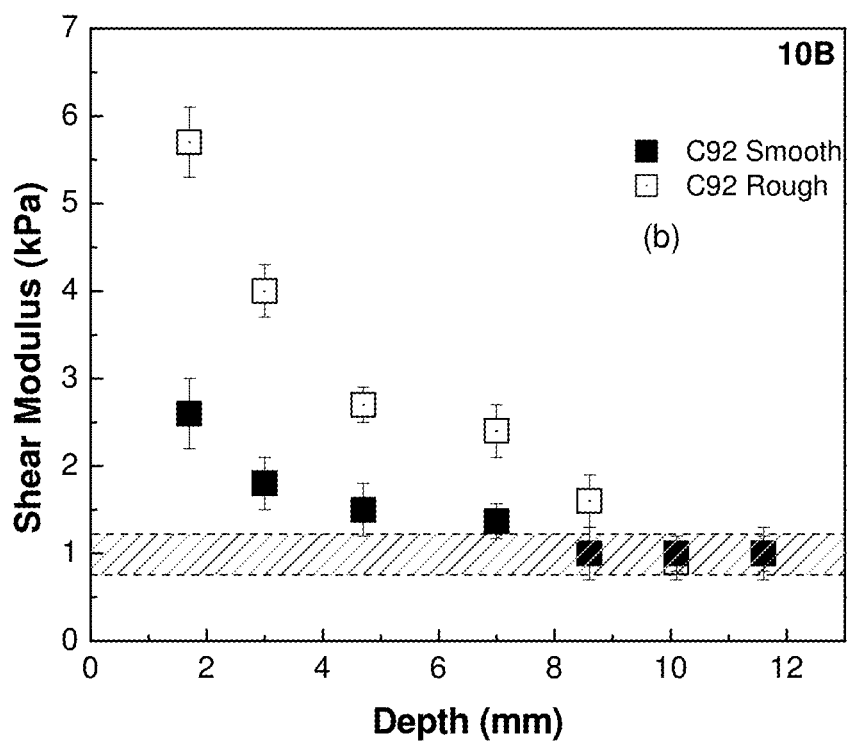
FIG. 10(b) is a graph of shear modulus as a function of inclusion depth for rough and smooth inclusions made of C92.
Figure 10C:
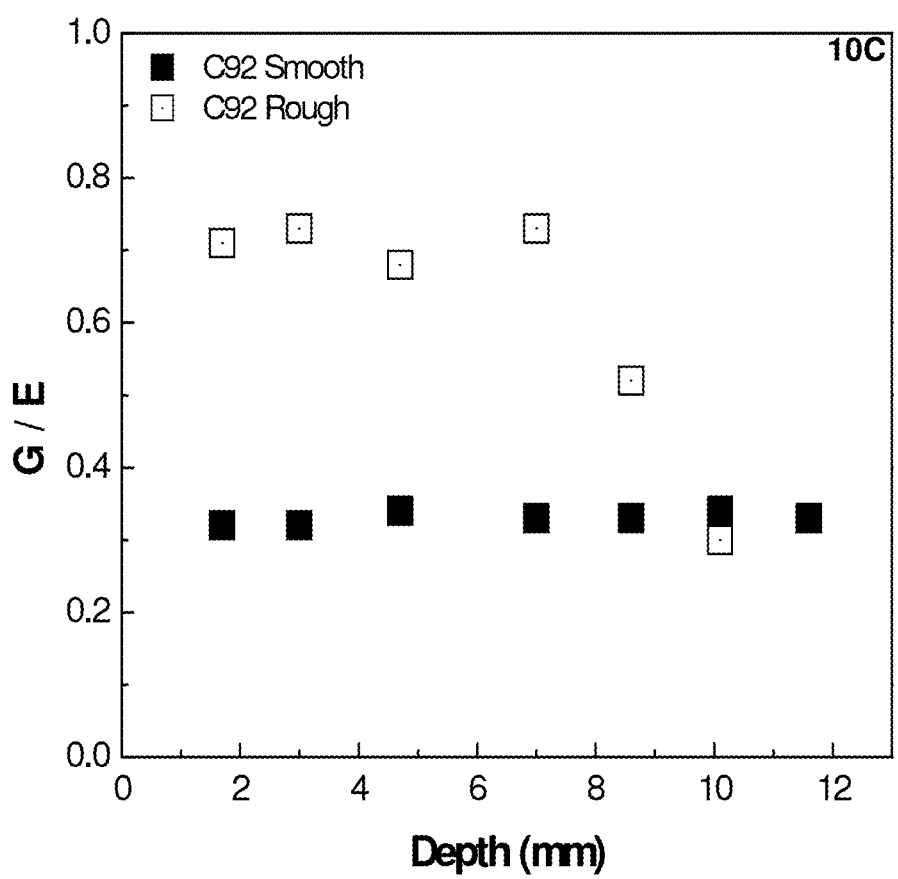
FIG. 10(c) is a graph of G/E ratio as a function of inclusion depth for rough and smooth inclusions made of C92.

FIG. 10(b) shows the measured shear modulus versus depth for the S inclusions (open circles) and the R inclusions (open squares). The shaded horizontal band indicated the value of the shear modulus of the gelatin matrix with its standard deviation. As can be seen, the depth sensitivity for the shear modulus of the S inclusions and the R inclusions were also found to be about 8 mm, similar to the depth sensitivity found when measuring the elastic modulus. In FIG. 10(c), the G/E ratio versus the inclusion depth is plotted for both the S inclusions (open circles) and the R inclusions (open squares). For the S inclusions, the G/E ratio remained around 0.3 as expected for all depths. For the R inclusions, the G/E remained around 0.7 for depths smaller than 8 mm. The value of the G/E ratio decreased when the depth became larger than 8 mm and became 0.3 when the depths were larger than 10 mm. From FIG. 10(c), the depth sensitivity of the present 3.8 mm wide cantilever was around 8 mm, about twice the size of the contact area (which was width of the cantilever.

Example 4

The depth sensitivity of a PEFS array was also investigated. It was found that PEFS arrays have enhanced depth sensitivity in comparison to a single PEFS.

Figure 14A:
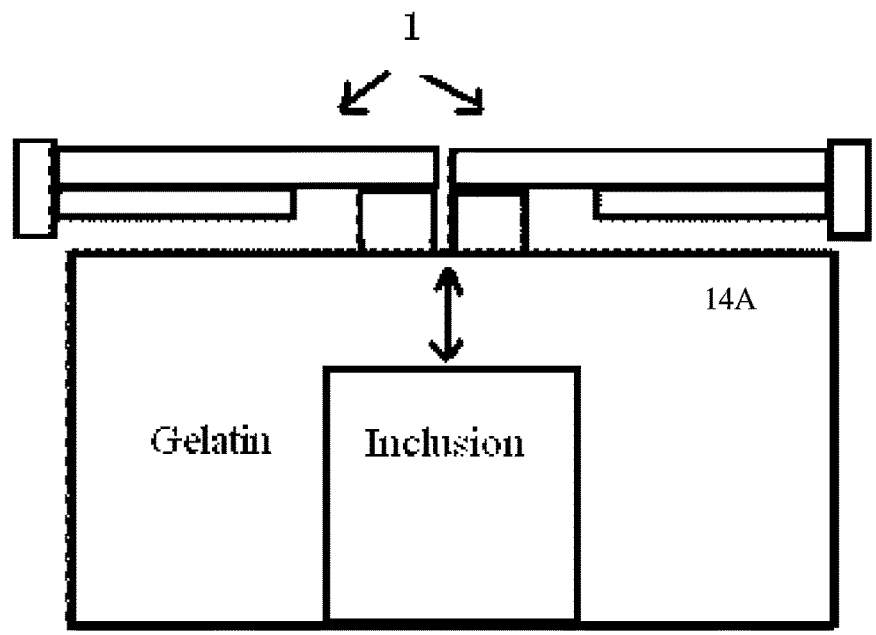
FIG. 14(a) is a schematic of two PEFS performing synchronized Young's modulus measurement above the center of an inclusion embedded in gelatin.
Figure 14B:
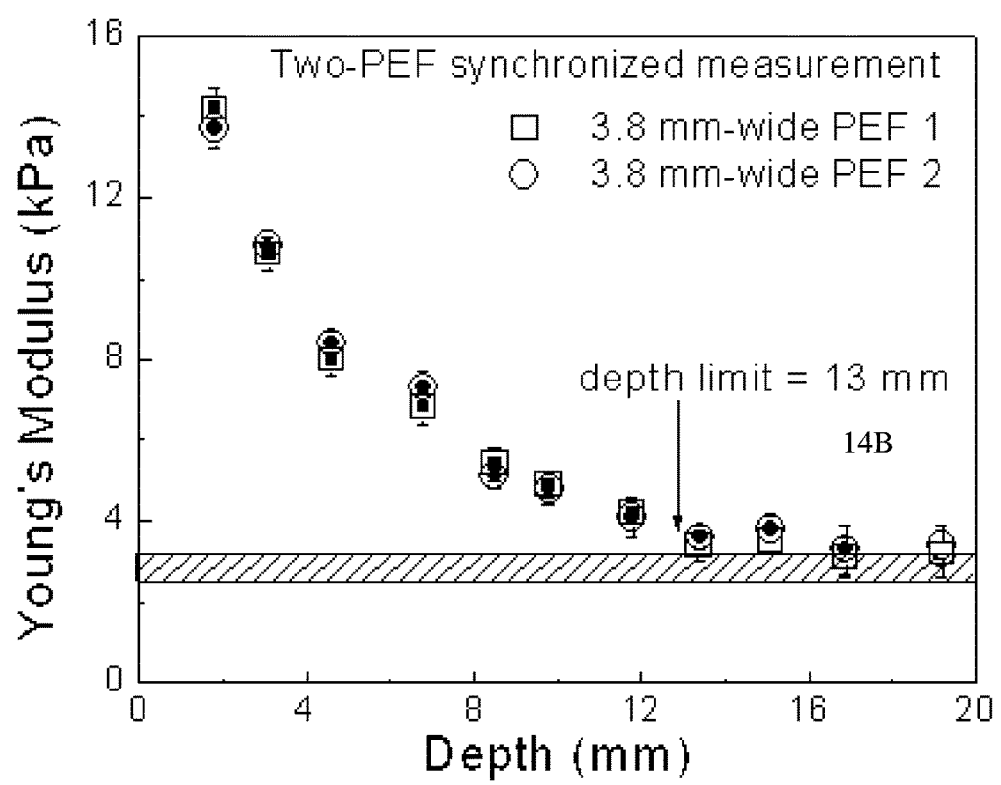
FIG. 14(b) is a graph of elastic modulus as a function of inclusion depth.

The study involved performing depth-sensitivity measurements using an array of two 3.8 mm wide PEFS's. The PEFS's were arranged side by side, as schematically shown in FIG. 14(a), to measure the elastic modulus of an artificial tissue containing modeling-clay inclusions 8 of various depths, similar to those shown in the insert in FIG. 13. The two PEFS's were placed at the center above each model inclusion. The measurements by the two PEFS's were synchronized. That is, the applied voltages to the driving PZT layers of both PEFS's were applied at the same time with the same magnitude. The induced voltages at the sensing PZT layers of the two PEFS's were also measured at the same time. As previously determined in Example 2, the depth sensitivity of a PEFS is about twice the width of the PEFS. By synchronizing the measurements of two neighboring PEFS's, the PEFS array acted as one large PEFS. Therefore the combined width of the PEFS's enhanced the overall depth sensitivity. FIG. 14(b) shows a graph of the measured elastic modulus as a function of measured inclusion depth d obtained from the synchronized PEFS array.

Figure 15A:
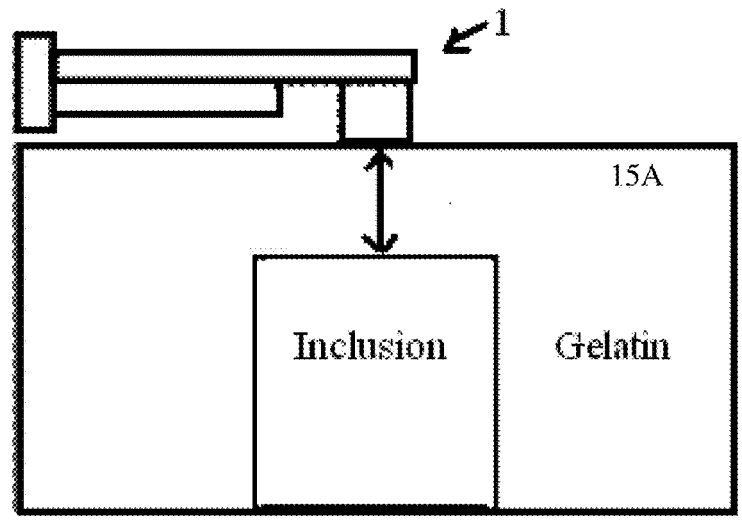
FIG. 15(a) is a schematic of a PEFS performing elastic modulus measurements above the center of an inclusion of depth embedded in a matrix of gelatin.
Figure 15B:
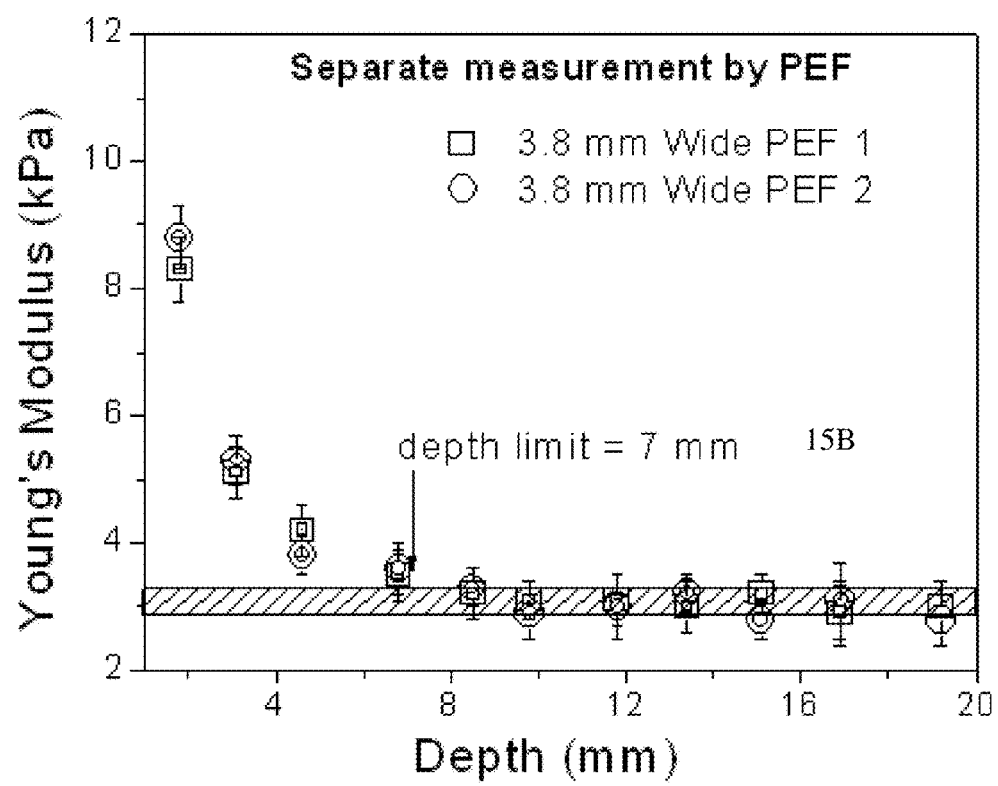
FIG. 15(b) is a graph of elastic modulus as a function of inclusion depth

For comparison, depth sensitivity measurements were also performed using a single PEFS at the center location above the inclusion as schematically shown in FIG. 15(a). FIG. 15(b) shows the elastic modulus as a function of depth for both the PEFS and PEFS array. The synchronized measurements enabled the PEFS array to detect inclusions up to 13 mm in depth, while the single PEFS could only detect inclusions less than 7 mm deep. The results shown in FIGS. 14-15 indicated that the depth sensitivity of the PEFS array doubled, relative to a single PEFS. The depth sensitivity of synchronized PEFS arrays will be roughly twice the width of the contract area of the array.

Example 5

Sample excised breast tissues were evaluated to determine the type, malignancy, invasiveness and depth of the tumor within the tissue samples.

Figures 16A, 16B:
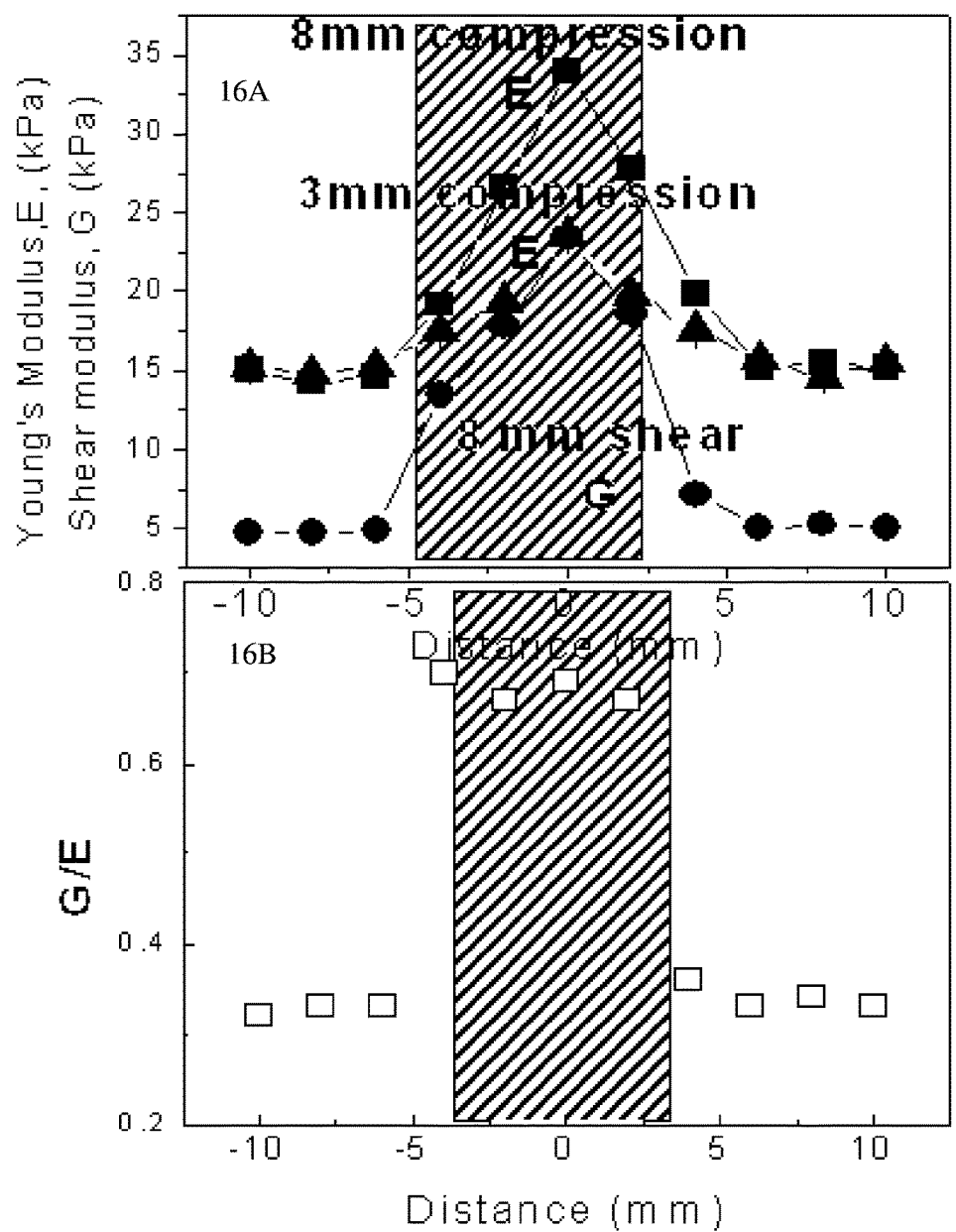
FIG. 16(a) is a graph of elastic modulus (E) and shear modulus (G) profiles as a function of distance for breast tissue.
FIG. 16(b) is a graph of shear modulus to Young's modulus ratio (G/E) profile as a function of distance for breast tissue.

In one portion of the study, the shear moduli of excised breast tissues were measured by indentation shear tests using a 8 mm wide PEFS. FIG. 16(a) shows the shear modulus profile for a sample excised breast tissue containing an invasive and malignant ductal carcinoma. FIG. 16(a) also shows the elastic modulus profile measured with the same PEFS. As can be seen, like the elastic modulus measurement, the indentation shear measurement is capable of detecting the higher shear modulus of the tumor as compared to the shear modulus of the surrounding tissue.

Moreover, the G/E ratio was usable to discern the roughness of the interface between the inclusion 8 and the surrounding matrix 9. In FIG. 16(b), the shear modulus is plotted as a function of the G/E ratio and demonstrates that the G/E ratio of the tumor was well over 0.7 as compared to the G/E ratio of about 0.3 of the surrounding tissue. This result evidences that high G/E ratios greater than about 0.3 may be correlated to invasive cancers.

Figure 17A:
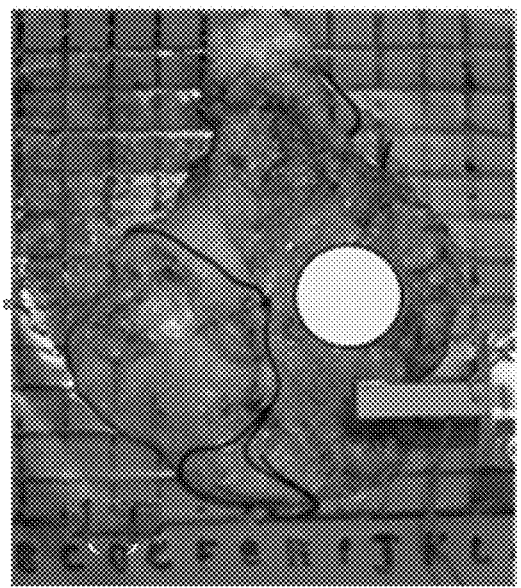
FIG. 17(a) is a photograph of an excised breast tissue containing an invasive ductal carcinoma.
Figure 17B:
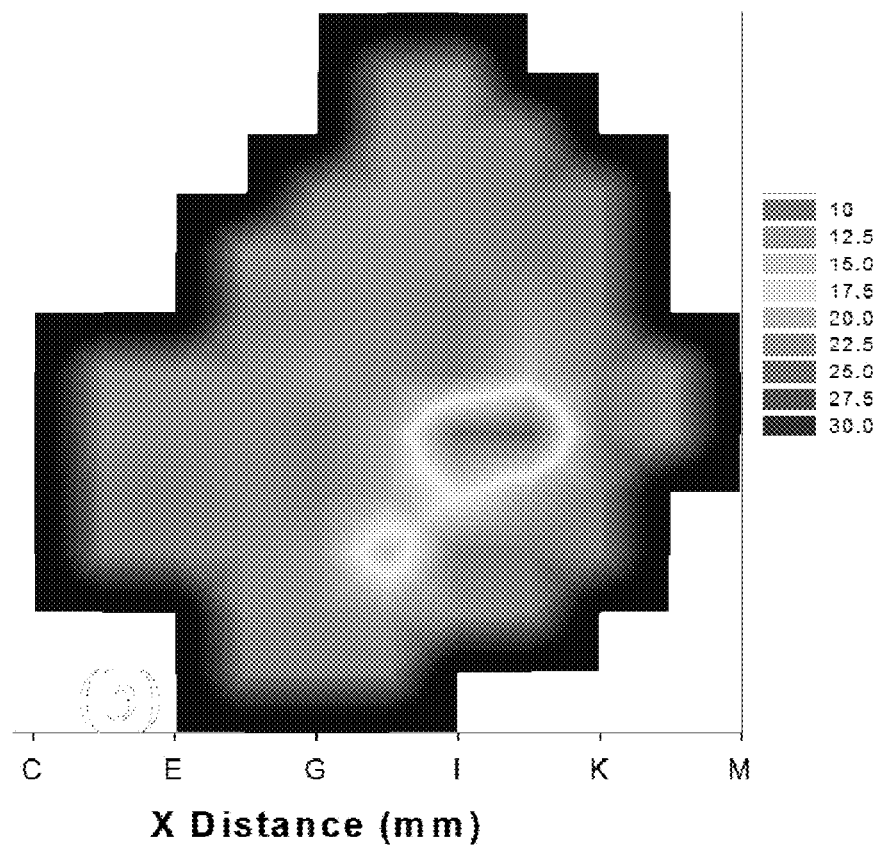
FIG. 17(b) is an elastic modulus (E) scan of the excised breast tissue shown in FIG. 17(a). The elastic modulus appears higher at the tumor site than at the surrounding tissue.
Figure 17C:
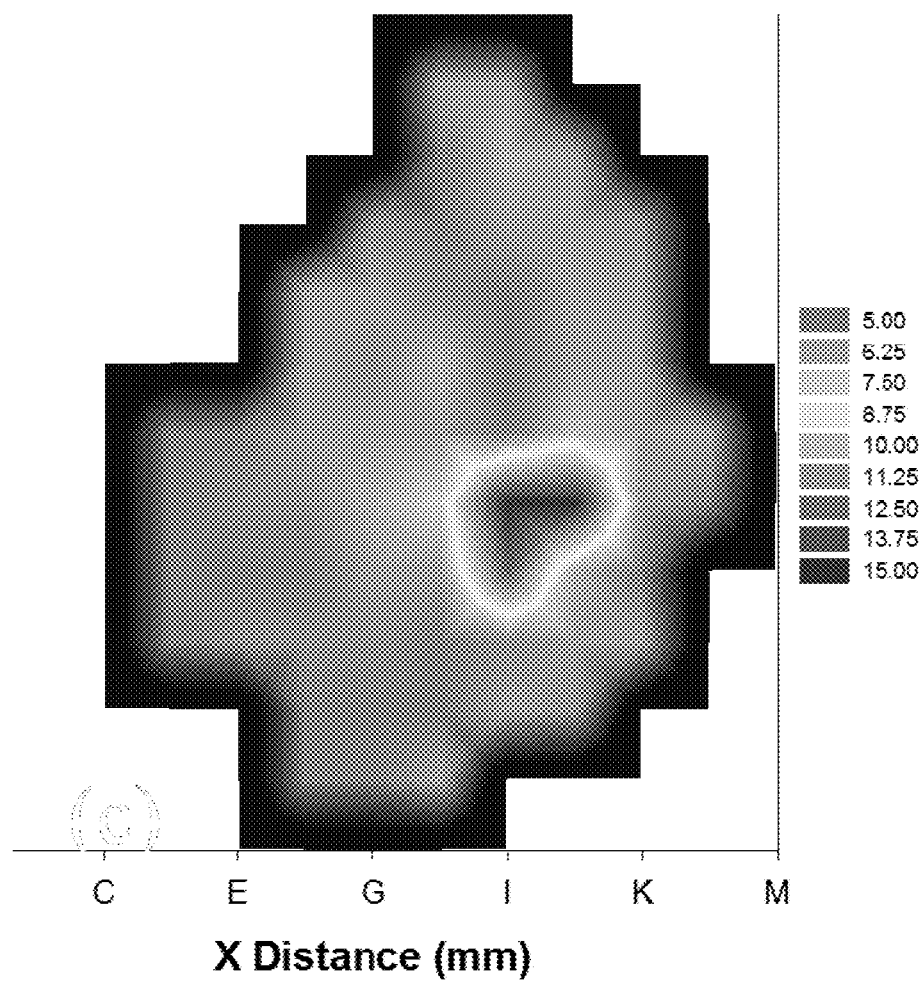
FIG. 17(c) is a shear modulus (G) scan of the excised breast tissue shown in FIG. 17(a). The shear modulus appears higher at the tumor site than at the surrounding tissue.
Figure 17D:
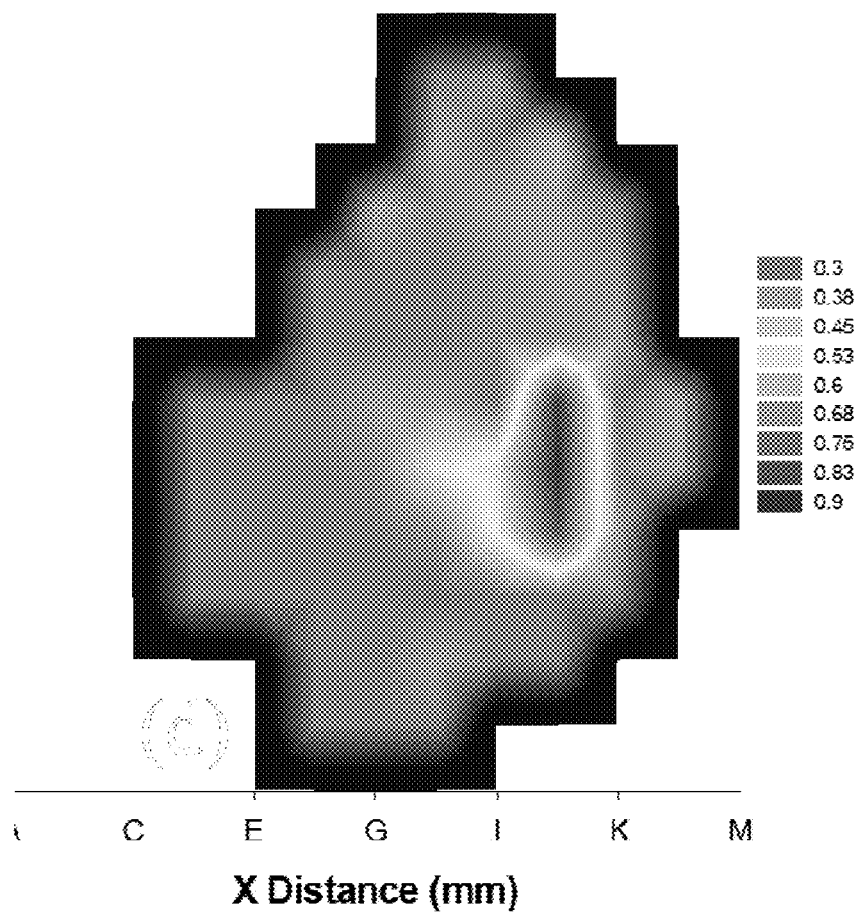
FIG. 17(d) is a G/E scan of the excised breast tissue shown in FIG. 17(a). The G/E value >0.7 indicates that the boundary is rough, typical of invasive ductal carcinoma.

FIG. 17(a) shows an excised breast tissue containing an invasive ductal carcinoma. FIGS. 17(b), 17(c) and 17(d) show the elastic modulus scan, the shear modulus scan and the G/E scan, respectively, where the light color represents low E, G, and G/E values of the surrounding tissues and the dark color represents high E, G, and G/E values. Clearly, both the E and G scans identified the location of the tumor depicted by the dark high elastic modulus and high shear modulus area of the tumor as compared to the surrounding tissue. Furthermore, the G/E for the tumor was >0.7, indicating that the tumor had a rough boundary in comparison to the surrounding tissue, consistent with the invasive nature of an invasive ductal carcinoma.

Figure 18A:
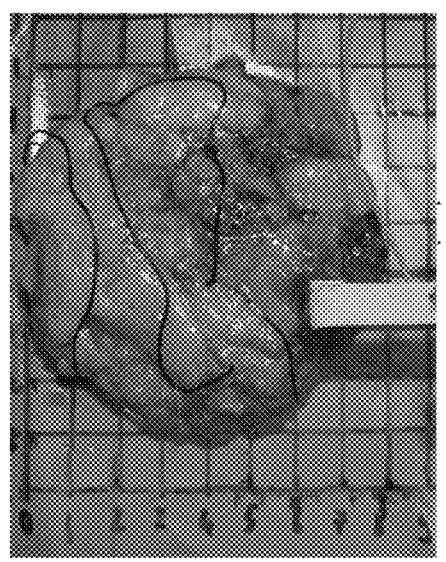
FIG. 18(a) is a photograph of an excised breast tissue containing a ductal carcinoma in situ.
Figure 18B:
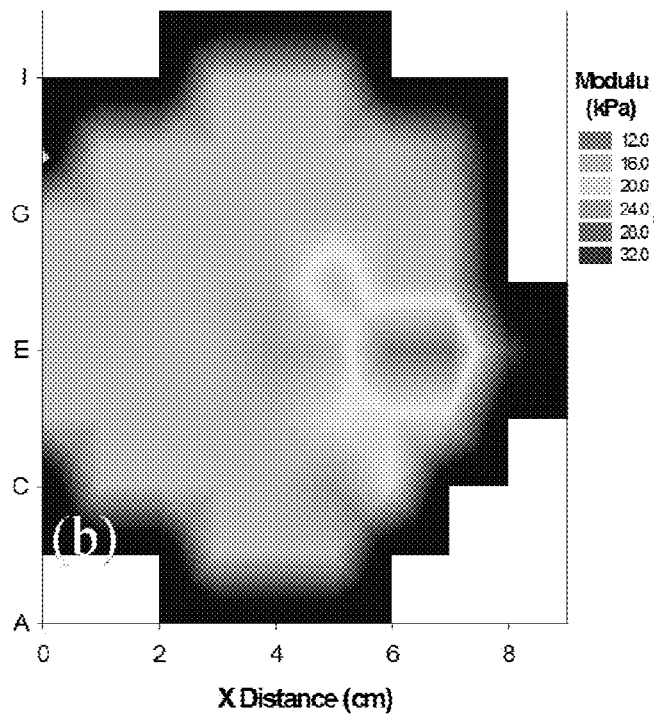
FIG. 18(b) is an elastic modulus (E) scan of the excised breast tissue shown in FIG. 18(a). The elastic modulus appears higher at the tumor site than at the surrounding tissue.
Figure 18C:
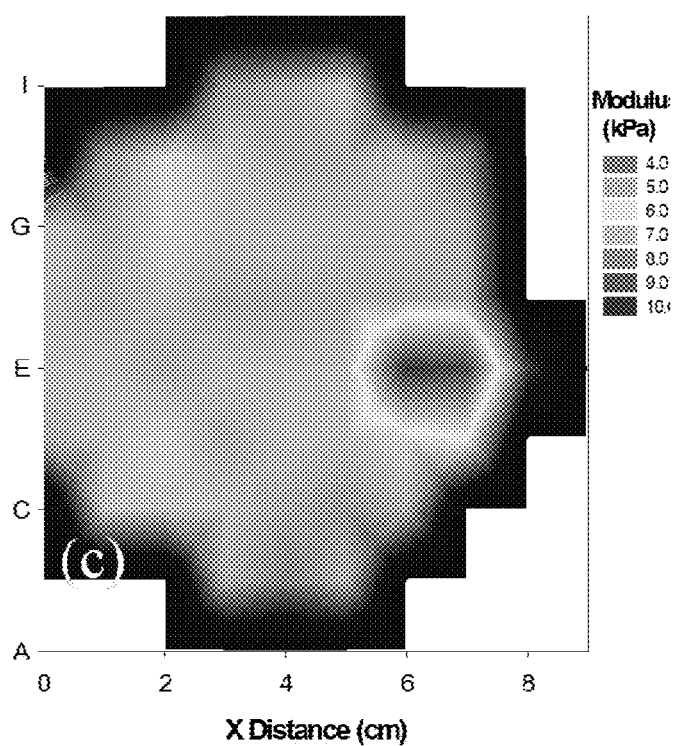
FIG. 18(c) is a shear modulus (G) scan of the excised breast tissue shown in FIG. 18(a). The shear modulus appears higher at the tumor site than at the surrounding tissue.
Figure 18D:
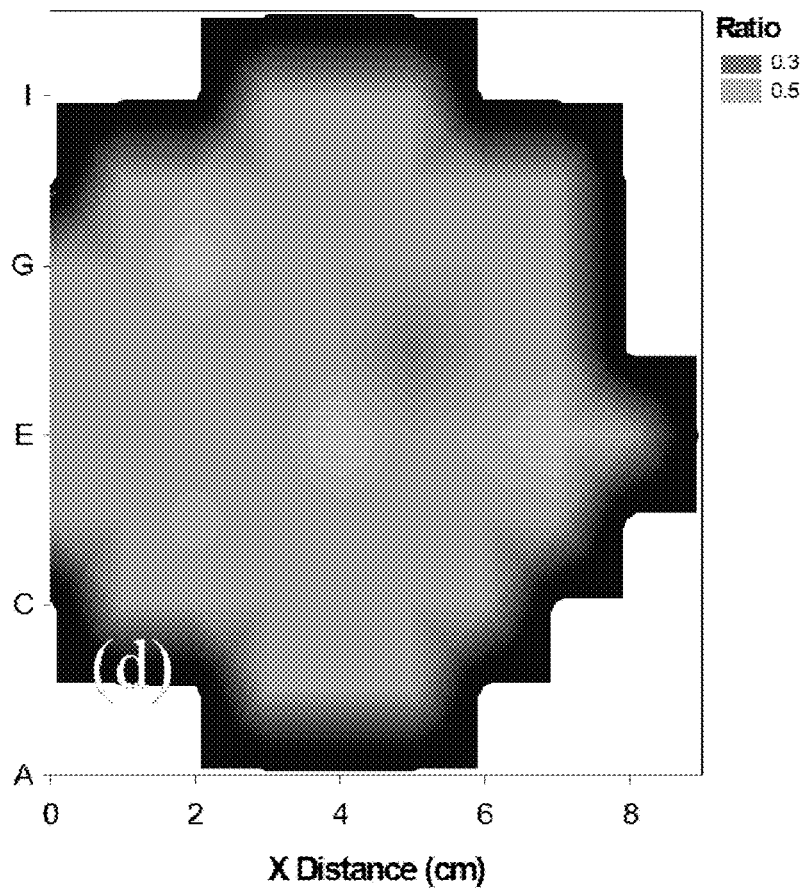
FIG. 18(d) is a G/E scan of the excised breast tissue shown in FIG. 18(a). The tumor G/E value of about 0.3 is consistent with noninvasive ductal carcinoma confined within the milk duct.

FIG. 18(a) shows a photograph of an excised breast tissue containing a ductal carcinoma in situ (DCIS). FIGS. 18(b), 18(c) and 18(d) show the elastic modulus (E) scan, the shear modulus, G, scan, and the G/E scan, respectively. The E and G values were higher at the tumor site than for the surrounding tissue, indicating an abnormality. The G/E ratio was about 0.3 at the tumor site, similar to the G/E ratio of the surrounding tissue, which is consistent with the fact that a ductal carcinoma in situ is confined within the milk duct and is not invasive.

Figure 19A:
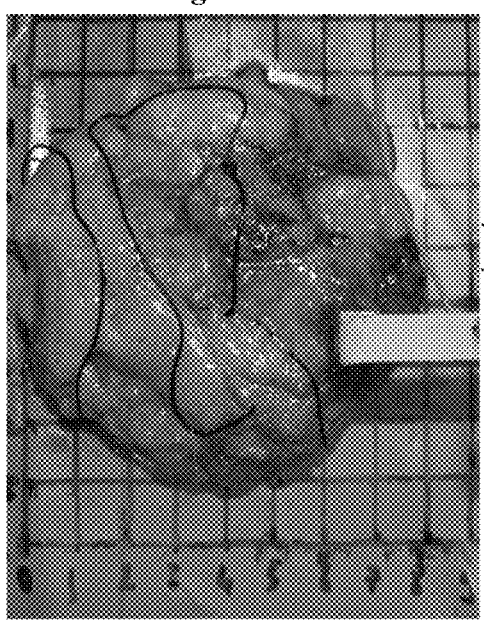
FIG. 19(a) is a photograph of an excised breast tissue containing a hyperplasia.
Figure 19B:
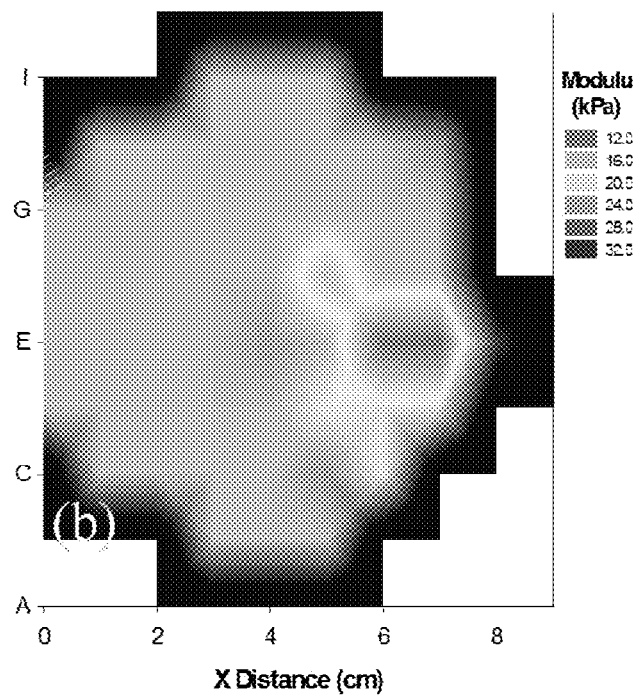
FIG. 19(b) is an elastic modulus (E) scan of the excised breast tissue shown in FIG. 19(a). The elastic modulus appears higher at the tumor site than at the surrounding tissue.
Figure 19C:
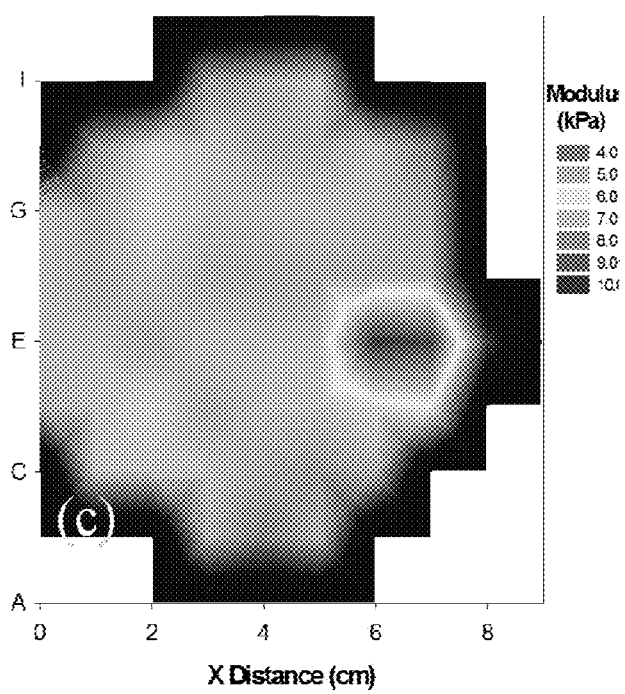
FIG. 19(c) is a shear modulus (G) scan of the excised breast tissue shown in FIG. 19(a). The shear modulus appears higher at the tumor site than at the surrounding tissue.
Figure 19D:
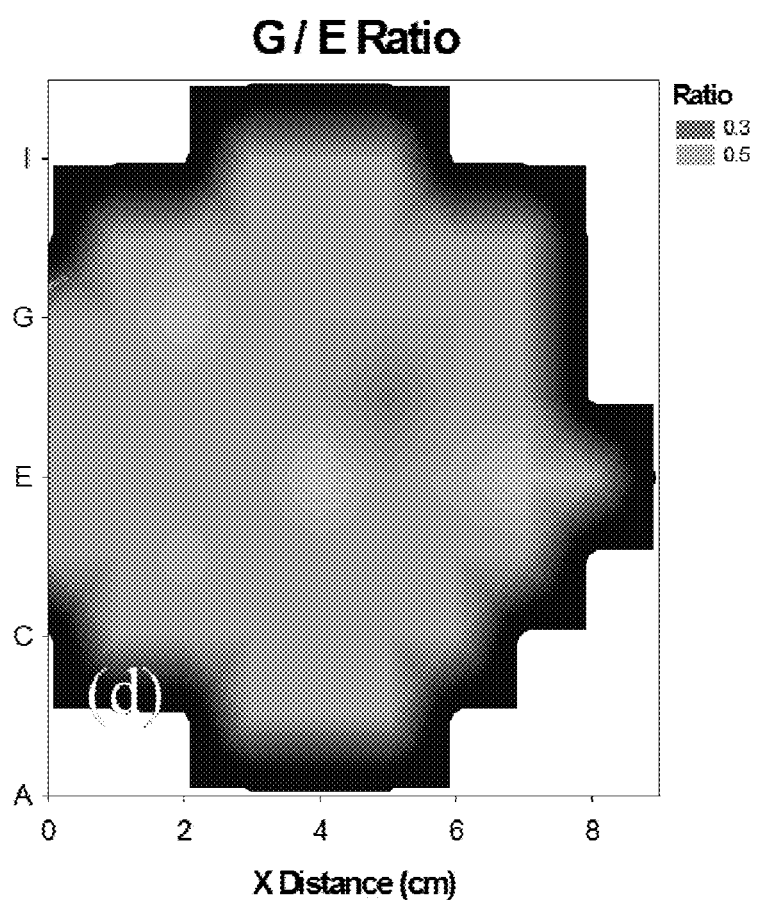
FIG. 19(d) is a G/E scan of the excised breast tissue shown in FIG. 19(a), showing that the G/E value is about 0.5.

FIG. 19(a) shows an excised breast tissue containing a hyperplasia. FIGS. 19(b), 19(c) and 19(d) show the elastic modulus (E) scan, the shear modulus, G, scan and the G/E scan, respectively. The E and G values were higher at the tumor site than for the surrounding tissue, indicating an abnormality. The G/E ratio was about 0.5, indicating that the boundary of a hyperplasia is rougher than a ductal carcinoma in situ but not as rough as an invasive ductal carcinoma.

As noted by the evaluating surgeon, hyperplasia is difficult to identify by palpation. Pathologically, it is an abnormal growth with no clear boundary. Therefore, because a PEFS can detect hyperplasia in both E and G scans and this example has shown that hyperplasia exhibits a different G/E ratio from an invasive ductal carcinoma or a ductal carcinoma in situ, it can be used as a sensitive and robust screening tool for detecting various types of breast abnormalities.

A total of 42 ex vivo breast tissue samples were evaluated and compared to pathology tissue analysis. The types of tumors are listed in Table III.

TABLE III

Distribution of G/E among various breast abnormalities

|  | G/E = 0.3 | G/E = 0.5 | G/E >0.7 | Sub Total |
|---|---|---|---|---|
| Malignant |  |  |  |  |
| Invasive Carcinoma |  |  | 23 | 24 |
| Ductal Carcinoma in situ | 7 |  | 1 | 8 |
| Benign |  |  |  | 10 |
| Hyperplasia |  | 7 | 1 | 8 |
| Fibrocystic | 1 |  |  | 1 |
| Fibroadipose | 1 |  |  | 1 |
| Total |  |  |  | 42 |

The PEFS measurements indicated that invasive carcinoma exhibited a G/E ratio >0.7 (23 out of 24), hyperplasia had a G/E ratio=0.5 (7 out 8), ductal carcinomas in situ had a G/E ratio of ~0.3 (7 out 8) and fibrocystic and fibroadipose exhibited a G/E ratio =0.3 (2 out of 2).

As shown in Table IV, the malignancy of the tumors was also evaluated in terms of the G/E ratio of the tissue samples.

TABLE IV

Malignancy Analysis

|  | Malignant | Benign |  |
|---|---|---|---|
| G/E = 0.3 or >0.7 | 32(TP) | 3(FP) | 35(TP + FP) |
| G/E = 0.5 | 0(FN) | 7(TN) | 7(FN + TN) |
| Total | 32(TP + FN) | 10(FP + TN) | 42(TP + FP + TN + FN) |

Using a G/E ratio >0.7 or equal to 0.3 as a criterion for malignancy, the sensitivity for malignancy was 100% (32 out of 32). The specificity was 70% (7 out 10), and the accuracy was 93% (39 out 42). The positive prediction value was 91% (32 out of 35), and the negative prediction value was 100% (7 out 7). These results are listed in Table V, below.

TABLE V

Statistics of 42 excised breast tissues

|  | Sensitivity | Specificity | Accuracy | PPV* | NPV** |
|---|---|---|---|---|---|
| Malignancy | 100% (32/32) | 70% (7/10) | 93% (39/42) | 91% (32/35) | 100% (7/7) |
| Invasiveness | 96% (23/24) | 89% (16/18) | 93% (39/42) | 92% (23/25) | 94% (16/17) |

As can be seen, the PEFS achieved 100% sensitivity, 70% specificity, and 93% accuracy for malignancy.

TABLE VI

Invasiveness analysis

|  | Invasive | Non-invasive |  |
|---|---|---|---|
| G/E >0.7 | 23(TP) | 2(FP) | 25(TP + FP) |
| G/E <0.7 | 1(FN) | 16(TN) | 17(FN + TH) |
| Total | 24(TP + FN) | 18(FP + TN) | 42(TP + FP + TN + FN) |

In addition, using a G/E ratio of >0.7 as a criterion, it was also possible to differentiate invasive tumors, such as invasive carcinoma, from non-invasive tumors, such as ductal carcinoma, as shown in Table VI above. The sensitivity was 96% (23 out 24); the specificity was 89% (16 out 18); and the accuracy was 93% (39 out 42). The positive prediction value was 92% (23 out 25), and the negative prediction value was 94% (16 out 17). These results are also listed in Table V. As can be seen, PEFS achieved 96% sensitivity, 89% specificity, and 93% accuracy for predicting invasive carcinoma.

Additionally, as part of the study, two PEFS's of different widths were used to perform elastic modulus profile measurements on the same tumor to determine the tumor depth and tumor elasticity simultaneously without simulations. FIG. 16(a) shows the elastic modulus profile of a tumor using an 8 mm wide and 3 mm wide PEFS. From FIG. 16(a), one can see that using two PEFS's of different widths, the resultant elastic modulus profiles were different due to the different depth sensitivity limits of the two PEFS's. From the two elastic modulus profiles, it was possible to deduce the elastic modulus, $E_t$, and depth of the tumor, d, using the following equations:

$$\frac{d_1}{E_1} = \frac{d}{E_n} + \frac{d_1 - d}{E_t}, \quad (5)$$

and $$\frac{d_2}{E_1} = \frac{d}{E_n} + \frac{d_2 - d}{E_t}, \quad (6)$$

$d_1$ and $d_2$ are the depth sensitivity limits and $E_1$ and $E_2$ are the measured elastic modulus of PEFS 1 and PEFS 2, respectively, and $E_n$ is the elastic modulus of the normal breast tissues. Using the measured elastic modulus over the center of the tumor, using the depth sensitivity limits and $E_n$ obtained from a flat tissue region located a distance from the tumor, it was possible to determine that d=5 mm and $E_t$=68 kPa. The lateral size of the tumor was 6 mm, as estimated from the lateral elastic modulus and shear modulus profiles.

Example 6

The ex vivo breast tissue experiment of Example 5 above was subsequently continued, the resulting data for which is provided below. In total 71 breast tissue samples were evaluated and compared to pathology tissue analysis.

Figure 20:
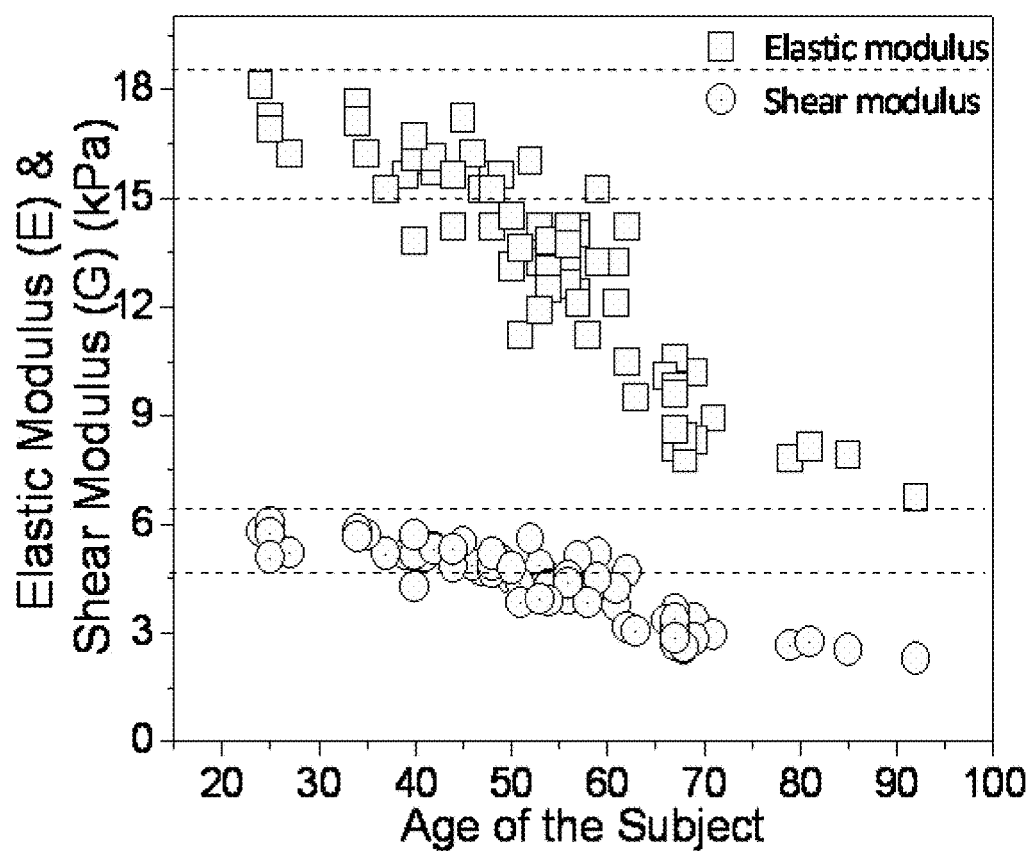
FIG. 20 is a graph of elastic and shear modulus of normal breast tissue as a function of patient age.

FIG. 20 shows a graph of E and G of the normal breast tissues of the 71 breast tissue samples as a function of patient age. As can be seen, both the E and G varied with age with younger women exhibiting both a higher E and a higher G. The E of the normal breast tissue was about 18 kPa for women who were about 24 and about 18 to about 15 kPa for women who were 24-40 Similarly, the G of the normal breast tissue was about 6 to about 5 kPa for women were 24-40 and decreased to about 3 kPa for women about 90 years old. The results demonstrate a strong correlation between the values of E and G of normal breast tissue and patient age, with younger women exhibiting higher E and G.

The average E and G of the normal breast tissues of all 71 samples was $E_{n,ave}$=13±3 kPa, and $G_{n,ave}$=4.4±1 kPa, where n denotes normal tissue. Of the 71 cases, there were 33 cases of invasive carcinoma (IC) (32 cases of invasive ductal carcinoma and 1 case of invasive lobular carcinoma), 9 cases of ductal carcinoma in situ (DCIS), and 19 cases of benign conditions (BC) including fibrocystic, hyperplasia, calcifications, fibroadenoma, papilloma, and glandular tissues.

Figure 21A:
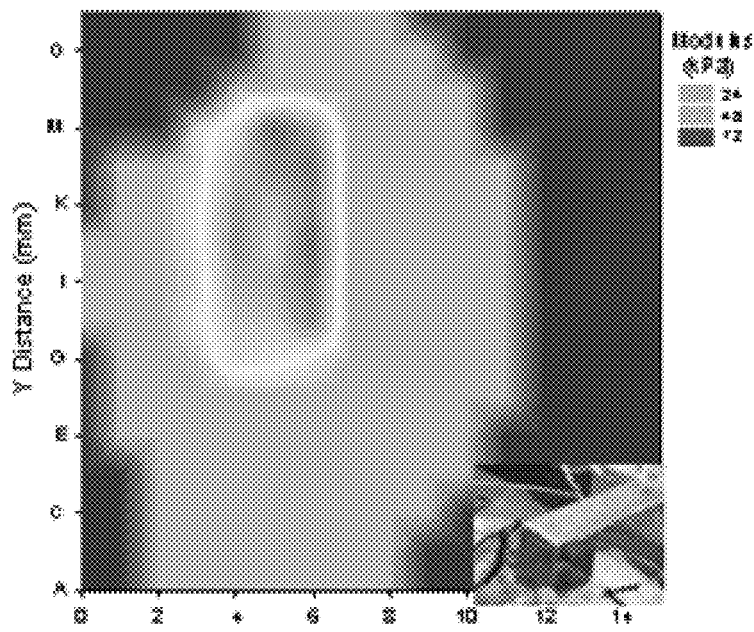
FIG. 21(a) is the E map of a mastectomy tissue sample.
Figure 21B:
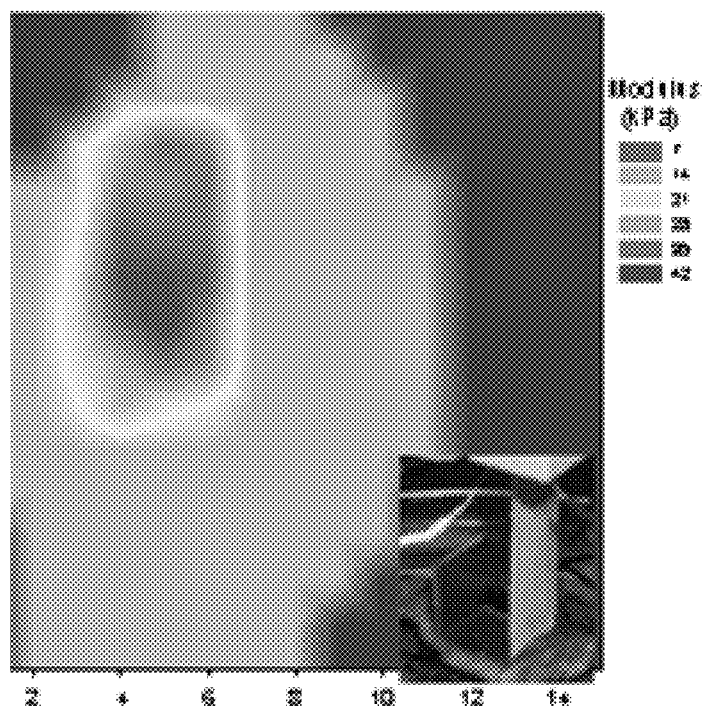
FIG. 21(b) is the G map of a mastectomy tissue sample.
Figure 21C:
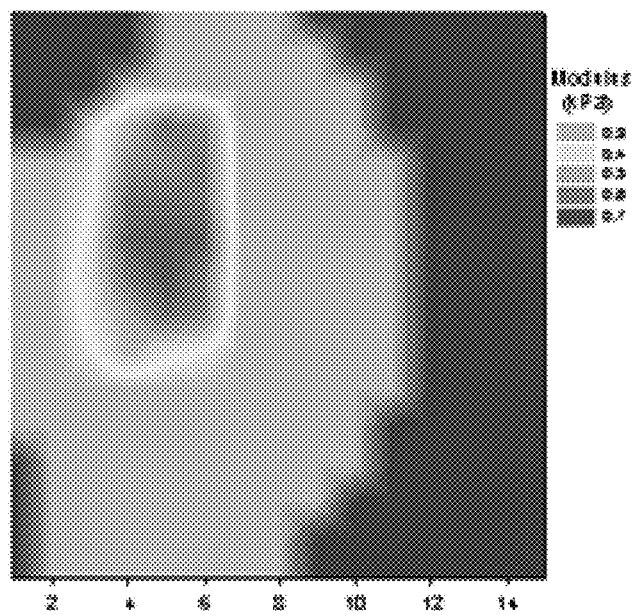
FIG. 21(c) is the G/E map of a mastectomy tissue sample.

As an example, FIGS. 21(*a*)-21(*b*) show the E map of a mastectomy sample with an insert showing a PEF in the E measurement configuration, and the G map with an insert showing the PEF in a G measurement configuration, respectively. In the E and G maps shown in FIGS. 21(*a*) and 21(*b*), respectively, the light colored region represented the E or G of the normal breast tissues and the dark colored region indicated abnormally high E and G signature of abnormal tissues. Clearly using the contrast in the E or G map, one could locate the abnormal tissue within the excised sample and determine the size of the abnormal region. Both the E and G are higher at the tumor site, an invasive ductal carcinoma exhibits a G/E>0.7, than at the surrounding tissue. With such detection strategy, PEFS has exhibited remarkably high detection sensitivity for abnormal breast tissues, namely about 100% sensitivity with p<0.01 for the entire age group (age 24-90), for women under 40 and for women with normal breast tissue elastic modulus and shear modulus similar to those of women under 40 (about 35% of the 71 cases were examined).

Figure 22:
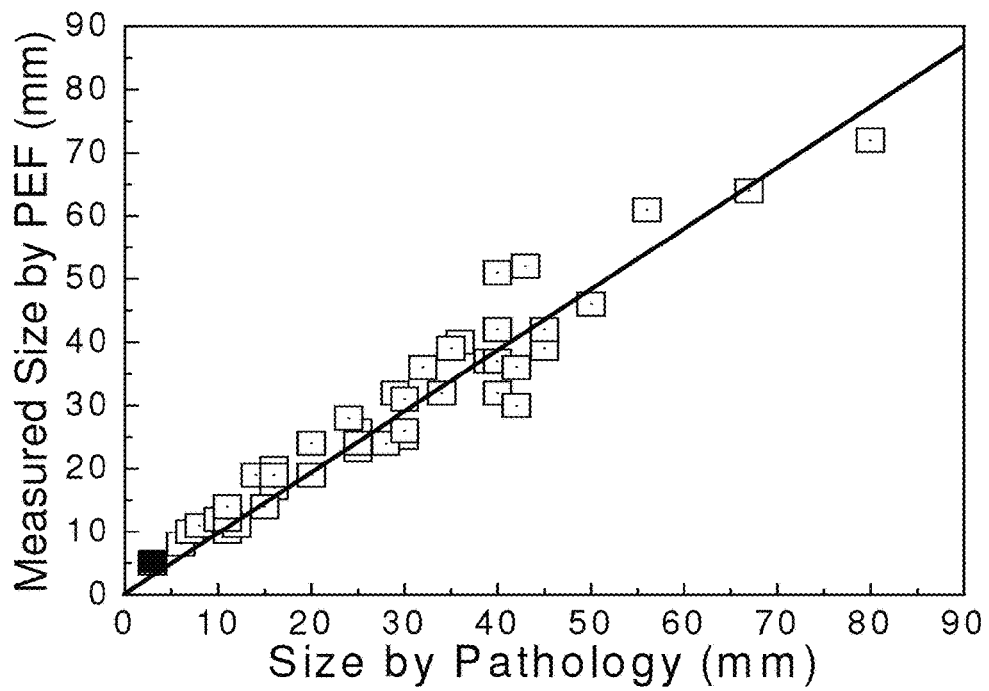
FIG. 22 is a graph of tumor size measurements obtained by using the PEFS versus tumor size measurements obtained by pathology.

The PEFS was also found to be effective in accurately determining tumor size. FIG. 22 shows a graph comparing the tumor size measurements using the PEFS and tumor size determined by pathology. The results were statistically the same. It is important to note that 26 of these samples included skin and nipple. Therefore, the results demonstrate that the presence of skin and nipple did not affect the quality of the PEFS measurements. Table VII shows the average measured values of E and G for carcinoma in situ (CIS), IC and benign tumors. As can be seen, these values are 3-5 times that of the normal breast tissues, regardless of patient's age.

TABLE VII

|  | CIS | IC | Benign |
| --- | --- | --- | --- |
| Elastic Modulus (E) | 62 ± 10 kPa | 55 ± 9 kPa | 44 ± 12 kPa |
| Shear Modulus (G) | 23 ± 10 kPa | 40 ± 10 kPa | 24 ± 10 kPa |
| p value | <0.01 | <0.01 | <0.01 |

Table VIIII shows that different type of tumors exhibited different G/E ratios. For example, the dark colored region in FIG. 21(*c*) indicated G/E>0.7 which corresponded to IC.

TABLE VIIII

|  | G/E = 0.3 | G/E = 0.5 | G/E >0.7 | Sub Total |
| --- | --- | --- | --- | --- |
| Malignant | 10 | 2 | 35 | 47 |
| Invasive Carcinoma | 2 | 2 | 34 | 38 |
| Carcinoma in situ | 8 |  | 1 | 9 |
| Benign | 6 | 13 | 5 | 24 |
| Total | 16 | 15 | 40 | 71 |

Thus, as shown in Table IX, with G/E>0.7 alone and G/E>0.7 or G/E=0.3, it was possible to predict invasive carcinoma and malignant tumors (including both IC and CIS) with 89% sensitivity and 82% specificity, and 96% sensitivity and 54% specificity, respectively.

TABLE IX

|  | Sensitivity | Specificity |
| --- | --- | --- |
| Malignancy | 96% (45/47) | 54% (13/19) |
| Invasiveness | 89% (29/33) | 82% (24/28) |

Of the 71 ex vivo breast tissue samples, 25 cases had a high elastic modulus and shear modulus, as shown in FIG. 20, representative of mechanically dense breast tissue. As discussed above, the detection sensitivity of abnormalities in these 25 cases with mechanically dense breast tissue was also 100%. Moreover, using the same G/E criteria discussed above, a diagnosis of invasive carcinoma in these 25 samples was determined with 93% sensitivity and 80% specificity and a diagnosis of malignancy in these 25 samples was determined with 94% sensitivity and 63% specificity (see Table X), which was essentially the same sensitivity and specificity as for the entire age group. This data further supports the conclusion that PEFS were able to detect breast tumors in dense breast tissue as well as in other breast tissue.

TABLE X

|  | Sensitivity | Specificity |
|---|---|---|
| Malignancy | 94% (16/17) | 63% (5/8) |
| Invasiveness | 93% (14/15) | 80% (8/10) |

Example 7

The use of the PEFS in excised breast tumors has been evaluated in the laboratory. A lumpectomy specimen was taken from a 60-year old woman with breast cancer. The known malignancy was 1.4 cm in the largest dimension. After surgical excision, the specimen was oriented with silk sutures, scanned with ultrasound, and images were stored. The PEFS scan was performed in the same orientation to allow later correlation with the ultrasound image. The specimen was sectioned in the same orientation to allow histological confirmation of the PEFS findings as well. Using the PEFS, preliminary elastic modulus measurements were performed on breast lumpectomy samples using an 8 mm wide PEFS with a rectangular tip. A lateral elastic modulus profile of a lumpectomy sample, measured with an 8 mm wide PEFS, was able to distinguish cancerous tissue from the surrounding tissues. The PEFS scan was able to identify a large 15×13×12 mm invasive ductal carcinoma and a smaller 6×5×3 mm satellite invasive ductal carcinoma. Notably, this smaller lesion was not detected by mammogram, ultrasound or the physician's preoperative palpation. The location and size of the detected tumors were verified by pathology measurements.

Example 8

Figure 23A:
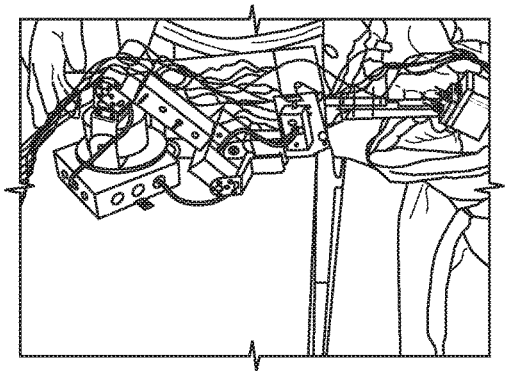
FIG. 23(a) is a photograph of a 4×1 compressive PEF array prototype with a robotic arm performing measurements on the right breast of a patient on her back.
Figure 23B:
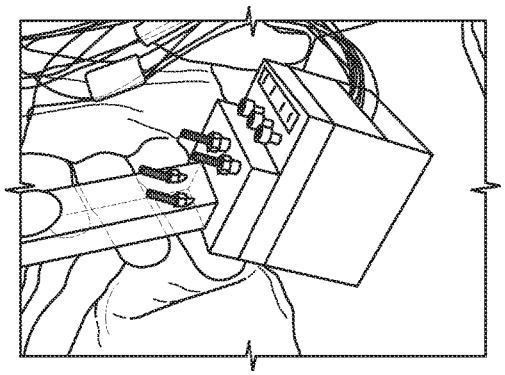
FIG. 23(b) is a photograph of the PEFS array of FIG. 23(a).
Figure 24:
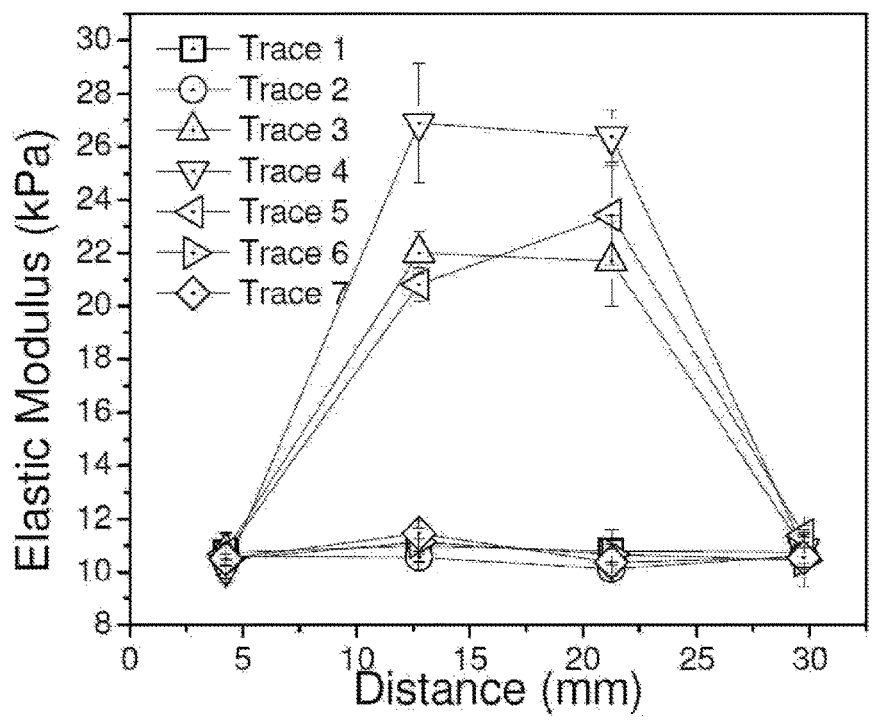
FIG. 24 is a graph of elastic modulus as a function of position on a tissue.

A 51 year old patient with a possible breast tumor on the right side (10 o'clock) of her right breast was examined. Mammography missed the tumor. FIG. 23(a) shows a robotic arm positioning a PEFS array on the patient's breast while the patient was in a supine position. The PEFS array is constructed from 4 individual PEFS sensors as shown in FIGS. 26(a)-26(d). A close-up of the PEFS array is shown in FIG. 23(b). The patient's skin was marked with 7 reference labels at 10 mm intervals indicating the position of the tumor. The PEF array was moved over the reference labels from left to right. The measurements were carried out with one PEFS at a time. The depth sensitivity limit was about 2 cm. FIG. 24 shows the measurements obtained by the PEFS. The elastic modulus of the tumor region was about 28 kPa whereas the elastic modulus of the rest of the area was about 10-11 kPa. Based on this information, it was deduced that the tumor was about 2.5 cm×1.7 cm, which was close to the actual 2.5 cm size of the tumor that was determined by pathology.

The same tumor was also evaluated using two PEFS' in sync. The elastic modulus measurement over the tumor with two PEFS' in sync was about 38 kPa. The elastic modulus of normal breast tissue also increased, indicating that when two PEFS' were operated in sync, the measurements also include part of the chest wall due to the doubling of depth sensitivity. This suggests that the depth sensitivity of the PEFS array was adequate.

Both the PEFS and PEFS array successfully located the tumor and the PEFS array accurately determined its size. Additionally, the patient noted no discomfort during the procedure.

Example 9

Figure 25:
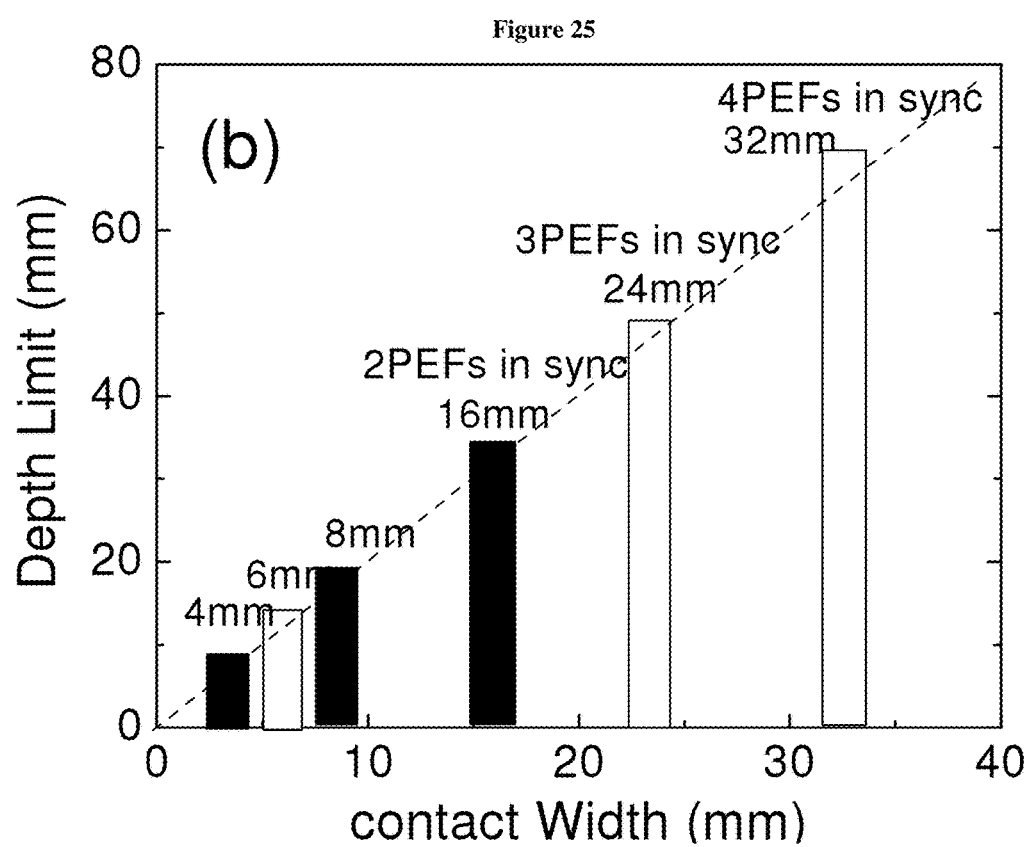
FIG. 25 is a graph of depth sensitivity versus width/contact area of the PEFS or PEFS array.

FIG. 25 shows the depth detection sensitivity of a plurality of PEFS and PEFS arrays having different dimensions. The results show that these PEFS and PEFS arrays demonstrated a depth sensitivity of about twice the width of the respective PEFS and PEFS array. As can be seen in FIG. 25, an array of four 8 mm wide PEFS' that were operated in sync, having a combined width of about 32 mm, showed a depth sensitivity as high as about 63 mm, which is twice the width of the tissue contact area.

Example 10

Figure 26A:
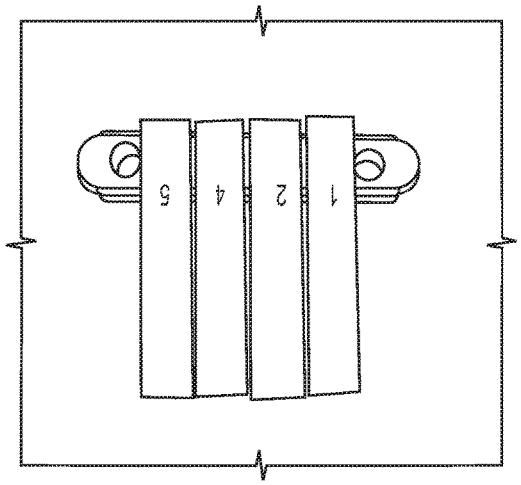
FIG. 26(a) shows an array of 4 PEFS ready to be assembled.
Figure 26C:
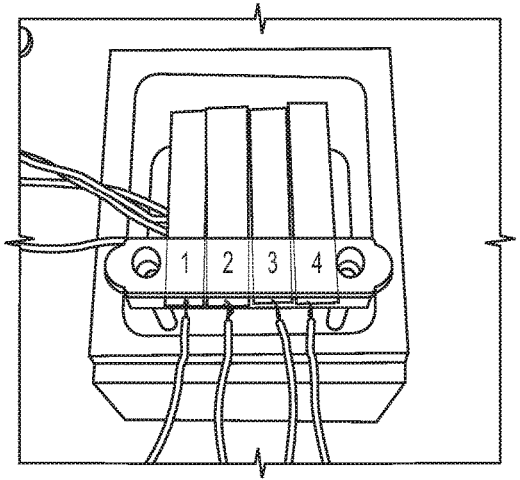
FIG. 26(c) shows the top of the holder of FIG. 26(b).
Figure 26B:
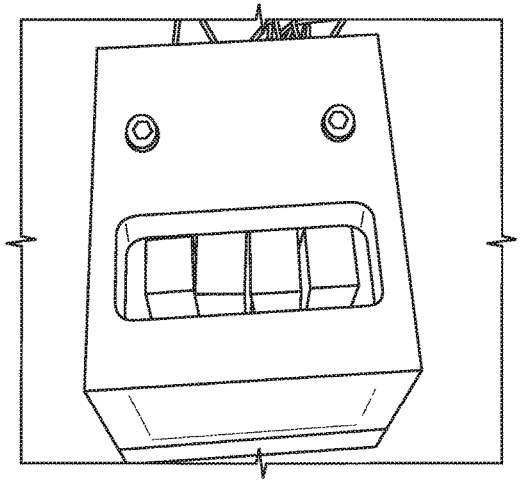
FIG. 26(b) shows the PEFS array of FIG. 26(a) clamped in position in the holder.
Figure 26D:
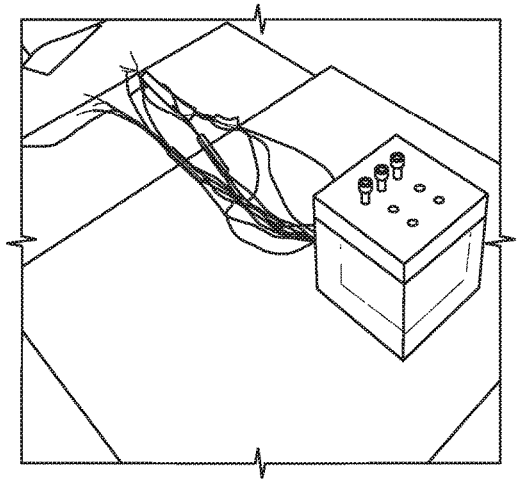
FIG. 26(d) shows the bottom of the holder of FIG. 26(b).

To decrease the scan time for patient screening and improve the device performance, a PEFS system including an n×1 PEFS array having a contact area of about 4-10 cm, a portable measurement unit and a robotic arm for automatic rapid scanning can be constructed. Each PEFS will be about a 3 cm long and about 8-10 mm wide and will have a top PZT layer 3 cm long, 8-10 mm wide and 127-μm thick (T105-H4E-602, Piezo Systems Inc., Cambridge, Mass.) for force application and a 2-cm long bottom PZT layer of the same thickness and width for sensing. The top and bottom PZT layers may be bonded to a 50-μm thick stainless steel layer (Alfa Aesar, Ward Hill, Mass.) of the same width in the middle using a nonconductive epoxy (Henkel Loctite Corporation, Industry, Cailf.) cured at room temperature for one day. The tip of the stainless steel middle layer will be fashioned into a square loop at the free end with each side of the square equal to the width of the cantilever to facilitate both compression and shear measurements. The PEFS' will be clamped inside a holder, shown in FIGS. 26(a) and 26(b), with a top that can be screwed on, as shown in FIG. 26(c), and a bottom that can also be screwed on, as shown in FIG. 26(d), to help protect the PEFS' and flatten the breast surface to ensure a full contact between the PEFS' surfaces and the breast for measurement accuracy.

For elastic modulus measurements, the PEFS' of the array will be oriented parallel to the tissue surface and will be positioned horizontally, similar to FIG. 23(a). To measure the shear modulus, the PEFS' of the array will be oriented perpendicular to the tissue surface. The arrangement of the PEFS array will be such that the contour of the contact area of the array best matches that of the contour of the breasts. The size of the array may vary to best adapt to breasts of different sizes.

The PEFS' array will be used to scan excised tissues to obtain E and G maps. From the E or G maps, it will be possible to determine the tumor size using the width at half peak E or G value. For determination of tumor depth, two PEFS' of different contact areas in an array will be used to take measurements at the same location. The type of tumor, and the malignancy and invasiveness of the tumor will be correlated with the obtained G/E ratio, and the size, location, and tumor type will be compared with the results of ultrasound and pathology for validation To establish that the PEFS' array can detect breast cancers in young women and women with mammographically dense breasts, PEFS' measured normal-tissue elastic and shear modulus in the ex vivo samples will be compared with breast density determined by mammography.

The PEFS will also be used to probe patients. Accuracy for detection of cancerous versus non-cancerous tissue, tumor margins, and tumor centers as well as normal-breast tissue elastic modulus and shear modulus will be determined. The abnormality detection efficacy in women with pathology of all types, breast sizes and densities will be evaluated. PEFS scan will be correlated with the histological sections to confirm the borders of the tumor and characteristics of the normal and malignant tissue. The experiment will also compare in vivo as well as ex vivo normal-tissue E and G obtained using the PEFS with the patient's mammographic density. The in vivo and ex vivo results tumor size and location, and tumor type will also be compared.

Example 11

Three PEFS' were used to determine the precise location and position of an inclusion, representative of abnormal tissue, in a gelatin tissue sample model. The cantilevers were built with Lead Zirconate Titanate (PZT) sheets, 127 microns thick, (T105-H4E-602, Piezo Systems, Inc., Cambridge, Mass.) and stainless steel 304 foil, 50 microns thick (Alfa Aesar, Ward Hill, Mass.).

The two layers of sample model had a total thickness of 2 mm Because the probes are to measure into but not further than the bottom "fat" layer of the model, the probes have diameters inside the range of 0.5 mm to 1 mm. To determine $T_{skin}$, $E_{skin}$, and $E_{fat}$, three cantilevers with three different probe contact areas are used. The cantilevers have varying probe contact areas in order to achieve depth sensitivities in the range of human skin. Table XI below shows the probe sizes and the resulting sensing depth for each of the three cantilevers. Probes for the cantilevers were made from galvanized steel wire (24, 22, and 20 gauge). The wires were cut with wire cutters to lengths of about 2 mm and glued to the free end of the cantilevers with superglue as follows:

TABLE XI

| | Probe Contact Diameter (mm) | Sensing Depth (mm) |
|---|---|---|
| Cantilever A | 0.559 | 1.118 |
| Cantilever B | 0.711 | 1.422 |
| Cantilever C | 0.914 | 1.828 |

A k value under 175 N/m gives the cantilevers the proper flexibility to comply with skin and keeps the strain that the sample/patient must endure to a minimum (<10%).

Figure 28:
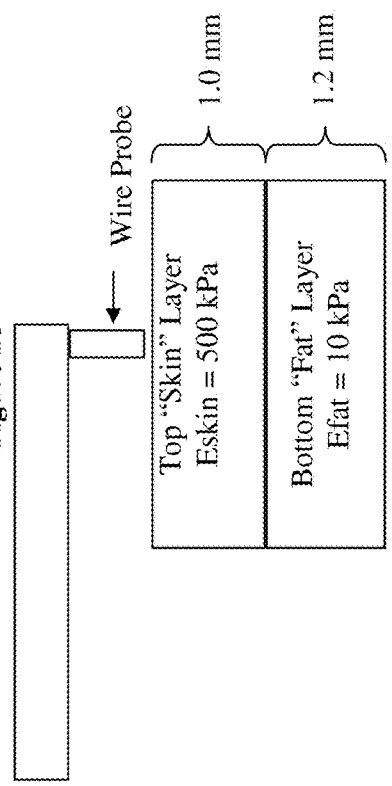
FIG. 28 is a diagram illustrating the examination of a tissue model having a top skin layer and a lower fat layer with a PEFS.

FIG. 28 is a diagram of the skin model used to demonstrate measurement of $T_{skin}$, $E_{skin}$, and $E_{fat}$. The model is made with materials that exhibit properties of human skin (Versaflex CL300 from GLS Corp, E=500 kPa) and subcutaneous fat (Lab Gelatin Type B, E=10 kPa). These materials meet our criteria for the model to have the proper E for skin on the top layer and E for fat on the bottom layer. Measuring $E_{skin}$, $E_{fat}$, and $T_{skin}$.

E is measured using an indentation test. Applying voltage to the driving layer of PZT moves the probe into the sample a distance, d. Because induced voltages ($V_{in}$) in the sensing PZT layer are linear to displacement of the free end of the cantilever we the induced voltages can be correlated to displacement, d. Induced voltages and displacements resulting from a range of applied voltages with and without a sample under the probe will be measured with an oscilloscope and a laser displacement meter respectively. The resistive force that the sample exerts back on the probe inhibits the displacement resulting from the applied voltage. $V_{in,o}$ (the induced voltage with no sample) and $V_{in}$ (the induced voltage with a sample) for several applied voltages ($V_a$) are used to calculate effective modulus ($E_{eff}$) of the entire sample (not individual layers). E is related to $V_{in}$ by the following equation:

$$E_{eff} = \frac{x}{V_{in}} \text{ where } X = \frac{1}{2}\left(\frac{\pi}{A}\right)^{1/2}(1-v^2)K(V_{in,0} - V_{in})$$

where v is the Poisson's ratio of the top layer material,
K is the effective spring constant of the cantilever, and A is the circular contact area of the probe The slope of X versus $V_{in}$ for the six applied voltages gives the effective E of the sample. Because there are three cantilevers with three different probing depths, three different effective E values of the sample ($E_A$, $E_B$, and $E_C$) will be measured. These values will be used to calculate $T_{skin}$, $E_{skin}$, and $E_{fat}$ using a system of equations that model the two layer model as two springs in a series.

The spring constants of two springs in a series add as follows:

$$\frac{1}{k \text{ effective}} = \frac{1}{k1} + \frac{1}{k2} \quad (4)$$

The two layers of the model are also in series, so their spring constants add in the same manner. For this model, k1 is the spring constant of the top "skin" layer and $k_2$ is the spring constant of the bottom "fat" layer. Since $$k = \frac{E \text{ of Layer}}{\text{Depth of Layer}} \quad (5)$$

then $$keff = \frac{Eeff(B_A, B_B \text{ or } B_C)}{\text{Depth Sensitivity}(D_A, D_B, \text{ or } D_C)} \quad (6)$$

Figures 27A, 27B, 27C:
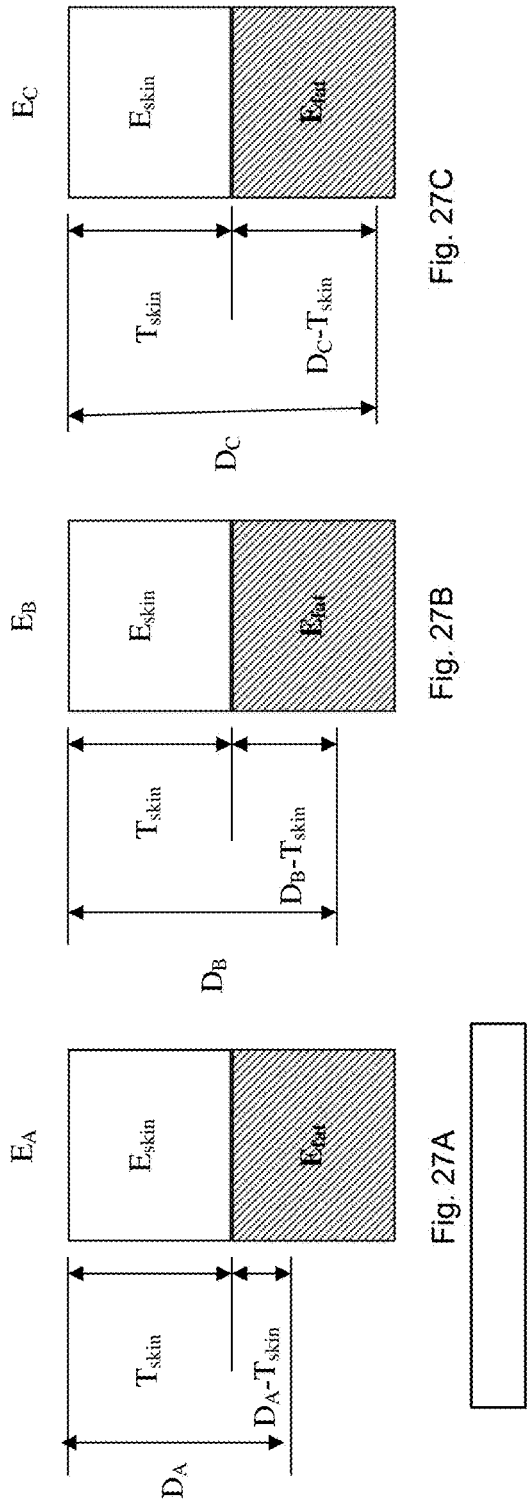
FIG. 27(a) is a diagram illustrating the elastic modulus $E_A$ for a tissue sample measured with a first PEFS having a first depth sensitivity $D_A$.
FIG. 27(b) is a diagram illustrating the elastic modulus $E_B$ for a tissue sample measured with a first PEFS having a first depth sensitivity $D_B$.
FIG. 27(c) is a diagram illustrating the elastic modulus $E_C$ for a tissue sample measured with a first PEFS having a first depth sensitivity $D_C$.

FIG. 27 illustrates how $E_A$, $E_B$, and $E_C$ are composed of $E_{Skin}$ and $E_{fat}$ and relate to equations 4, 5 and 6 above. The following system of equations can be derived using equations 4, 5, and 6:

$$\text{For Cantilever A: } \frac{1}{\frac{E_A}{D_A}} = \frac{1}{\frac{Eskin}{Tskin}} + \frac{1}{\frac{Efat}{(D_A - Tskin)}} \quad (7)$$

$$\text{For Cantilever B: } \frac{1}{\frac{E_B}{D_B}} = \frac{1}{\frac{Eskin}{Tskin}} + \frac{1}{\frac{Efat}{(D_B - Tskin)}} \quad (8)$$

$$\text{For Cantilever C: } \frac{1}{\frac{E_C}{D_C}} = \frac{1}{\frac{Eskin}{Tskin}} + \frac{1}{\frac{Efat}{(D_C - Tskin)}} \quad (9)$$

$E_A$, $E_B$, and $E_C$ are measured values, $D_A$, $D_B$, and $D_c$ are known (twice the diameter of the probe), and therefore the only unknowns in equations 7, 8 and 9 are $T_{skin}$, $E_{skin}$, and $E_{fat}$. By solving the system of equations, values for these three unknowns can be calculated.

The foregoing examples have been presented for the purpose of illustration and description and are not to be construed as limiting the scope of the invention in any way. The scope of the invention is to be determined from the claims appended hereto.

What is claimed is:

1. A method for evaluating tissue to obtain information useful to predict a presence of abnormal tissue, comprising steps of:
    (a) applying a first compressive force to a first location on normal tissue of the subject using at least one sensor comprising a piezoelectric material and a driving electrode for applying a driving force to said sensor;
    (b) detecting a first displacement of said piezoelectric material resulting from application of said first compressive force on said normal tissue while applying said driving force to said sensor;
    (c) applying a second compressive force to a second location on said tissue of said subject using said at least one sensor;
    (d) detecting a second displacement of said piezoelectric material resulting from application of said second compressive force on said second location on said tissue while applying said driving force to said sensor; and
    (e) comparing said first and second displacements.

2. The method of claim 1, further comprising an evaluating step to predict the presence of abnormal tissue.

3. The method of claim 2, wherein said evaluating step predicts type of abnormal tissue.

4. The method of claim 1, wherein said abnormal tissue is cancerous tissue.

5. The method of claim 1, wherein said at least one sensor is an array comprising a plurality of sensors arranged to be capable of each simultaneously applying compressive force to at least one location on said tissue.

6. The method of claim 1, wherein said compressive force is an indentation compressive force.

7. The method of claim 1, wherein step of applying a compressive force to said location on said tissue further comprises the step of applying a set of voltages to said driving electrode.

8. The method of claim 1, further comprising, screening, identifying or diagnosing a type of cancer selected from the group consisting of breast cancer, prostate cancer, skin cancer, or liver cancer.

9. The method of claim 1, wherein the tissue is heterogeneously dense breast tissue.

10. A method for evaluating tissue to obtain information useful to predict a presence of abnormal tissue, comprising a step of:
    (a) applying a first compressive force to a first location on normal tissue of the subject using at least one sensor comprising a piezoelectric material and a driving electrode for applying a driving force to said sensor;
    (b) detecting a first displacement of said piezoelectric material resulting from application of said first compressive force on said normal tissue while applying said driving force to said sensor;
    (c) determining from said first displacement a first net compressive force at said first location exerted by a combination of the compressive force applied at said first location and a countering compressive force resulting from tissue deformation;
    (d) applying a second compressive force to a second location on said tissue of the subject using at least one sensor comprising a piezoelectric material and a driving electrode for applying a driving force to said sensor;
    (e) detecting a second displacement of said piezoelectric material resulting from application of said second compressive force to said tissue at said second location while applying said driving force to said sensor ;
    (f) determining from said second displacement a net compressive force exerted on said second location by a combination of the compressive force applied at said second location and a countering compressive force resulting from tissue deformation; and(g) comparing set first and second net compressive forces.

11. The method of claim 1, wherein the sensor further comprises a second piezoelectric layer.

12. The method of claim 1, wherein the sensor has a rectangular shaped tip.

13. The method of claim 1, further comprising screening for, identifying or diagnosing a type of cancer selected from the group consisting of breast cancer, prostate cancer, skin cancer, or liver cancer.

14. The method of claim 10, further comprising a step of predicting the presence of abnormal tissue at said second location based on information obtained in said comparing step.

15. The method of claim 1, further comprising steps of repeating steps (c)-(d) one or more times at additional different locations on said tissue,
    comparing the determined displacements at said one or more additional different locations to said first displacement, and
    creating a map of the tissue based on said comparisons of the displacements.

16. The method of claim 1, wherein the compressive forces applied at each said location are substantially the same.

17. The method of claim 10, further comprising steps of repeating steps (d)-(f) one or more times at additional different locations on said tissue,
    comparing the determined net compressive forces at said one or more additional different locations to said first net compressive force, and
    creating a map of the tissue based on said comparisons of the net compressive forces.

18. The method of claim 10, wherein the compressive forces applied at each said location are substantially the same.

* * * * *

UNITED STATES PATENT AND TRADEMARK OFFICE
CERTIFICATE OF CORRECTION

Page 1 of 1

PATENT NO.       : 10,076,247 B2
APPLICATION NO.  : 14/465520
DATED            : September 18, 2018
INVENTOR(S)      : Shih et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this
Fourteenth Day of May, 2019

Andrei Iancu
*Director of the United States Patent and Trademark Office*